(12) United States Patent
Kim et al.

(10) Patent No.: US 7,740,856 B2
(45) Date of Patent: Jun. 22, 2010

(54) EFFECT OF BST2 ON INFLAMMATION

(75) Inventors: Myung Kim, Bethesda, MD (US); Jay Chung, Bethesda, MD (US); June-Young Park, Seoul (KR); Hyouna Yoo, Seoul (KR); Sang-Min Lee, Kyeonggi-do (KR); Yoon-Seok Lee, Kyeonggi-do (KR); Mison Koo, Seoul (KR); Sang-Ho Park, Kyeonggi-do (KR)

(73) Assignee: ISU Abxis Co., Ltd., Seoul (KR)

( * ) Notice: Subject to any disclaimer, the term of this patent is extended or adjusted under 35 U.S.C. 154(b) by 0 days.

(21) Appl. No.: 11/471,853

(22) Filed: Jun. 20, 2006

(65) Prior Publication Data

US 2007/0154479 A1 Jul. 5, 2007

Related U.S. Application Data

(63) Continuation-in-part of application No. PCT/KR2005/004398, filed on Dec. 20, 2005.

(30) Foreign Application Priority Data

Dec. 20, 2005 (KR) ............... PCT/KR2005/004398

(51) Int. Cl.
*A61K 39/00* (2006.01)
*A61K 38/00* (2006.01)

(52) U.S. Cl. ...................... 424/184.1; 424/185.1; 514/2

(58) Field of Classification Search ....................... None
See application file for complete search history.

(56) References Cited

U.S. PATENT DOCUMENTS

| | | | |
|---|---|---|---|
| 5,367,056 A | 11/1994 | Hession et al. | |
| 5,821,336 A | 10/1998 | Odink et al. | |
| 5,863,540 A | 1/1999 | Haynes et al. | |
| 5,912,266 A | 6/1999 | Perez | |
| 6,689,869 B2 | 2/2004 | Waldmann et al. | |

FOREIGN PATENT DOCUMENTS

| | | |
|---|---|---|
| EP | 0 972 524 A1 | 1/2000 |
| EP | 1 059 533 A1 | 12/2000 |
| EP | 1 304 379 A2 | 4/2003 |
| EP | 1 394 274 A2 | 3/2004 |
| WO | WO 03/026692 A2 | 4/2003 |
| WO | PCT/KR2005004398 | 2/2009 |

OTHER PUBLICATIONS

Attwood Science 290: 471-473, 2000.*
Skolnick et al. Trends in Biotech. 18: 34-39, 2000.*
Mori et al. Archives of Virology 1999, 144:147-155.*
Gencic et al. The Journal of Neuroscience 1990, 10:117-124.*
NCBI Accession No. BAA05679, Feb. 8, 2003.
NCBI Accession No. AAH56638, Dec. 2, 2004.
Ohtomo et al., "Molecular Cloning and Characterization of a Surface Antigen Preferentially Overexpressed on Multiple Myeloma Cells", Biochemical and Biophysical Research Communications (1999), 258: 583-591.
Ohtomo, et al., "Molecular Cloning and Characterization of a Surface Antigen Preferentially Overexpressed on Multiple Myeloma Cells," Biochemical and Biophysical Research Communications, 1999, 258:583-591.
Strausberg, et al., "Generation and Initial Analysis of more than 15,000 full-length human and mouse cDNA sequences," Proc. Natl. Acad. Sci. U.S.A., 2002, 99(26), 16899-16903.
Ishikawa, et al., "Molecular cloning and chromosomal mapping of a bone marrow stromal cell surface gene, BST2, that may be involved in pre-B-cell growth," Genomics, 1995, 26(3), 527-534.
NCBI Accession No. Q10589 (Mar. 15, 2004).
PCT/KR2005/004398 Search Report.

* cited by examiner

*Primary Examiner*—Phillip Gambel
*Assistant Examiner*—Sharon Wen
(74) *Attorney, Agent, or Firm*—Joseph H. Kim; JHK Law

(57) ABSTRACT

The application disclose a method of preventing immune cells from binding to other cells, which includes contacting the immune cells and the other cells with a composition comprising Bst2 antagonist.

8 Claims, 28 Drawing Sheets

Human Bst2 & mouse Damp-1 genes

Identities = 70/180 (38.9%), Positives = 82/180 (45.6%), Gaps = 41/180 (22.8%)

human_bst2  189 (SEQ ID NO:3)
mouse_damp1  172 (SEQ ID NO:4)

Fig. 2
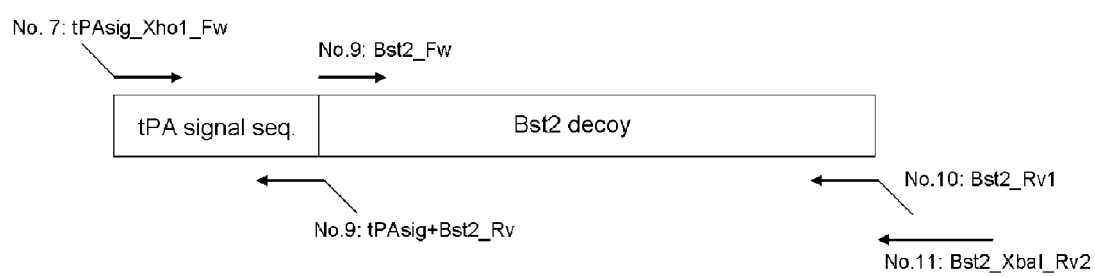
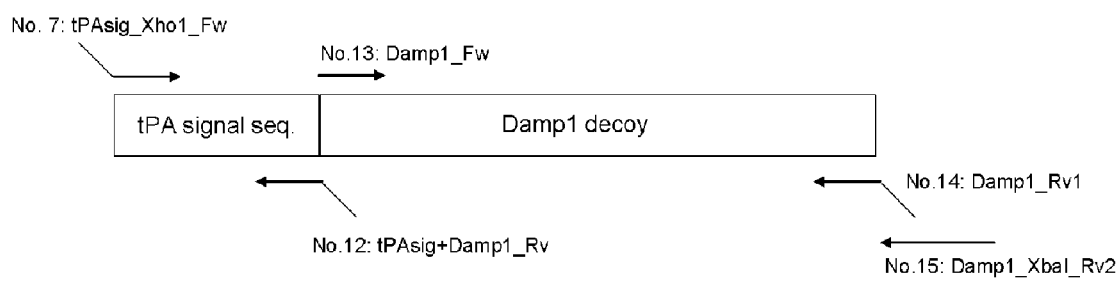

SM. Size marker
1. Bst2 decoy, non-reducing
2. Damp1 decoy, non-reducing
3. Bst2 decoy, reducing
4. Damp1 decoy, reducing SM. Size marker
1. Bst2 decoy, non-reducing
2. Bst2 decoy, reducing
3. Bst2 decoy, reducing, deglycosylation

* time: hours after inducing homotypic aggregation

A: No treatment
B: untransfected cells treated with PMA and LPS
C: mock-transfected cells treated with PMA and LPS
D: Bst2-transfected cells treated with PMA and LPS A. No treatment
B. PMA + LPS
C. PMA + LPS + control media
D. PMA + LPS + Bst2 decoy media

Fig. 7
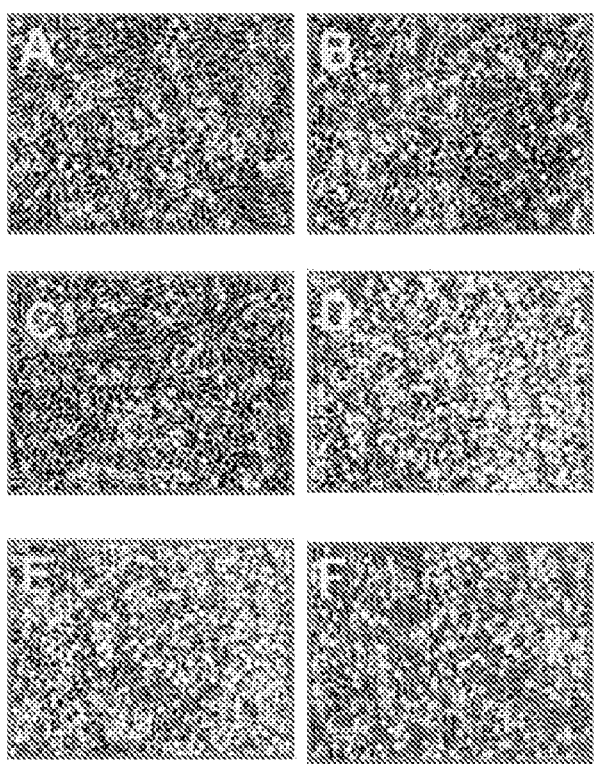
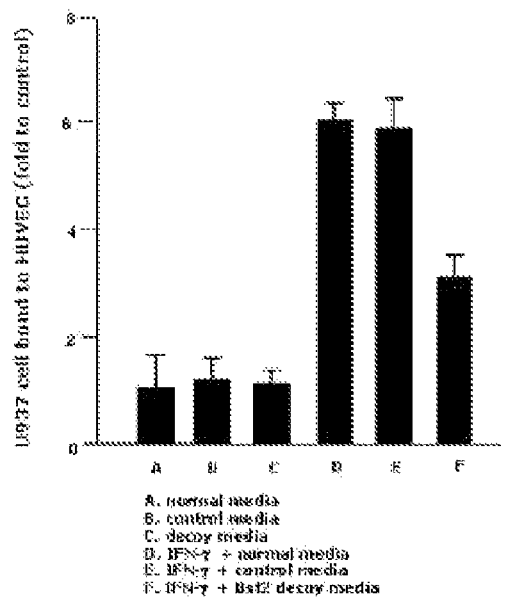

A. control
B. IFN-γ treated
C. Bst2-transfected HUVEC cells
D. Bst2-transfected HUVEC cells treated with IFN-γ
E. Bst2-transfected HUVEC cells treated with Bst2 siRNA
F. mock-transfected HUVEC cells treated with IFN-γ and Bst2 siRNA Fig. 13
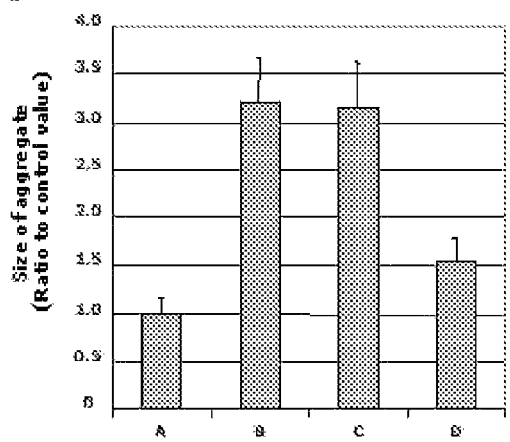
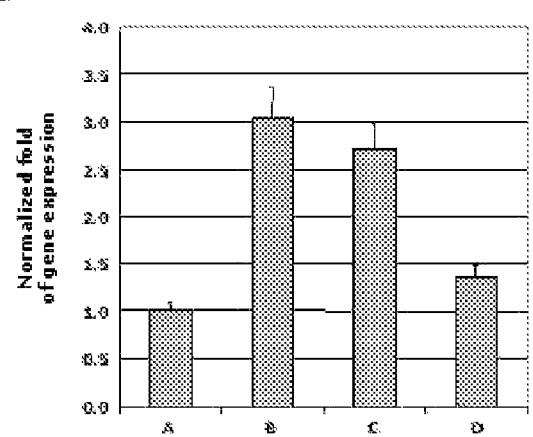
A. Control
B. Cells treated with OKT antibody
C. Cells treated with OKT and control decoy
D. Cells treated with OKT and Bst2 decoy A. saline
B. Ovalbumine (OVA)
C. OVA + Bst2 decoy
D. OVA + Damp1 decoy

Fig. 18
mPEG-Aldehyde (mPEG-propionaldehyde)
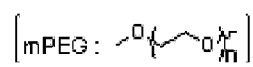
mPEG-SC (mPEG-succinimidyl carbonate)
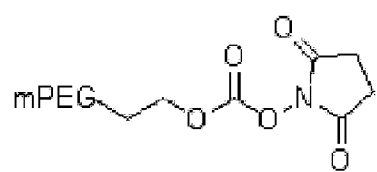

Fig. 20
Asthma
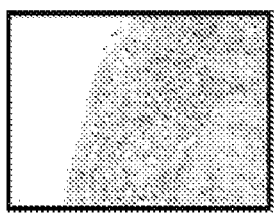
Atherosclerosis
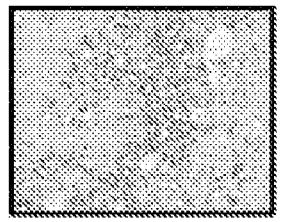
Rheumatoid Arthritis
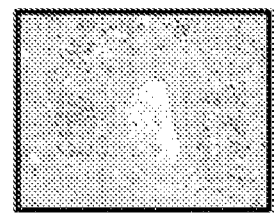
Psoriasis
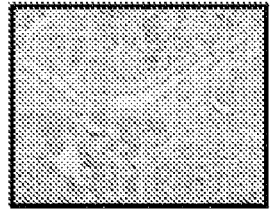
Crohn's Disease
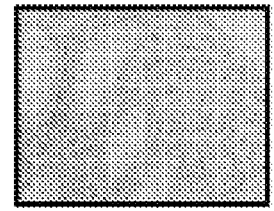
Ulcerative Colitis
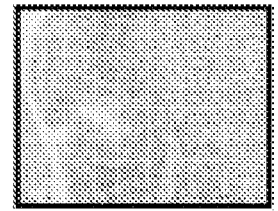

Figure 22.
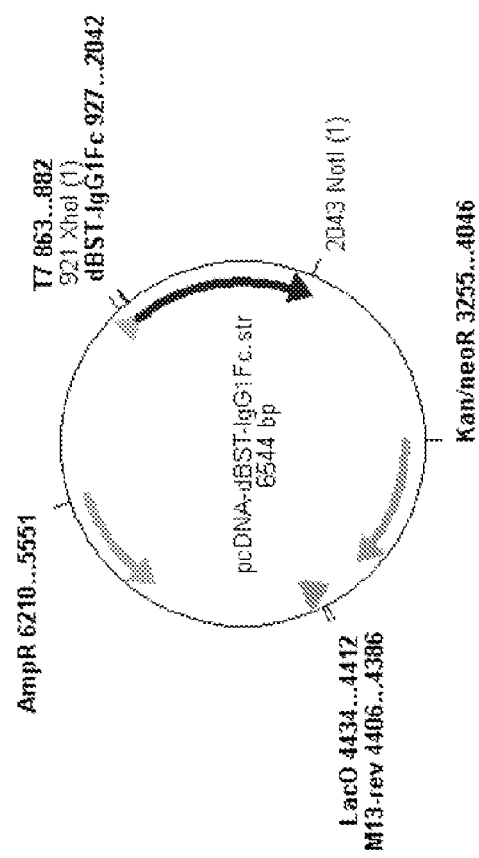
(B)
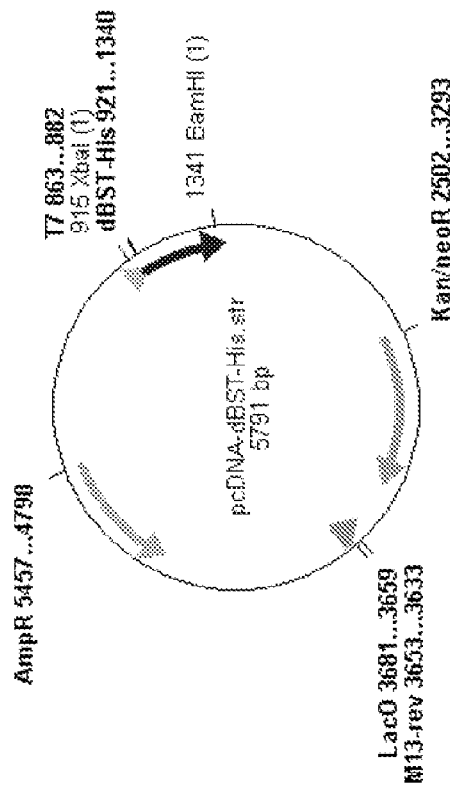
(A)

Figure 22.
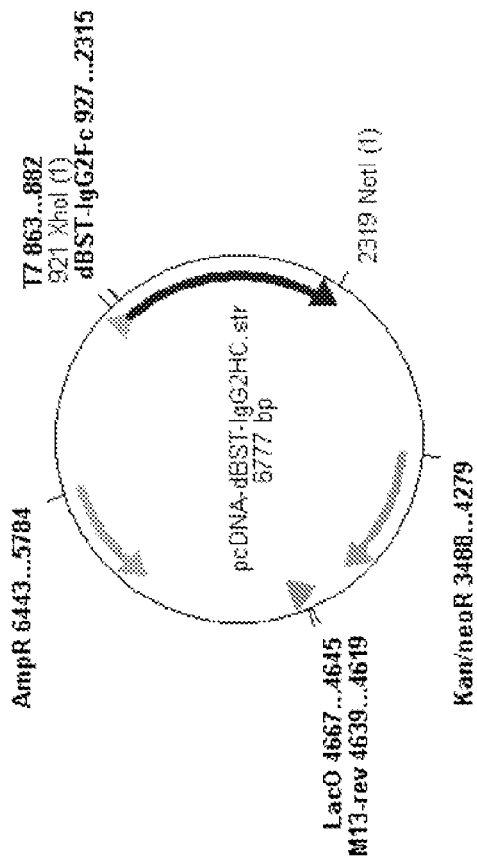
(D)
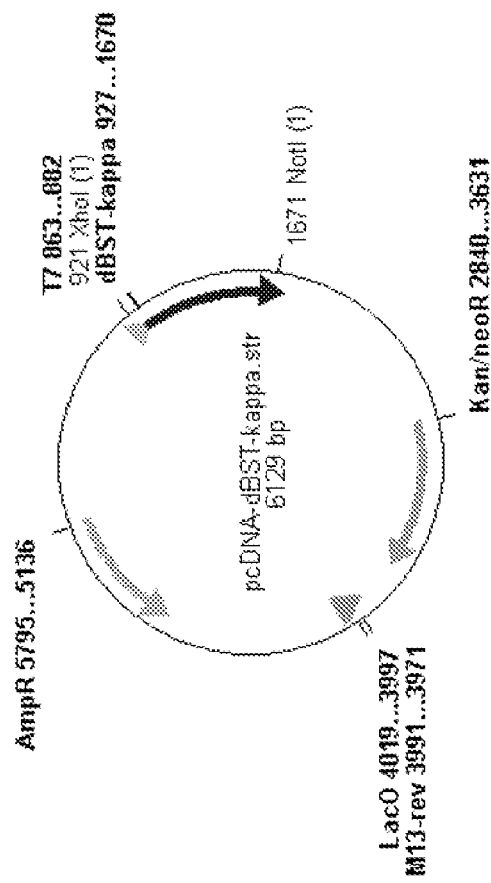
(C)

Figure 30A

|      | FR1 | CDR1 | FR2 | CDR2 |
|------|-----|------|-----|------|
|      |     | ***** |    | ****************** |
| 2-15 | MAQSVKESEGRLVTPGTPLTLTCTVSGFSLSNSGMSWVRQAPGKGLEWIGL | INSYGTTYYASWAKG |
| 2-14 | MAQSVKESEGGLFKPTDTLTLTCTVSGFSLSSYEMNWVRQAPGKGLEYIGI | IRSDGSTYYASWAKS |
| 2-10 | MAQSLEESGGRLVKPDETLTLTCTVSGIDLSSYMIYWVRQAPGKGLEYIGF | IYGSGDTYYATWAKG |
| 2-4  | MAQQLVESGGGLVTPGGTLTLTCTASGIDLSSYHMQWVRQAPGKGLEYIGF | IDTVGSAYYASWAKG |
| 2-5  | MAQQQLVESGGGLVTPGTPLTLTCTVSGFSLSSYAMIWVRQAPGKGLEYIGI | IRSSGNTYYASWAKG |
| 2-7  | MAQSVKESEGGLFKPTDTLTLTCTVSGFSLSSHEMNWVRQAPGNGLEYIGI | INSYANTYYAGWAKS |
| 2-9  | MAQSLEESGGRLVTPGTPLTLTCTVSGIDLSSYEMSWVRQAPGKGLEYIGF | ISTSGNTYYASWAKG |
| 2-11 | MAQEQLMESGGGLVTPGGILSLTCTASGFSISSYRMGWVRQAPGKGLEWIGF | INNYGSAYYASWAKS |
| 2-13 | MAQEQLVESGGRLVTPGGSLTITCTVSGIDLSGYAMGWVRQAPGKGLEYIGI | IGTSDTTYYASWAKG |
| 2-19 | MAQSVKESEGGLFKPTDTLTLTCTVSGFSLSSYEMNWVRQAPGKGLEYIGI | IIRSDGSTYYASWAKS |
| 2-24 | MAQSVEESRGGLFKPTDTLTLTCTVSGFSLSTYEMNWVRQAPGSGLEYIGI | INSAGTTYYASWAKS |

|      | FR3 | CDR3 | FR4 | |
|------|-----|------|-----|---|
|      |     | ********** | | |
| 2-15 | RFTISKTKTSTTVELKITSPTTEDTATYFCAR | GAGSSYGL | WGQGTLVTVSSAS | (SEQ ID NO:149) |
| 2-14 | RSTITRNTNLNTVTLKMTSLTSPTTGDTATYFCAR | SSGWGYGLDL | WGPGTLVTVSSAST | (SEQ ID NO: 150) |
| 2-10 | RFTISRPSTTVDLKITSPTTGDTATYFCAR | DSGYSIGTL | WGPGTLVTISSAST | (SEQ ID NO: 151) |
| 2-4  | RFTISRTSTTVDLKMTSLTAADTATYFCAG | DSGYSFGL | WGQGTLVTVSSAST | (SEQ ID NO: 152) |
| 2-5  | RFTISKTSTTVDLKITSPTTEDTATYFCAR | | WGQGTLVTVSSAST | (SEQ ID NO: 153) |
| 2-7  | RSTITRNTNENTVTLTMTSLTAADTAAYFCAR | GPAKSGYGTRLDL | WGPGTLVTISSAST | (SEQ ID NO: 154) |
| 2-9  | RFTISKTSTTVDLKITSPTIEDTAAYFCAR | | WGQGTLVTVSSAST | (SEQ ID NO: 155) |
| 2-11 | RSTITRNTNLNTVTLKMTSLTAADTATYFCARE | SYSYGYAYDI | WGPGTLVTVSSAST | (SEQ ID NO: 156) |
| 2-13 | RFTISKTSSTTVDLKMTSLTTEDTATYFCVR | SPGGSA0 | WGQGTLVTISSAST | (SEQ ID NO: 157) |
| 2-19 | RSTITRNTNLNTVTLKMTSLTAADTATYFCARDL | GYSNDV | WGPGTLVTISSAST | (SEQ ID NO: 158) |
| 2-24 | RSTITRNTNENTVTLKMTSLTAADTATYFCARDL | GYSSDI | WGPGTLVTISSAST | (SEQ ID NO: 159) |

Figure 30B

```
            FR1                          CDR1            FR2                     CDR2
            ****************    ****************    ****************
2-15   QAAELVMTQTPSSTSTAVGDTVTIKCQASQSIGSNLAWYQQKPGQPPKILIYSASNLAS
2-14   -------DL-----------------G----N----I--------L--WY--D---
2-10   -------DL-----------------G----N-------NVW-S-L--Q--K---
2-4    ----------V-A-------------G----N---T--I-------L--WY--D---
2-5    ----------V-A-------------G----N-KN---I-------Q--WY--D---
2-7    ----------L---------------G----N------I-------L--WY--D---
2-9    -------DL-----------------G----N------I-------L--WY--D---
2-11   -------DL---------------T-G----N-R----I----F--L--WY--D---
2-13   -------D------------------G---MN------I-------L--WY--D---
2-19   ----------L---------------G----N------I-------L--WYT-D---
2-24   --------------------------G----N------I-------L--WY--D---

FR3                    CDR3                 FR4
                            ****************
2-15   GVPSRFKGSGSGTEYTLTISGVQREDAATYYCLGSDSSWDTVFGGGTELEIILRTV  (SEQ ID NO: 161)
2-14   --S-----F-----QF----------------TYG-G-RA--A--NV--K---    (SEQ ID NO: 162)
2-10   --------F-----QF---------V------IYNDID-A----VVVK---      (SEQ ID NO: 163)
2-4    --------F-----QF---------N------YG-G-RA--A--NV-IK---     (SEQ ID NO: 164)
2-5    --------F-----QF---------N------YG-G-RA--A--NV--K---     (SEQ ID NO: 165)
2-7    --------F-----QF----------------YG-G-RA--A--NV--K---     (SEQ ID NO: 166)
2-9    --------F-----QF-------N-E------TYG-G-RA--A--NV--K---    (SEQ ID NO: 167)
2-11   -----R-NV--SQF------------------TYG-GVRA--A--NV--K---    (SEQ ID NO: 168)
2-13   --------F-----QF-------M--------TYG-GVRA--A--NV--K---    (SEQ ID NO: 169)
2-15   --------F-----QF------AI--------TYG-GVRA--A--NV--K---    (SEQ ID NO: 170)
2-19   -----R--F-----QF------AI--------TYG-GVRA--A--NV--K---    (SEQ ID NO: 171)
2-24   -A------F-----QF----------------TYG-G-RA--T--NV--K---    (SEQ ID NO: 172)
```

Figure 31
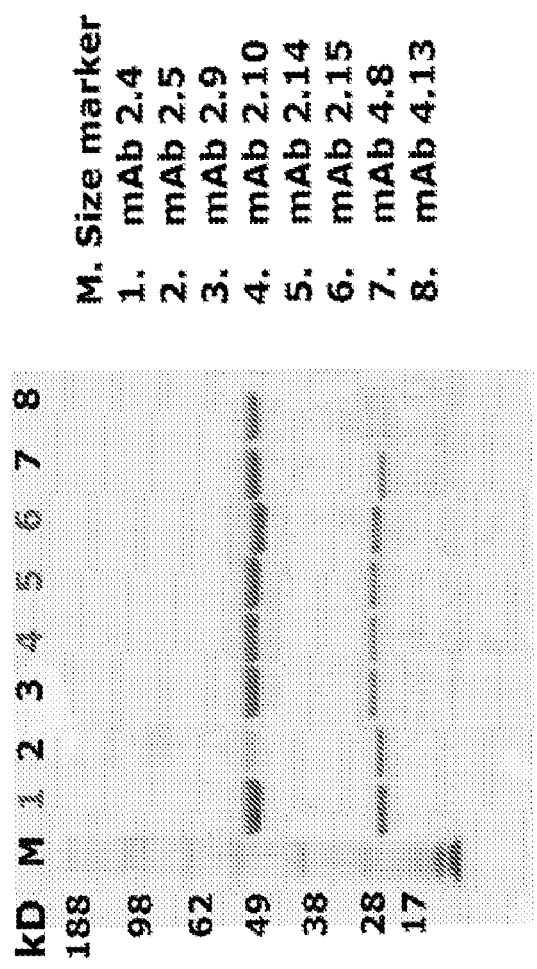
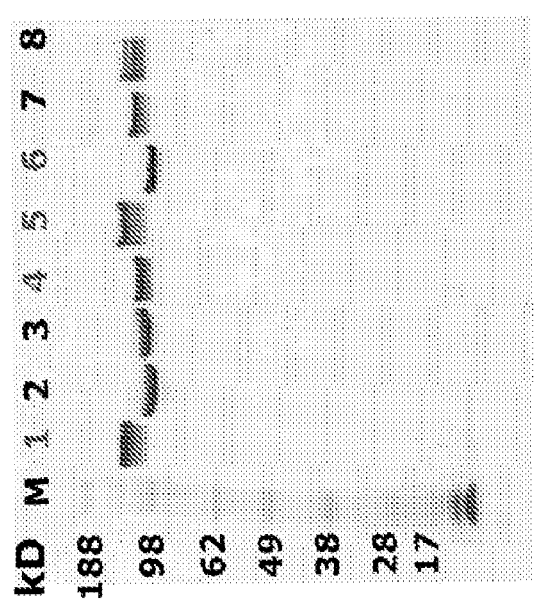

EFFECT OF BST2 ON INFLAMMATION

CROSS-REFERENCE TO RELATED APPLICATIONS

The present application is a continuation-in-part of PCT/KR2005/004398, filed Dec. 20, 2005, which designates the U.S. and claims benefit of priority to Korean patent application 10-2004-0108909, filed Dec. 20, 2004. The contents of PCT/KR2005/004398 is incorporated by reference herein in its entirety.

BACKGROUND OF THE INVENTION

1. Field of the Invention

The present invention relates to molecules inhibiting intercellular adhesion during inflammation and the use of the same. The present invention also relates to using Bst2 protein or fragments thereof as a decoy or Bst2-binding antibody in inhibiting intercellular adhesion of cells participating in inflammation. The present invention is also concerned with a composition, comprising the same, and a method for preventing or treating inflammation-associated diseases.

2. General Background and State of the Art

Inflammation is a normal response of the body to protect tissues from infection, injury or diseases. The inflammatory response begins with the production and release of chemical agents by cells in the affected tissues. The chemical agents cause redness, swelling, pain, heat and loss of function. Cells in inflamed tissues generate signals that recruit leukocytes to the site of inflammation. Leukocytes must adhere to endothelial cells to migrate from the bloodstream into the site of inflammation. Also, leukocytes should adhere to antigen-presenting cells to allow normal specific immune responses, and should finally adhere to suitable target cells to lyse pathogen-infected cells, cancer cells, or the like. The recruited leukocytes eliminate any infective or injurious agent and remove debris of damaged cells from the injured tissue.

The infiltrating leukocytes play critical roles in tissue regeneration and immune response in normal inflammation by engulfing invading microorganisms or dead cells. However, the infiltrating leukocytes cause serious or lethal status in pathological chronic inflammation. The abnormal recognition of self cells as non-self (foreign) or excess inflammation by sustained inflammatory responses causes a variety of inflammatory diseases including diabetes mellitus, atherosclerosis, cataract, reperfusion injury, infectious meningitis, rheumatoid arthritis, asthma, sepsis, inflammatory bowel disease and multiple sclerosis.

The interaction between leukocytes and endothelial cells is as follows.

Leukocytes have dual functions to act in a form circulating in the bloodstream or adhering to specific cells. In particular, adherent leukocytes interact with endothelial cells, stabilize intercellular adhesion with antigen-presenting cells or act as effector cells to migrate into inflammatory or infected sites. For normal specific immune response, leukocytes should adhere to antigen-presenting cells and should finally adhere to suitable target cells to lyse pathogen-infected cells, cancer cells, or the like. A massive invasion of leukocytes occurs in an allograft rejection, skin infection or in an injured area, and is also observed in various diseases including degenerative joint diseases, such as osteoarthritis, psoriasis, multiple sclerosis, asthma, rheumatoid arthritis, contact dermatitis and inflammatory bowel disease In such diseases, greater than 95% of myeloid cells move to and accumulate at the site of inflammation. Leukocytes are crucial agents of the inflammatory response, which exert antimicrobial, secretory and phagocytic activity. They gather in tissues where inflammation is occurring or needs to occur by producing a water-soluble mediator or through specific adhesion to various cells. In fact, anti-inflammatory agents such as nonsteroidal anti-inflammatory drugs (NSAIDs) or glucocorticoid exert therapeutic efficacy by preventing the adhesion and influx of leukocytes. In animal models, the inhibition of intercellular adhesion improves or prevents diseases or allograft rejection in animal models of autoimmune diseases. Recent clinical studies have revealed that humanized monoclonal antibodies inhibiting LFA-1/ICAM-1 or VLA-4/VCAM-1 interaction have significant efficacy and good safety on autoimmune diseases including psoriasis, multiple sclerosis and inflammatory bowel disease.

The uncontrolled invasion of leukocytes into endothelial cells, which is a key feature in the pathogenesis of inflammation-associated diseases, occurs by a multi-step process, which begins with leukocyte adhesion and binding to the surface of endothelial cells. The binding of leukocytes to endothelial cell surface is mediated by cell surface molecules present on the surface of leukocytes and endothelial cells [Bevilacqua, $J.$ $Clin.$ $Invest.$ 11:767-804, 1993]. The cell surface molecules are overexpressed as a result of migration of leukocytes from the bloodstream.

The interaction between leukocytes and endothelial cells is a critical factor in many inflammatory diseases. For example, increased leukocyte-endothelial interaction leading to hepatic microperfusion disorders is proposed as a major contributor of hepatic failure [Croner et al., $Microvasc.$ $Res.$ 67:182-191, 2004]. For example, atherosclerosis is a typical inflammatory disease in which a number of inflammatory cells including T lymphocytes and activated macrophages are concentrated in the site of atherosclerosis. The accumulation and adhesion of monocytes in discrete segments of arterial endothelium is among the earliest detectable events in atherogenesis and is a central feature of the pathogenesis of atherosclerosis [Ross, $Nature$ 362:801-809, 1993]. In this region, proinflammatory cytokines are abundant, which include interferon-gamma and tumor necrosis factor-alpha, regulating regional inflammatory response. A great number of adhesion molecules are expressed on the surface of monocytes [Valente et al., $Circulation$ 86:III20-25, 1992], and endothelial cells overlying atherosclerotic lesions express a number of vascular ligands [Poston et al., $Am.$ $J.$ $Pathol,$ 140:665-673, 1992].

The extravasation of leukocytes across the endothelial barrier is a critical event in the pathogenesis of inflammatory diseases such as rheumatoid arthritis. Endothelial cells participate in the basic mechanism of arthritis, by which various inflammation mediators, such as tumor necrosis factor-alpha and inflammation-inducing cytokines such as interleukin-1 beta, activate endothelial cells. This leads to elevated expression of endothelial cell adhesion molecules in rheumatoid arthritis, resulting in increased interaction between leukocytes and endothelial cells. The recruitment of leukocytes to vascular endothelial cells is also an important step of asthma.

In the airway of patients with asthma, there are increased numbers of activated eosinophils, CD25-positive T lymphocytes and immature macrophages with the phenotypic characteristics of blood monocytes. The expression of HLA class II increases in epithelial cells, macrophages, and other infiltrating cells [Arm et al., $Adv.$ $Immunol.$ 51:323-382, 1992]

An increased rate of leukocyte transmigration across the blood-brain barrier is a major symptom in multiple sclerosis. The interaction between tight junction proteins in leukocytes and those in endothelial cells contributes to the leukocyte extravasation to the central nervous system under physiological conditions, and the altered expression of tight junction proteins is a pathological prerequisite for multiple sclerosis [Worthylake et al., *Curr. Opin. Cell Biol.* 13:569-577, 2001].

As described above, since the adhesion of leukocytes to endothelial cells is important in a variety of diseases, the inhibition of intercellular adhesion may result in a therapeutic strategy for diverse inflammatory and immune diseases.

With respect to the molecular biology, the following molecules are known to participate in inflammation.

Cytokines: systemic inflammation, which is a general response to serious bacterial infections or traumatic injuries, may affect tissue systems distal to the early damage [Lush and Kvietys, *Microcirculation* 7:83-101, 2000]. Bacterial products and other inflammation-inducing mediators, released from affected tissues, induce the formation of inflammation-inducing mediators including tumor necrosis factor-alpha (TNF-alpha), interleukin-1 beta, gamma-interferon and interleukin-6. In sepsis, vascular endothelial damage promotes the production of TNF-alpha and interleukin-1 beta. These cytokines directly act on endothelial cells and enhance leukocyte adhesion [Pober et al., *J. Immunol.* 137:1893-1896, 1986; Dustin and Springer, *J. Cell Biol.* 107:321-331, 1988; Cotran and Pober, *J. Am. Soc. Nephrol.* 1:225-235, 1988]. These cytokines also activate blood neutrophils in blood and vascular endothelium [Arai et al., *Annu. Rev. Biochem.*, 59:783-836, 1990]. For example, TNF-alpha induces a series of cytokines, chemokines and proteases by an autocrine or paracrine pathway [Ghezzi and Cerami, *Methods Mol. Med.* 98:1-8. 2004]. Interleukin-6 induces mononuclear-endothelial cell interaction and inflammatory damage through expression of adhesion molecules, thus initiating a process of atherosclerosis. Increased blood concentration of interleukin-6 involves vascular inflammation and development of atherosclerosis [Rader, *N. Engl. J. Med.* 343:1179-1182, 2000]. Interleukin-17 induces the expression of many mediators of inflammation, and is involved in the differentiation, maturation and chemotaxis of neutrophils [Witowski et al., *Cell Mol Life Sci.* 61:567-579, 2004]. Increased levels of interleukin-17 have been associated with several pathological conditions, including airway inflammation, rheumatoid arthritis, intraperitoneal abscesses and adhesions, inflammatory bowel disease, allograft rejection, psoriasis, cancer and multiple sclerosis Cell surface adhesion molecules: a plurality of inflammatory cytokines induce the expression of endothelial cell-lymphocyte adhesion molecules (ELAMs) on the cell surface [Nortamo et al., *Eur. J. Immunol.* 21:2629-2632, 1991]. They are divided into two classes: intercellular adhesion molecule-1 (ICAM-1) and endothelial cell-lymphocyte adhesion molecule-1 (ELAM-1) [Staunton et al., *Cell* 52:925-933, 1988]. In response to various mediators, vascular endothelium expresses specific cell surface glycoproteins. The binding and extravasation of blood leukocytes are achieved by interaction with a specific ligand or counterreceptor [Bevilacqua et al., 1993, 1994]. Molecules participating in this process include intercellular adhesion molecule-1 (ICAM-1) as a ligand for CD18, selectins recognizing glycoconjugates on the leukocyte surface, and members of the immunoglobulin superfamily interacting with other members of the same family, and leukocyte integrin molecules [Panes et al., *J. Physiol.* 269:H1955-1964, 1995; Khan et al., *Microcirculation* 10:351-358, 2003; Nelson et al., *Blood* 82:3253-3258, 1993; Bevilacqua and Nelson, *J. Clin. Invest.* 91:379-387, 1993]. Leukocyte rolling is regulated by selecting, and transmigration and adhesion of leukocytes on endothelial cells are triggered by the beta 2 integrin, Mac-1 (CD11b/CD18, aMb2, CR3), and LFA-1. Mac-1 and LFA-1 interact with a counter-receptor expressed on the surface of endothelial cells, ICAM-1.

The prior art associated with inflammation therapy are as follows.

U.S. Pat. No. 5,367,056 describes the inhibition of the binding of polymorphonuclear leukocytes (PMNs) to endothelial cells by treatment of molecules or fragments thereof interrupting the binding to endothelial cell-leukocyte adhesion molecules (ELAMs) as receptors or ligands. This patent also describes antisense nucleotides and ribozymes for suppressing ELAM expression. This patent further describes a method for identifying molecules which inhibit the binding of ELAM to its ligand, and antibodies against ELAM and its ligands.

U.S. Pat. No. 5,863,540 discloses a method of suppressing T cell activation by administrating a CD44 protein peptide or a derivative thereof in an amount sufficient to suppress T cell activation. Also disclosed is a method of inhibiting CD44-mediated cell adhesion or CD44-mediated monocyte IL-1 release by administering the CD44 protein peptide or derivative thereof in an amount sufficient to inhibit CD44-mediated cell adhesion or monocyte IL-1 release. Further disclosed is a method of transporting a drug or cytotoxic agent to a site of inflammation by administering the CD44 protein peptide or derivative thereof linked to the drug or cytotoxic agent.

The U.S. Pat. No. 5,912,266 involves the inhibition of intercellular adhesion mediated by the beta 2 integrin family of cell surface molecules. Through this inhibitory action, a pharmaceutical composition according to this patent is useful for inhibiting or treating inflammatory and other pathological responses associated with cell adhesion. This patent also discloses a method of inhibiting or treating pathological conditions where leukocytes and lymphocytes cause cellular or tissue damage.

WO2003/026692 relates to the therapeutic use of an antibody against CD3 antigen complexes in patients with chronic articular inflammation and rheumatoid arthritis.

EU 1304379 relates to a humanized anti-CD18 antibody comprising a portion or the whole of an antigen-determining region capable of binding to CD18 antigen.

U.S. Pat. No. 6,689,869 describes the use of a humanized anti-CD18 antibody in inhibiting influx of leukocytes into the lung and other organs during sepsis, and other infectious or non-infectious traumas. The humanized anti-CD18 antibody can be used for inhibiting the ingress of leukocytes into the lung and other organs in patients having endotoxic shock or adult respiratory distress syndrome. The antibody can administered to treat asthma or leukocyte-mediated reperfusion damage post thrombolytic therapy. Also, the antibody can be used to reduce or eliminate inflammation in a patient being administered with an anti-infective agent, or to assist in the administration of a therapeutic drug to a patient during anti-cancer chemotherapy.

U.S. Pat. No. 5,821,336 describes polypeptides having a molecular weight of 160 kD, which are mediators or precursors for mediators of inflammation, derivatives thereof, such as mutants and fragments, and processes for their preparation. Nucleotide sequences coding for the polypeptides and derivatives, vectors comprising the nucleotide sequences, antibodies against the polypeptides or their derivatives and antibody derivatives are also included in the scope of this patent. Moreover described are diagnostic and therapeutic methods for inflammatory conditions and Hodgkin's lymphomas using the antibodies and antibody derivatives.

SUMMARY OF THE INVENTION

Inflammation requires at least three sequential steps to attracting immune cells comprising leukocytes into the site of inflammation, as follows: (1) immune cells including leukocytes such as lymphocytes, polymorphonuclear leukocytes, natural killer cells and macrophages are activated by cytokines and or intercellular interaction; (2) the aggregated immune cells migrate and are recruited to the site of inflammation, where they transduce related signals into endothelial cells through adhesion to endothelial cells; (3) T lymphocytes and macrophages are activated and secrete cytokines, such as interleukin-2, to amplify the inflammatory response.

In one aspect, the invention is directed to a method of preventing immune cells from binding to other cells, comprising contacting the immune cells and the other cells with a composition comprising Bst2 antagonist. The other cells may be immune cells or endothelial cells. And the Bst2 antagonist is a Bst2 decoy or a Damp1 decoy. The Bst2 decoy may be a fragment of Bst2 or a variant thereof, which retains improved binding or decoy activity compared to Bst2 protein towards another Bst2 molecule or proteins that interact with Bst2. Likewise for Damp1. Further, the Bst2 antagonist may be Bst2 decoy-Fc chimeric or fusion construct, Bst2-decoy-albumin chimeric or fusion construct, or linked to a non-proteinaceous polymer.

In another aspect of the invention, in the above method, the Bst2 antagonist may be a monoclonal antibody to Bst2 or monoclonal antibody to mouse Damp1 protein or both.

In the above method the immune cells and other cells may be either located at a site of inflammation or at a site distant from inflammation but can transmit inflammatory and immune cytokines or other inflammatory signals to a site of inflammation.

In another embodiment, the invention is directed to a Bst2 decoy-Fc chimeric construct. The Bst2 decoy-Fc chimeric construct may be a Bst2 decoy fused to the hinge-CH2-CH3 portion of an IgG heavy chain Fc; Bst2 fusion protein that is stabilized through IgG kappa chain-heavy chain disulfide bonding; or Bst2 decoy-IgG Fc without other Bst2 dimerization counterparts.

The invention is also directed to a monoclonal antibody specific for Bst2, Damp1 or Bst2 and Damp1. The monoclonal antibody may one wherein a cell expressing Bst2 to which the monoclonal antibody is bound prevents Bst2 ligand-Bst2 interaction or Bst2-Bst2 interaction.

In a particular aspect of the invention, the monoclonal antibody may have an amino acid sequence in the heavy chain variable region in the CDR1 region selected from SEQ ID NO:68, SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95, and SEQ ID NO:98.

In another aspect, the monoclonal antibody may have an amino acid sequence in the heavy chain variable region in the CDR2 region selected from SEQ ID NO:69, SEQ ID NO:72, SEQ ID NO:75, SEQ ID NO:78, SEQ ID NO:81, SEQ ID NO:84, SEQ ID NO:87, SEQ ID NO:90, SEQ ID NO:93, SEQ ID NO:96, and SEQ ID NO:99.

In yet another aspect, the monoclonal antibody may have an amino acid sequence in the heavy chain variable region in the CDR3 region selected from SEQ ID NO:70, SEQ ID NO:73, SEQ ID NO:76, SEQ ID NO:79, SEQ ID NO:82, SEQ ID NO:85, SEQ ID NO:88, SEQ ID NO:91, SEQ ID NO:94, SEQ ID NO:97, and SEQ ID NO:100.

In still another aspect of the invention, monoclonal antibody may have an amino acid sequence in the heavy chain variable region comprised of the following:
(i) in the CDR1 region, SEQ ID NO:68, SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95, or SEQ ID NO:98;
(ii) in the CDR2 region, SEQ ID NO:69, SEQ ID NO:72, SEQ ID NO:75, SEQ ID NO:78, SEQ ID NO:81, SEQ ID NO:84, SEQ ID NO:87, SEQ ID NO:90, SEQ ID NO:93, SEQ ID NO:96, or SEQ ID NO:99; and
(iii) in the CDR3 region, SEQ ID NO:70, SEQ ID NO:73, SEQ ID NO:76, SEQ ID NO:79, SEQ ID NO:82, SEQ ID NO:85, SEQ ID NO:88, SEQ ID NO:91, SEQ ID NO:94, SEQ ID NO:97, or SEQ ID NO:100.

In a further aspect, the invention is directed to a monoclonal antibody having an amino acid sequence in the kappa chain variable region in the CDR1, SEQ ID NO:101, SEQ ID NO:104, SEQ ID NO:107, SEQ ID NO:110, SEQ ID NO:113, or SEQ ID NO:114.

In another aspect, the monoclonal antibody may have an amino acid sequence in the kappa chain variable region in the CDR2 of SEQ ID NO: 102, SEQ ID NO: 105, SEQ ID NO: 108, SEQ ID NO:111, or SEQ ID NO:116.

In another aspect, the monoclonal antibody may have an amino acid sequence in the kappa chain variable region in the CDR3 of SEQ ID NO: 103, SEQ ID NO: 106, SEQ ID NO: 109, SEQ ID NO:112, or SEQ ID NO:115.

In still another aspect, monoclonal antibody may have an amino acid sequence in the kappa chain variable region comprised of the following:
(i) in the CDR1 region, SEQ ID NO:101, SEQ ID NO:104, SEQ ID NO:107, SEQ ID NO:110, SEQ ID NO:113, or SEQ ID NO:114;
(ii) in the CDR2 region, SEQ ID NO:102, SEQ ID NO:105, SEQ ID NO:108, SEQ ID NO:111, or SEQ ID NO: 116; and
(iii) in the CDR3 region, SEQ ID NO:103, SEQ ID NO:106, SEQ ID NO:109, SEQ ID NO:112, or SEQ ID NO:115.

In another aspect, the invention is directed to a method of reducing inflammation in a subject comprising administering a composition comprising Bst2 antagonist to a site of the inflammation. The Bst2 antagonist may be Bst2 decoy, Bst2-Fc chimera, Bst2-albumin chimera, anti-Bst2 monoclonal antibody, anti-Damp1 antibody, or a monoclonal antibody that is specific for both Bst2 and Damp1.

In yet another embodiment, the invention is directed to a method of treating a disease associated with inflammation in a subject comprising administering a composition comprising Bst2 antagonist to the person in need thereof. The disease may be selected from: atherosclerosis, rheumatoid arthritis, asthma, sepsis, ulcerative colitis, multiple sclerosis, acute myocardial infarction, heart attack, psoriasis, contact dermatitis, osteoarthritis, rhinitis, Crohn's disease and autoimmune diseases. In this method, the Bst2 antagonist may be multi monoclonal antibodies specific to different epitopes. Further, the composition may comprise Bst2 decoy or its variants and monoclonal antibodies against Bst2.

In still another aspect, the invention is directed to an isolated nucleic acid encoding the monoclonal antibody, Bst2 decoy-Fc chimeric construct and Damp1 decoy chimeric construct described above.

These and other objects of the invention will be more fully understood from the following description of the invention, the referenced drawings attached hereto and the claims appended hereto.

BRIEF DESCRIPTION OF THE DRAWINGS

The present invention will become more fully understood from the detailed description given herein below, and the accompanying drawings which are given by way of illustration only, and thus are not limitative of the present invention, and wherein

FIG. 2 shows the locations of PCR primers used in a process for cloning a human Bst2 soluble fragment and a mouse Damp1 soluble fragment into an expression vector;

FIG. 7 shows the effect of a Bst2 soluble fragment on intercellular adhesion between human vascular endothelial (HUVEC) cells and U937 cells;

FIGS. 13A-13B shows graphs showing the effect of a Bst2 soluble fragment on aggregation of Jurkat cells and IL-2 production;

FIG. 18 shows PEG moieties used in preparation of PEG-conjugated forms of a Bst2 soluble fragment;

FIG. 20 shows the expression and distribution of Bst2 in inflammation-associated diseases.

FIGS. 22A-22D show representative vector maps of Bst2 decoy-IgG Fc fusion proteins of FIG. 21.

FIGS. 30A-30B show anti-Bst2/Damp1 monoclonal antibody. (A) Heavy chain variable regions (SEQ ID NOS:149-159); and (B) kappa chain variable regions (SEQ ID NOS: 160-171). CDR1, CDR2 and CDR3 regions are boxed as well as indicated by asterisks.

FIGS. 31A-31B show anti-Bst2 monoclonal antibodies transiently expressed and purified on a PAGE gel. (A) under non-reducing conditions; (B) under reducing conditions.

DETAILED DESCRIPTION OF THE PREFERRED EMBODIMENTS

Figure 1:
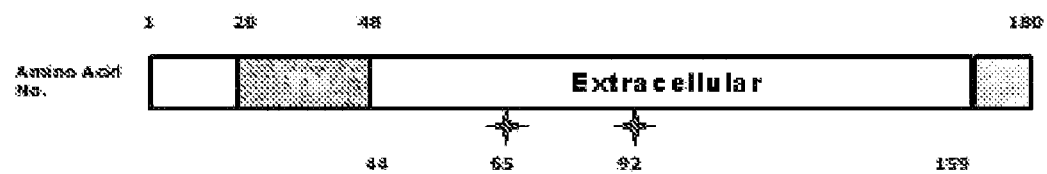
FIG. 1 is an amino acid sequence alignment showing sequence similarity between human Bst2 (SEQ ID NO: 3) and mouse Damp1 (SEQ ID NO: 4)

In the present application, "a" and "an" are used to refer to both single and a plurality of objects.

As used herein, "antagonist" or "blocker" refers to a substance that inhibits, blocks or reduces the activity of a protein that induces inflammation. The action mechanism of the antagonist is not specifically limited. Examples of the antagonist include organic or inorganic compounds; polymeric compounds, such as proteins, carbohydrates and lipids; and composites of multiple compounds. For example, a "Bst2 antagonist" or "Bst2 blocker" may include a substance that inhibits, blocks or reduces the activity of Bst2 protein in its activity in inducing inflammation.

As used herein, "variant" refers to a protein or a fragment thereof, which has a sequence different from a native amino acid sequence of a protein, by a deletion, an insertion, a non-conservative or conservative substitution or a combination thereof. For example, amino acid exchanges in proteins and peptides which do not generally alter the activity of the proteins or peptides are known in the art (H. Neurath, R. L. Hill, The Proteins, Academic Press, New York, 1979). The most commonly occurring exchanges are Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu and Asp/Gly, in both directions.

The term "vector", as used herein, which describes a vector capable of expressing a protein of interest in a suitable host cell, refers to a genetic construct that comprises essential regulatory elements to which a gene insert is operably linked in such a manner as to be expressed in a host cell.

The term "operably linked", as used herein, refers to a functional linkage between a nucleic acid expression control sequence and a second nucleic acid sequence coding for a target protein in such a manner as to allow general functions. For example, a promoter may be operably linked to a nucleic acid sequence coding for a protein and affect the expression of the coding sequence. The operable linkage to a vector may be prepared using a genetic recombinant technique well known in the art, and site-specific DNA cleavage and ligation may be achieved using enzymes generally known in the art.

The term "modification", as used herein, indicates a process in which a peptide or a non-peptide polymer is linked to Bst2 protein, Damp1, or a fragment thereof.

The term "non-peptide polymer", as used herein, refers to a biocompatible polymer in which two or more repeating units are linked to each other. Examples of the non-peptide polymer include polyethylene glycol (PEG), polypropylene glycol (PPG), co-poly (ethylene/propylene) glycol, polyoxyethylene (POE), polyurethane, polyphosphazene, polysaccharide, dextran, polyvinyl alcohol, polyvinyl pyrrolidone, polyvinyl ethyl ether, polyacryl amide, polyacrylate, polycyanoacrylate, lipid polymer, chitins, hyaluronic acid, and heparin. A preferred non-peptide polymer is polyethylene glycol.

The term "siRNA", as used herein, refers to a short double-stranded RNA molecule that is able to induce RNA interference (RNAi) through cleavage of the target mRNA. The term "specific" or "specific to", as used herein, means an ability to suppress only a target gene while not affecting other genes in cells. In the present invention, siRNA molecules specific to Bst2 are provided.

The term "prevention", as used herein, means all activities that inhibit inflammatory diseases or delay incidence of inflammatory diseases through administration of the composition. The term "treatment", as used herein, refers to all activities that alleviate and beneficially affect inflammatory diseases.

The term "inflammatory diseases", as used herein, refers to all diseases that result from the body's defense responses or infectious responses against harmful influences in states (physical, chemical and biological states) of having symptoms such as redness, swelling, tenderness, pain, fever and dysfunction.

As used herein, "Bst2 ligand" or "Bst L" refers to the molecule that specifically binds to Bst2.

Bst2 Protein

Bst2 participates in intercellular adhesion during inflammation. In one aspect, the present invention provides antagonists of Bst2 (Bone marrow Stromal Antigen-2) protein so as to prevent intercellular adhesion of immune cells to the endothelial cells or with each other during inflammation.

The present inventors, through studies using (1) a homotypic aggregation model of human U937 monocytic cells to investigate the effect of Bst2 on aggregation of immune cells, (2) a heterotypic aggregation model between U937 cells and HUVEC cells to investigate the effect of Bst2 on intercellular adhesion between immune cells and endothelial cells, (3) a Jurkat T-cell model to investigate the effect of Bst2 on T lymphocyte activation, found that Bst2 protein participates in an inflammation process in which lymphocytes migrate to the site of inflammation, recognize extracellular matrix components to interact with cells, and adhere to the cells. The present inventors further found that an antagonist of Bst2 protein effectively inhibits such intercellular adhesion and is thus able to effectively treat inflammatory diseases.

The Bst2 protein was initially identified in bone marrow stromal cells and is considered to be involved in the differentiation and proliferation of cells. A cDNA encoding Bst2 was cloned in 1995, and the BST-2 gene was found to be located on human chromosome 19p13.2 [Ishikawa et al., *Genomics* 26:527-534, 1995]. The Bst2 gene consists of five exons and four introns. Bst2 is a 30- to 36-kD type II transmembrane protein consisting of 180 amino acids [Ohtomo et al., *Biochem. Biophys. Res. Commun.* 258:583-591, 1999]. Damp1 gene, a mouse homologue of human Bst2 gene, has 45% DNA sequence identity to the human Bst2 gene, and as shown in FIG. 1, has less than 40% amino acid sequence similarity to human Bst2. The Bst2 protein is predominantly expressed in the liver, lung, heart and placenta, and in lower levels in the pancreas, kidneys, skeletal muscle and brain. BST-2 surface expression on fibroblast cells accelerates the stromal cell-dependent growth of murine bone marrow-derived pre-B cells. This result suggests that Bst2 regulates pre-B-cell growth or plays a critical role in B cell activation in rheumatoid arthritis. Bst2 is also overexpressed in some types of cancer, including oral cancer, breast cancer, adenoma and cervical cancer.

With respect to Bst2 protein, the isolation and expression of a gene encoding Bst2 protein (EP1033401), and the use of the Bst2 protein in cancer diagnosis (WO01/57207 and WO01/51513) have been reported. The Bst2 protein is divided into three domains: cytoplasmic, transmembrane and extracellular domains, and an intracellular domain contains cytoplasmic and transmembrane domains.

Inflammatory Diseases

The present inventive composition may be used for preventing or treating all types of inflammatory diseases induced by Bst2 expression. In fact, Bst2 has been identified to be overexpressed in various inflammatory diseases including atherosclerosis, rheumatoid arthritis, asthma, sepsis, ulcerative colitis, multiple sclerosis, acute myocardial infarction, heart attack, psoriasis, contact dermatitis, osteoarthritis, rhinitis, Crohn's disease and autoimmune diseases.

The present composition may be administered in a pharmaceutically effective amount. The term "pharmaceutically effective amount", as used herein, refers to an amount sufficient for treatment of diseases, which is commensurate with a reasonable benefit/risk ratio applicable for medical treatment. An effective dosage amount of the composition may be determined depending on the type of disease, severity of the illness, the patient's age and gender, drug activity, drug sensitivity, administration time, administration routes, excretion rates of a drug, duration of treatment, drugs used in combination with the composition; and other factors known in medical fields. The present composition may be administered as individual therapeutic agents or in combination with other therapeutic agents, and may be administered sequentially or simultaneously with conventional therapeutic agents. This administration may be single or multiple dosing. Taking all factors into consideration, it is important to conduct administration with a minimum of doses capable of giving the greatest effects with no adverse effects, and the doses may be readily determined by those skilled in the art.

Bst2 Decoy

Damp1 decoy has similar activity to Bst2. Therefore, in this application, whenever mention is made of Bst2 decoy, modified Bst2, fragment or variant thereof, its mouse analog, Damp1 is to be considered within the same scheme. It is understood that in certain aspects of the invention, mouse Damp1 may be used in place of Bst2 and they may be used interchangeably. For instance, when Bst2 decoy is used, it is also contemplated that Damp1 decoy may be used, including any chimera of Damp1 decoy. It is also contemplated that Damp1 and its variants may be used for treatment of inflammation along with Bst2. Accordingly, it is understood that any specific usage of Bst2 indicated in this application applies to Damp1 as well and may be claimed in the same manner.

Any soluble form of Bst2 protein or a fragment or variant thereof can be used as a decoy that binds competitively to a molecule or a site to which an immune cell expressing Bst2 would bind to induce inflammation. The Bst2 fragment used as a decoy is not specifically limited so long as it has an inflammation-suppressing effect by inhibiting intercellular adhesion, but is preferably a Bst2 protein having a deletion of the whole or a portion of the intracellular domain. In an exemplified embodiment, the Bst2 protein fragment is a Bst2 protein fragment comprising the amino acid sequence of SEQ ID NO:3. The Damp1 protein fragment is a Damp1 protein fragment comprising the amino acid sequence of SEQ ID NO:4. The Bst2 protein fragment and Damp1 protein fragment were found to effectively inhibit the intercellular adhesion induced by Bst2.

The scope of the present invention includes protein having a native amino acid sequence of the Bst2 protein or a fragment or variant thereof, and DNA and RNA capable of encoding such protein, that has an inflammation-suppressing effect by inhibiting intercellular adhesion and signaling.

In addition, the protein or fragment thereof, provided in the present invention, may be in the form of having native sugar chains, increased sugar chains compared to a native form or decreased sugar chains compared to the native form, or may be in a deglycosylated form. The increase, decrease or removal of sugar chains of the protein may be achieved by an ordinary method, such as a chemical method, an enzymatic method, or a genetic engineering method using a microorganism.

The scope of the present invention includes the methods of constructing the expression vectors for decoy Bst2 for expression in host cells of mammalian, insect or fungal origin and methods of purifying the Bst2 decoy protein. Expression vectors designed for decoy Bst2 expression in mammalian, insect (baculovirus) and fungal cells are constructed by inserting the DNA fragment encoding the decoy Bst2 adjacent to the host cell-specific promoter in a host cell-specific vector, which can be in a plasmid or viral form. The decoy protein may be expressed as a tagged fusion protein in mammalian, insect or fungal cells. Tags are short protein sequences, which have high binding affinity to antibodies or specially modified solid supports. The tags may include but not restricted to Histidine, Flag, V5, GST and HA tags. Tagged Bst2 decoy is purified based on the affinity of the tag to the solid support such as columns or beads. Additional steps including liquid chromatography may be used to increase the purity of Bst2 decoy protein.

The protein or fragment, if desired, may be modified by phosphorylation, sulfation, acrylation, methylation, farnesylation, and the like.

Variants of Bst2 decoy include a functional equivalent exerting substantially the same activity as the native form or a protein having a modification enhancing or reducing physical and chemical properties. Preferred is a variant having a modified physicochemical property. For example, the variant has enhanced structural stability against external environments including physical factors, such as temperature, humidity, pH, electrolytes, reducing sugars, pressure, dryness, freezing, interfacial tension, light, repeated freezing and thawing, high concentrations, and the like; and chemical factors, such as acids, alkalis, neutral salts, organic solvents, metal ions, oxidizing and reducing agents, proteases, and the like.

The Bst2 protein, a fragment thereof, or a variant thereof, which has an inflammation-suppressing effect by inhibiting intercellular adhesion, may be naturally isolated or synthesized (Merrifield, J. Amer. Chem. Soc., 85:2149-2156, 1963), or may be prepared by a recombination method based on DNA sequence (Sambrook et. al., Molecular Cloning, Cold Spring Harbor Laboratory Press, New York, USA, 2nd Ed., 1989). When a genetic recombination technique is used, a desired protein may be obtained by inserting a nucleic acid encoding the Bst2 protein, a fragment thereof or a variant thereof into a suitable expression vector, transforming a host cell with the expression vector, culturing the host cell to express the desired protein, and recovering the produced protein from the culture.

The Bst2 protein or a fragment thereof, provided in the present invention, which has an inflammation-suppressing effect by inhibiting intercellular adhesion or interaction and immune cell activation, may be in a monomeric or multimeric form. A multimer may be formed by various methods commonly known in the art, and the method for forming a multimer is not specifically limited. For example, a multimer may be prepared using a sequence inducing multimer formation, for example, isoleucine zipper (ILZ) sequence inducing trimer formation, or surfactant protein-D (SP-D) inducing dodecamer formation. Otherwise, a multimer may be prepared by conjugating two or more polypeptides, which each have been produced in a monomeric form, for example, using a linker.

The Bst2 protein, or fragment thereof, which has an inflammation-suppressing effect by inhibiting intercellular adhesion, or interaction and immune cell activation, may be modified by a non-peptide polymer.

In a further detailed aspect, the antagonist includes non-peptide polymer-modified Bst2 protein or a fragment thereof, which has an inflammation-suppressing effect by inhibiting intercellular adhesion or interaction and immune cell activation.

The linkage of the Bst2 protein, or fragments thereof with a non-peptide polymer include covalent bonds and all types of non-covalent bonds, such as hydrogen bonds, ionic interactions, van der Waals forces and hydrophobic interactions. Preferably, the polymer is linked with a protein through a specific reactive group. Examples of reactive groups of the polymer include an aldehyde group, a propionic aldehyde group, a butyl aldehyde group, a maleimide group, a ketone group, a vinyl sulfone group, a thiol group, a hydrazide group, a carbonyldimidazole (CDI) group, a nitrophenyl carbonate (NPC) group, a trysylate group, an isocyanate group, and succinimide derivatives. The non-peptide polymer reacts with reactive groups of a polypeptide, for example, an N-terminus, a C-terminus or/and side chain of amino acid residues (e.g., side chain of a lysine residue, a histidine residue or a cysteine residue).

The Bst2 protein, which has an inflammation-suppressing effect by inhibiting intercellular adhesion, or interaction and immune cell activation, may be linked with a non-peptide polymer in a molar ratio of 1:1 to 1:10, preferably 1:1 to 1:2. When the Bst2 protein, or fragment thereof, is modified by two or more non-peptide polymers, the non-peptide polymers are identical or different. The proteins may have improved in vivo stability and metabolism through modification with non-peptide polymers.

In still another aspect, the present invention provides a composition for preventing or treating inflammatory diseases, comprising one or more selected from among, as described above, Bst2 protein or a fragment thereof having an inflammation-suppressing effect by inhibiting intercellular adhesion or interaction and immune cell activation; non-peptide polymer-modified Bst2 protein or a fragment thereof having an inflammation-suppressing effect by inhibiting intercellular adhesion.

The present composition may be applied to humans, as well as to livestock whose inflammatory diseases can be inhibited or reduced by administration of Bst2, such as bovine, horses, sheep, swine, goats, camels, antelopes, dogs and cats. In this context, the present inventors found that human Bst2 and mouse Damp1 have functional similarity and act on cells having the same origin as well as a different origin.

In still another detailed aspect, the present invention relates to a method of preventing or treating inflammatory diseases, comprising administering to a patient one or more proteins selected from among Bst2 protein or a fragment thereof having an inflammation-suppressing effect by inhibiting intercellular adhesion.

Decoy Protein Stabilization By Fc Fusion

Fusion of the decoy Bst2 to the Fc portion of an antibody is described. The resulting fusion was able to prolong the therapeutic effect of the decoy Bst2 protein allowing for a more favorable dosing schedule. Fusion to albumin has also been shown to extend serum half life of small proteins. Like fusion of Bst2 decoy to the Fc portion of an antibody, fusion of Bst2 decoy to albumin may increase the serum half-life of Bst2 decoy.

Many potential therapeutic proteins including the Bst2 decoy are smaller than 40 kDa and therefore susceptible to renal clearance by glomerular filtration. The redesign of proteins to promote longer serum half-life is an important medical and commercial goal. Since proteins must generally be administered by injection, it is preferable to have therapeutic proteins that minimize the frequency of protein administration.

In general, a protein's effective molecular weight may be increased by fusion to a heterologous carrier protein, such as to albumin or the Fc region of an antibody which may aid in purification of the protein (Capon D J, Chamow S M, Mordenti J, Marsters S A, Gregory T, Mitsuya H, Byrn R A, Lucas C, Wurm F M, Groopman J E, et al. Nature. 1989 February 9;337(6207):525-31; Yeh P. et al. Proc. Natl. Acad. Sci. USA, 89:1904-1908, 1992). The heterologous sequence could be any sequence as long as it allows the resulting chimeric protein to retain one of the biological activities of the Bst2 decoy.

Bst2 is thought to exist as a homodimer on the cell surface (Ohtomo T, Sugamata Y, Ozaki Y, Ono K, Yoshimura Y, Kawai S, Koishihara Y, Ozaki S, Kosaka M, Hirano T, Tsuchiya M, Biochem Biophys Res Commun. 1999, 258(3):583-91). It is also thought that Bst2 requires dimerization for its activity. Thus, heterologous sequences which promote association of the Bst2 decoy monomers to form dimers, trimers and higher multimeric forms are preferred. The construction of an Fc chimeric protein using a small protein with a molecular weight of less than 40 kDa results in a dramatic extension of serum half-life (Lo K M, Zhang J and Gillies S D, PCT WO00/40615, 2000). Bst2 decoy-Fc is a recombinant chimeric fusion protein consisting of the extracellular domain of human Bst2 and the Fc region of human IgG. Bst2 decoy-Fc was produced as a dimer and to some extent as a higher multimer.

Monoclonal Antibody to Bst2

The use of immune therapy has become popular recently in cases where the protein target of a disease has been determined. The highly specific targeting allowed by therapeutic antibodies results in virtually no side effects, even at relatively high doses. This also makes use of the antibodies' naturally inherent serum stability, providing the basis for a long-acting therapeutic molecule.

Antibody therapeutics generally falls into one of two categories that are not mutually exclusive. The first category is dependent on the variable region (target protein recognition portion) of the antibody. The specific epitope recognized by the antibody will allow the antibody to inhibit the binding of the target protein with other proteins (inhibitory or antagonistic effect) interfering with cell-cell interactions or terminating signal transduction through the target protein, or generate an artificial signal as a result of its binding with the target protein in the absence of a required secondary protein (activation or agonistic effect) as is the case of dimerization-dependent receptor signaling or receptor-dependent ligand mimicking. The second category depends on the constant region (Fc portion) of the antibody, that determines which, if any, immune effector functions will become activated as a result of the binding of the Fc portion of the antibody with its cognate Fc receptor present on the immune effector cells. The presence of a specific target protein on the surface of a target cell targets that cell for destruction by an effector function.

By developing an antibody that is highly specific for Bst2, a therapeutic antibody has been created that shares many of the characteristics of the decoy Bst2 molecule, in that it is capable of interfering with cell-cell adhesion and acting as a therapeutic protein in inhibiting disease-specific inflammatory response.

In certain cases that deal with the pathogenic mechanisms of the mucosal immune system, antibodies may be administered orally or nasally. The mucosal immune system is unique, as tolerance is preferentially induced after exposure to antigen, and induction of regulatory T cells is a primary mechanism of oral tolerance. Orally administered antibody can be rapidly taken up by the gut-associated lymphoid tissue (GALT), where it exerts its immunologic effects. Oral administration of antibody can signal T cells in the gut in a fashion that delivers a weak but effective signal in enhancing the regulatory function of T cells. Oral administration of CD3 specific antibody has been demonstrated in experimental autoimmune encephalitis (EAE) model. These studies showed that the Fc portion of the CD3-specific antibody was not required. An orally administered F(ab')2 fragment of CD3-specific antibody suppressed EAE.

Conventional IgG antibodies are bivalent with the ability to bind to two antigens. This ability greatly increases their functional affinity and confers high retention time on many cell surface receptors and antigens. Anti-Bst2 antibodies that inhibit immune, inflammatory responses may exist in many different antibody formats.

1. The anti-Bst2 antibodies of the invention may be humanized monoclonal antibodies or human monoclonal antibodies. An entirely antigenic murine mAb becomes human friendly when small parts of the murine antibodies are engrafted onto human immunoglobulin molecules creating either chimeric antibodies where only the Fc part of the immunoglobulin molecule is human, or humanized antibodies where only the complementarity determining regions (CDR) of the immunoglobulin are murine and 90 to 95% of the molecule is human. In one respect, fully human monoclonal antibodies may be generated in transgenic mice by employing the HuMAb-Mouse (GenPharm-Medarex) or XENOMOUSE® (Abgenix, Inc.) technology. Humanized antibodies include human immunoglobulins in which residues from a CDR of the recipient are replaced by residues from a CDR of a non-human species such as mouse, rat or rabbit having the desired specificity, affinity and biological function.

Human antibodies also can be produced using techniques such as phage display libraries (Hoogenboom and Winter, J. Mol. Biol, 1991, 227:381, Marks et al., J. Mol. Biol. 1991, 222:581). Methods for humanizing non-human antibodies are well known. Humanization can be performed following the method of Winter et al. (Jones et al., Nature, 1986, 321:522; Riechmann et al., Nature, 1988, 332:323; Verhoeyen et al., Science, 1988, 239:1534) by substituting rodent CDR sequences or CDRs for the corresponding sequences of a human antibody. Such humanized antibodies are chimeric antibodies (U.S. Pat. No. 4,816,567). Typically, humanized antibodies are antibodies where CDR residues are substituted by residues from analogous sites in rodent antibodies.

2. The anti-Bst2 antibodies of the invention may be bispecific antibodies. Bispecific antibodies are monoclonal antibodies, preferably human or humanized antibodies that have dual-targeting specificities. Bispecific antibodies are derived from the recombination of variable domains of two antibodies with different specificities; Bispecific antibodies are thus capable of binding both antigens of their parental antibodies. In the case of Bst2, one of the binding specificities could be for Bst2 and the other may be for Bst2 L, or any other cell surface protein.

Methods for making bispecific antibodies are well known (Traunecker et al., EMBO J, 1991, 10:3655; WO 93/08829; Suresh et al., Methods in Enzymology, 1986, 121:210; Milstein and Cuello, 1983, Nature, 305:537). Briefly, antibody variable domains with the desired binding specificities are fused to immunoglobulin constant domain. This fusion contains an immunoglobulin heavy-chain constant domain (part of the hinge, CH2 and CH3 regions) and preferably contains the first heavy chain constant region (CH1). DNAs encoding the immunoglobulin heavy chain fusions and the immunoglobulin light chain are inserted into separate expression vectors and are cotransfected.

3. The anti-Bst2 antibodies of the invention may be single-chain variable fragment antibody (scFV). Recombinant approaches have led to the development of single chain variable fragment antibody (scFv). A monomeric scFv has a molecular mass of only about 30 kDa, which is expressed in a variety of systems as a single VL-VH pair linked by a Gly/Ser-rich synthetic linker (Berezov A. et al., 2001, J Med Chem 44:2565). When expressed in bacteria or eukaryotic cells, the scFv folds into a conformation similar to the corresponding region of the parental antibody. It was shown to retain comparable affinity to that of a Fab (Kortt et al., 1994, Eur J Biochem 221:151). ScFvs are amenable to various genetic modifications such as humanization and the production of fusion proteins to enhance their potential as therapeutic agents. For example, Pexelizumab, a humanized scFv that binds to the C5 component of complement has been shown to reduce myocardial infarctions during coronary artery bypass graft surgery (Varrier et al., 2004, JAMA 291:2319).

ScFvs of different specificity can also be linked together to produce bispecific antibodies that bind two different receptors on single or different cells. In the case of Bst2, it could be bispecific antibody-like molecules with an anti-Bst2 scFv and anti-Bst2 L scFv, or with anti-Bst2 scFv and any other cell surface proteins.

Phage display method may be used to produce anti-Bst2 scFv. In this method, large repertoires of antibody variable region cDNAs are collected from the B cells and combinations of VHs and VLs are expressed in the form of scFvs on the surface of filamentous bacteriophage. The phages that express scFvs are to be panned from antigen-coated plates. The affinity of the anti-Bst2 scFv may be improved by mutating the CDRs of the construct and then repeating the panning procedure.

4. The anti-Bst2 antibodies of the invention may be Fab, Fab2 bispecific antibodies, Fab3 trispecific antibodies, bivalent minibody, trivalent triabody, or tetravalent tetrabodies.

5. The anti-Bst2 antibodies of the invention may be monoclonal antibodies. Monoclonal antibodies are prepared using hybridoma methods, such as those described by Kohler and Milstein (Nature, 1975, 256:495). Mouse, rat, hamster or other host animals, is immunized with an immunizing agent to generate lymphocytes that produce antibodies with binding specificity to the immunizing antigen. In an alternative approach, the lymphocytes may be immunized in vitro.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. The following examples are offered by way of illustration of the present invention, and not by way of limitation.

EXAMPLES

Example 1

Cell Culture

A human monocytic cell line U937 (ATCC, U.S; Cat. CRL-1593.2) was suspension-cultured in RPMI-1640 (Gibco-BRL) supplemented with 10% fetal bovine serum (FBS; Gibco-BRL), 100 U/ml of penicillin (Gibco-BRL) and 100 µg/ml of streptomycin (Gibco-BRL) at 37° C. under a 5% $CO_2$ atmosphere.

Human umbilical vein endothelium cell line HUVEC (Cambrex, U.S.; Cat. CC-2517A) was subcultured in EGM-2 medium (Cambrex, U.S.) supplemented with 10% FBS at 37° C. under a 5% $CO_2$ atmosphere. In the following examples, cells were pretreated with 0.5% FBS, instead of 10% FBS, for 16 hrs. According to given conditions, cells were pretreated with human recombinant interferon-gamma (10 ng/ml, Cambiochem, U.S.) and PMA (1 ng/ml, Cambiochem) or a medium for a predetermined period of time.

A mouse monocytic cell line WEHI-274.1 (ATCC, Cat. CRL-1679), and a mouse endothelial cell line, SVEC 4-10 (ATCC, Cat. CRL-2181), were cultured and pretreated according to the same method as in the human cell lines.

A human T-lymphocyte cell line Jurkat (ATCC, TIB152 clone) was suspension-cultured in RPMI-1640 (Gibco-BRL) supplemented with 10% FBS, 100 U/ml of penicillin and 100 µg/ml of streptomycin at 37° C. under a 5% $CO_2$ atmosphere.

Protein expression and purification were carried out using CHO—S cells (Invitrogen, Cat. 11619-012). CHO—S cells were suspension-cultured in F12/HAM (Gibco-BRL) medium supplemented with 10% FBS, 100 U/ml of penicillin and 100 µg/ml of streptomycin at 37° C. under 5% $CO_2$ atmosphere.

Example 2

Cloning of Human Bst2 Gene and Mouse Damp1 Gene

An expression vector of histidine-tagged Bst2 was constructed as follows. Full-length cDNA (NM004335; SEQ ID NO:1) of human Bst2 gene was synthesized by Origene Technologies (USA), and amplified by PCR using Pfu ultra HF DNA polymerase (Stratagene) in a volume of 50 µl. A PCR product was cloned into a pCMV HA vector (Clontech) using SalI and NotI.

Vectors for expressing soluble fragments of Bst2 and Damp1 were constructed as follows. FIG. 2 shows the locations of PCR primers (SEQ ID NOS:16-24) used in cloning the soluble fragments. A DNA fragment coding for the extracellular region of human Bst2 protein was obtained by PCR, and was fused at the N-terminus to a signal sequence P of tPA (tissue Plasminogen activator) to promote extracellular secretion after being expressed. The DNA fragment was also fused at the C-terminus to a six-histidine tag to facilitate determination of protein expression levels and protein purification. The Bst2 soluble fragment did not contain 11 amino acid residues at the C-terminus and also did not contain the transmembrane and cytoplasmic domains. The PCR product was treated with a final concentration of 0.8% dimethyl sulfoxide (DMSO; Sigma), digested with BamHI and XbaI, and cloned into a pcDNA 3.1 vector (Invitrogen).

Full-length cDNA (NM 198095; SEQ ID NO:2) of mouse Damp1 gene was obtained by RT-PCR using mRNA isolated from mouse liver. A RT-PCR product was digested with BamHI and XbaI and cloned into pcDNA 3.1 (Invitrogen). A soluble fragment region was determined by amino acid sequence homology analysis between human Bst2 and mouse Damp1. As a result, a vector expressing the soluble Bst2 fragment of SEQ ID NO:3 and another vector expressing the soluble Damp1 fragment of SEQ ID NO:4 were obtained.

Example 3

Real-time Quantitative RT-PCR

Intracellular expression levels of specific genes were analyzed by real-time quantitative RT-PCR using ABI PRISM® 7900HT (Applied Biosystems, Foster City, Calif.) and a SYBR-Green assay kit. Primers and probes used were designed using PRIMER EXPRESS® software (Applied Biosystems).

10 ng of single-stranded cDNA was placed in a reaction tube and subjected to multiplex TAQMAN® PCR (50 µl) using the TAQMAN® Universal PCR Master Mix. The relative amount of target cDNA was calculated using the comparative cycle threshold (CT) method. PCR products were analyzed by agarose gel electrophoresis.

The relative levels of a specific gene A were expressed as a change compared to a control sample (untransfected cells). All values were obtained using a 2-CT ($C_{t1}-C_{t0}$, $C_{t1}=C_{t1A}-C_{t1B}$, $C_{t0}=C_{t0A}$-Ct0B) calculation method relative to a normalization gene B (human GAPDH gene) in transfected cells. Each value was obtained from each sample in triplicate. The above experiments were carried out to quantify the expression of the Bst2 gene and interleukin-2.

Example 4

Expression and Purification of Soluble Bst2 Protein Fragment or Damp1 Protein Fragment In order to express the above-prepared soluble Bst2 protein fragment or Damp1 protein fragment, a vector DNA was transiently or permanently introduced into specific animal cells. Transient transfection was performed by calcium phosphate ($CaPO_4$) precipitation, as follows. 24 hrs before transfection, $7\times10^6$ 293T cells (ATCC) were seeded onto a 150-mm cell culture plate and cultured. One hour before transfection, the culture medium was exchanged with IMDM medium (Cambrex) supplemented with 2% fetal bovine serum (FBS; GIBCO-BRL). 1.5 ml of TE buffer (1 mM Tris, 0.1 mM EDTA, pH 8.0) containing 75 µg of DNA and 250 mM calcium was mixed with 1.5 ml of HEPES buffer (50 mM HEPES, 140 mM NaCl, 1.4 mM $Na_2HPO_4$, pH 7.05), was incubated for about 1 min at room temperature, and was applied to the pre-cultured cells. The cells were incubated in a $CO_2$ incubator at 37° C. for 6 hrs. After the DNA/calcium solution was removed, the cells were re-fed with serum-free medium and further cultured for 72 hrs or longer, and the culture medium was then recovered. Separately, a permanent cell line was established using lipofectamine and dihydrofolate reductase as a selectable marker, as follows. 48 hrs before transfection, $1.35\times10^6$ CHO-DUKX-B11 (dhfr$^-$) cells (ATCC) were seeded onto a 100-mm cell culture plate and cultured in IMDM medium complemented with 10% FBS. 0.6 ml of serum-free IMDM medium containing 18 µg of DNA was mixed with 0.6 ml of serum-free IMDM medium containing 54 µl of Lipofectamine 2000 (Invitrogen), and was incubated at room temperature for 45 min. The DNA/lipofectamine mixture was supplemented with 8.8 ml of serum-free IMDM medium and applied to the pre-cultured cells. The cells were incubated in a $CO_2$ incubator at 37° C. for 6 hrs. The medium was exchanged with a selection medium, 10% dialyzed FBS-containing IMDM medium. To analyze the transiently expressed protein, the cells were further cultured for 72 hrs or longer. The medium was then recovered and passed through a 0.2-µm filter (Millipore). The produced Bst2 soluble fragment protein was analyzed by immunoblotting using anti-Bst2 polyclonal antibody (Roche) or anti-histidine antibody (Roche).

For large-scale expression and purification of the soluble Bst2 protein fragment or Damp1 protein fragment, host cell lines into which a Bst2 or Damp1 expression vector was stably introduced were selected as production cell lines, as follows. CHO cells deleted in dihydrofolate reductase (DHFR) gene were transfected with an expression vector. Since the expression vector carried a dhfr gene, dihydrofolate reductase was used as a selectable marker. After 48 hrs, the transfected CHO cells were seeded onto a 96-well cell culture plate in a density of $1\times10^3$ cells/well and cultured in a medium containing 20 nM methotrexate (MTX) to amplify the DHFR gene. After two weeks, the medium was recovered and subjected to ELISA using anti-Bst2 antibody to compare clones for the expression levels of Bst2 soluble fragment protein. Clones exhibiting high expression levels were selected and exposed to gradually increased concentrations of MTX up to 300 nM to complete gene amplification. Thereafter, the medium was collected from each clone and subjected to ELISA and immunoblotting in order to finally select a production cell line exhibiting the highest protein expression levels. Since the Bst2 soluble fragment protein was produced in the culture medium under serum-free conditions, the expressed protein was purified from the collected medium using the six-histidine tag added to the C-terminus. Protein purification was performed by NTA chelating chromatography using a column, NTA chelating agarose CL-6B (Peptron Inc.). The purity of the purified protein was analyzed by electrophoresis and ELISA, and the amount of the purified protein was determined by a BCA method (Biorad, USA) and UV spectrophotometry.

Figure 3:
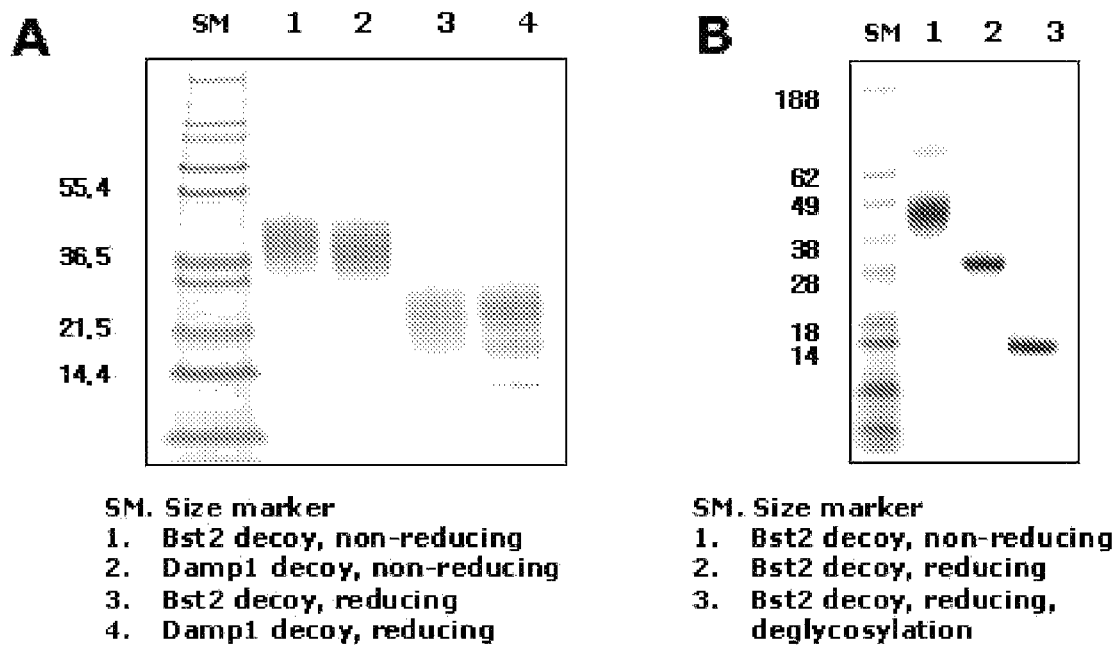
FIGS. 3A-3B show the results of electrophoresis analysis of a human Bst2 soluble fragment and a mouse Damp1 soluble fragment.

The human Bst2 soluble fragment and the mouse Damp1 soluble fragment, purified as described above, were analyzed by 4-20% SDS-PAGE (FIG. 3, panel A). The treatment of 1% dithiothreitol (DTT) and N-glycosidase F (Sigma) resulted in the Bst2 soluble fragment being a dimeric glycoprotein (FIG. 3, panel B). The results of the following examples were obtained using, among the prepared soluble fragments, a soluble Bst2 protein fragment having the amino acid sequence of SEQ ID NO:3 and a soluble Damp1 protein fragment having the amino acid sequence of SEQ ID NO:4.

Example 5

Evaluation of the Effect of Bst2 Protein on Homotypic Aggregation of U937 Cells

Example 5-1

Change in Expression Levels of Bst2 During Aggregation of U937 Cells

Expression levels of Bst2 protein were examined during aggregation of human U937 monocytic cells. $1\times10^6$ U937 cells were treated with PMA (2 ng/ml) and LPS (10 μg/ml) for 24 hrs to induce homotypic cell aggregation of U937 cells, and were observed for the degree of homotypic cell aggregation under a phase-contrast inverted microscope (Olympus 1X71, state, USA). To determine the degree of cell aggregation, the size of formed cell aggregates was measured as pixel intensity, using Adobe's Photoshop software, version 7.0. The standard deviation values shown in drawings were calculated from mean values of six randomly selected aggregates. Thereafter, all used cells were recovered, and total RNA was isolated and subjected to RT-PCR using a set of primers of SEQ ID NOS:5 and 6 to assess Bst2 expression levels.

```
Sense oligomer:
5'-TTTTCTCTTCTCAGTCTC-3'    (SEQ ID NO: 5)

Antisense oligomer:
5'-GCATCTACTTCGTATGAC-3'    (SEQ ID NO: 6)
```

Figure 4:
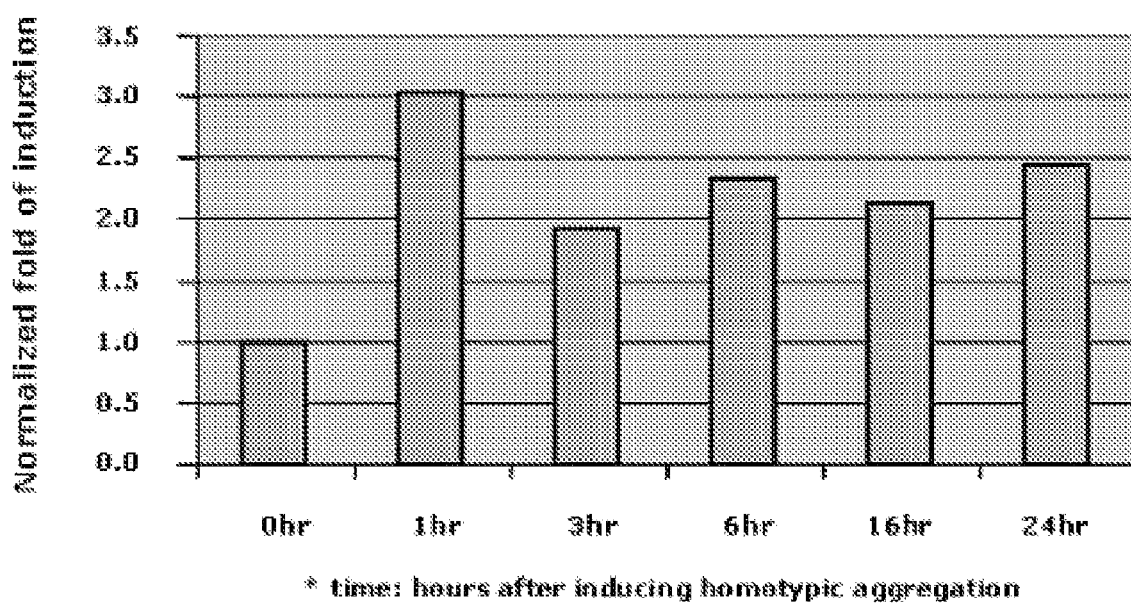
FIG. 4 shows the expression pattern of Bst2 gene during homotypic aggregation of U937 cells.

One hour after U937 cells were treated with PMA and LPS to induce homotypic aggregation, intracellular Bst2 expression increased by about three times. This increased level was maintained for 24 hrs. These results indicate that Bst2 gene expression increases during homotypic aggregation of U937 cells (FIG. 4).

Example 5-2

The Effect of Bst2 Protein on Homotypic Aggregation of U937 Cells

In order to determine whether the increased expression of Bst2 gene is essential for the homotypic aggregation of U937 cells, cell aggregation was assessed when Bst2 protein was overexpressed.

$1\times10^6$ U937 cells, which had been cultured under the aforementioned conditions, were seeded onto a 96-well cell culture plate (NUNC) and treated with PMA (2 ng/ml, Calbiochem) and LPS (10 μg/ml, Calbiochem) for 24 hrs. The cells were then observed for the degree of homotypic cell aggregation under a phase-contrast inverted microscope (Olympus 1X71, state, USA).

Figure 5:
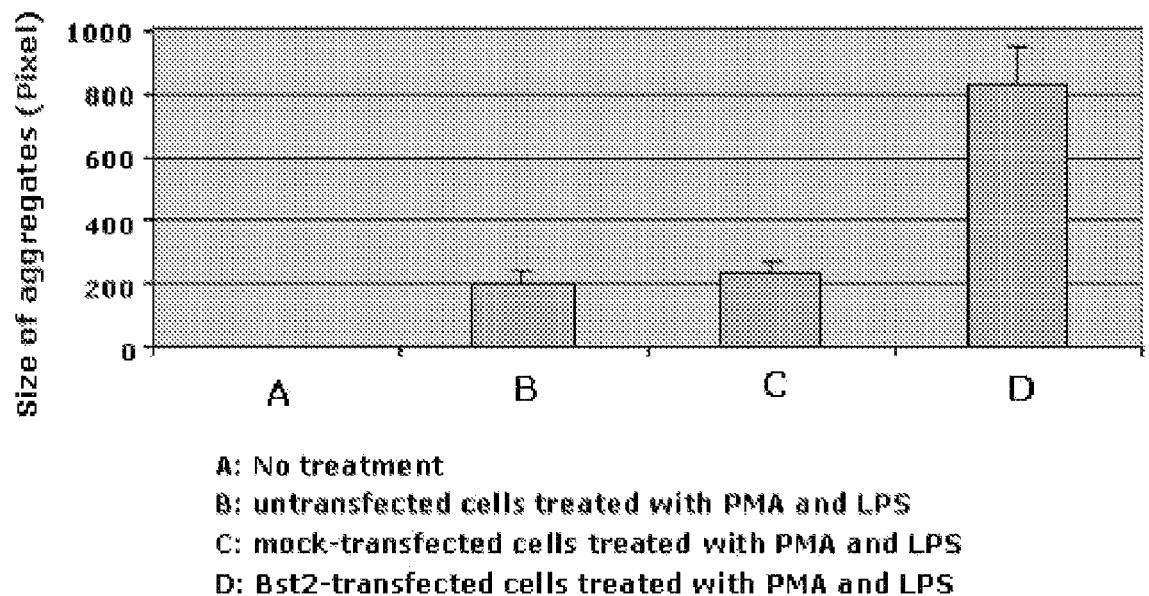
FIG. 5 shows the promoting effect of Bst2 overexpression on homotypic aggregation of U937 cells.

Bst2 protein itself did not induce aggregation of U937 cells, whereas the PMA/LPS treatment stimulated homotypic aggregation of U937 cells. Also, the transient overexpression of Bst2 increased homotypic aggregation of U937 cells by about four times (FIG. 5). These results indicate that Bst2 expression, while a sufficient condition, is not a requisite condition.

Example 5-3

Inhibition of Homotypic Aggregation of U937 Cells Using Bst2 Soluble Fragment In order to confirm whether the increased expression of Bst2 gene is essential for homotypic aggregation of U937 cells, cell aggregation was assessed when the action of Bst2 protein was suppressed.

Figure 6:
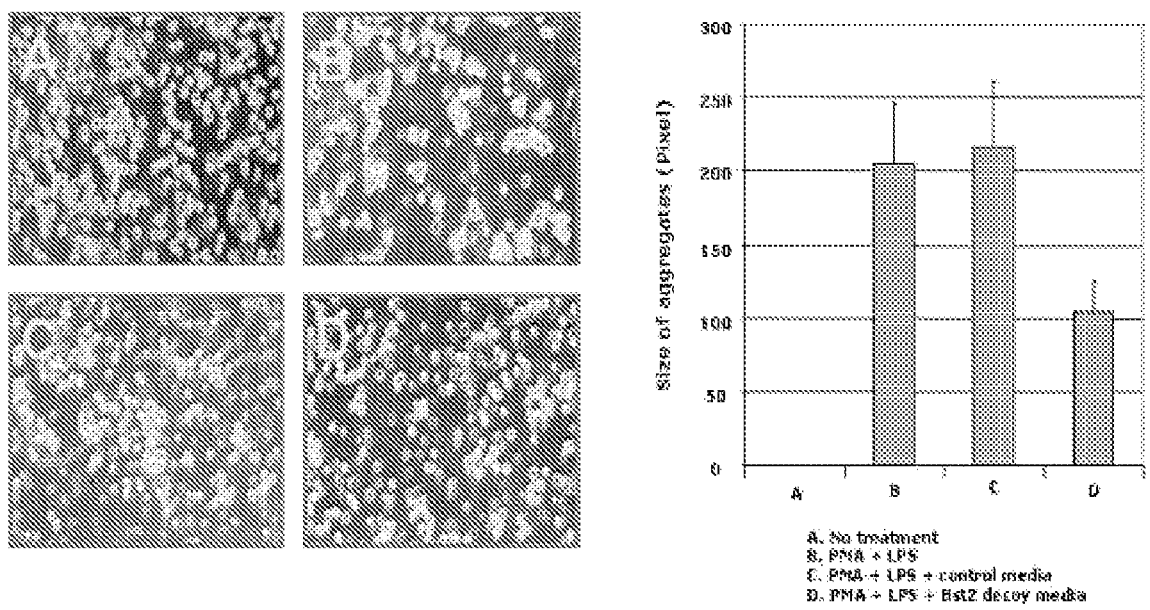
FIG. 6 shows the effect of a Bst2 soluble fragment on homotypic aggregation of U937 cells.

U937 cells were pretreated with PMA and LPS to induce cell aggregation, and were treated with serial dilutions of medium (decoy medium) containing a Bst2 soluble fragment transiently expressed in CHO—S cells. The Bst2 soluble fragment was found to decrease U937 cell aggregation induced by PMA and LPS by 50% in comparison with the culture (control medium) of CHO—S cells not expressing the Bst2 soluble fragment (FIG. 6). These results indicate that the Bst2 soluble fragment inhibits homotypic aggregation of U937 cells.

Example 6

Evaluation of the Effect of Bst2 Protein on Heterotypic Aggregation Between Two Different Cell Types

Example 6-1

Inhibition of Aggregation Between U937 and HUVEC Cells Using Bst2 Soluble Fragment HUVEC cells ($1\text{-}5\times10^4$ cells/ml) were seeded onto a 12-well cell culture plate. After one day, the medium was exchanged with a low-serum medium containing 0.5% FBS, and the cells were pretreated with interferon-gamma (IFN-ɣ; Calbiochem) in a final concentration 10 ng/ml for 24 hrs. Then, the pretreated HUVEC cells were co-cultured with U937 cells ($2\times10^6$ cells/ml, 500 μl) at 37° C. for 4 hrs. The co-culture was washed with phosphate buffer three or four times, and the remaining cells were fixed with 4% paraformaldehyde and microscopically observed.

Figure 8:
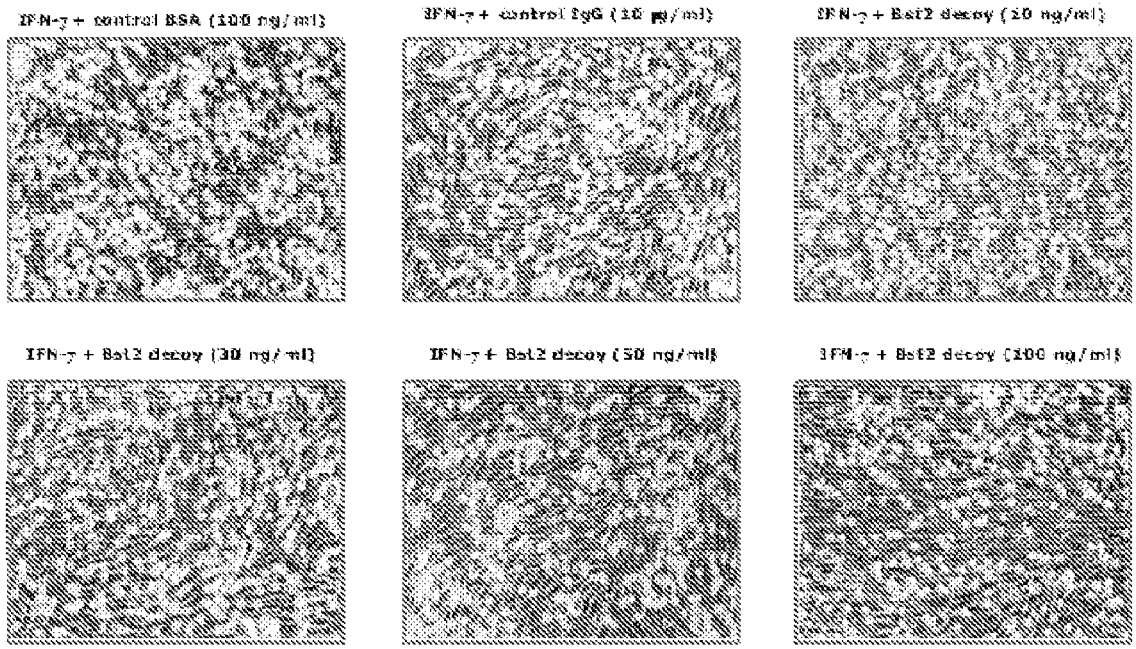
FIG. 8 shows the dose-dependent effect of a Bst2 soluble fragment on intercellular adhesion between HUVEC cells and U937 cells.

HUVEC cells not pretreated with IFN-ɣ did not bind to U937 cells. In contrast, IFN-ɣ-treated HUVEC cells bound to U937 cells and formed heterotypic cell aggregation. HUVEC cells treated with a Bst2 soluble fragment protein-containing medium, obtained form the culture pretreated with IFN-ɣ,, exhibited decreased aggregation with U937 cells. The treatment of a basic medium or albumin did not affect cell aggregation (FIG. 7). In FIG. 7, a "normal medium" indicates a FBS-containing general medium, and a "control medium" indicates a culture fluid of cells not expressing a Bst2 soluble fragment protein. In addition, the heterotypic cell aggregation was inhibited in such a manner of being dependent on concentrations of the Bst2 soluble fragment (FIG. 8).

The data presented herein indicate that Bst2 is important for inflammation and immunity. Blocking Bst2 function may reduce inflammation-induced diseases.

Example 6-2

Inhibition of Aggregation Between U937 and HUVEC Cells Using Bst2 siRNA

Various siRNA molecules acting in a Bst2-specific manner were constructed (QIAGEN). A total of 23 siRNA molecules specific to Bst2 were constructed. Each siRNA molecule consisted of an antisense RNA strand, complementary to Bst2 mRNA encoded by any one of the sequences of SEQ ID NOS:126-148, and a sense RNA strand complementary to the antisense RNA strand.

The test results below were obtained using siRNA consisting of an antisense RNA strand, complementary to Bst2 mRNA encoded by the sequence of SEQ ID NO:7, and a sense RNA strand complementary to the antisense RNA strand.

HUVEC cells were transfected with a siRNA molecule (HPP grade, QIAGEN) consisting of a sense strand and an antisense strand under the same conditions as described above, were treated with IFN-ɣ, and were assessed for aggregation with U937 cells.

```
Target sequence:
5'-AAGCGTGAGAATCGCGGACAA-3'        (SEQ ID NO: 7)

Sense oligomer:
5'-r(UUGUCCGCGAUUCUCACGC)d(TT)-3'  (SEQ ID NO: 8)

Antisense oligomer:
5'-r(GCGTGAGAATCGCGGACAA)d(TT)-3'  (SEQ ID NO: 9)
```

Figure 9:
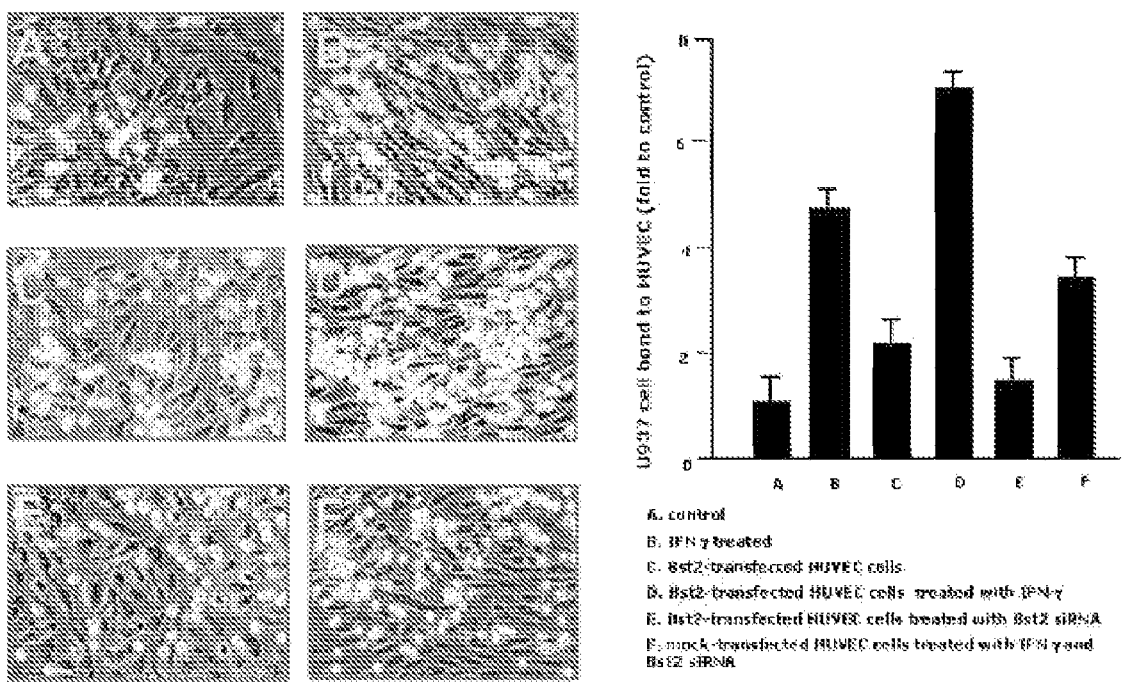
FIG. 9 shows the effect of Bst2 siRNA on intercellular adhesion between HUVEC cells and U937 cells.

Non-specific siRNA did not affect the heterotypic cell aggregation. In contrast, Bst2 gene-specific siRNA, unlike a control, completely inhibited aggregation between U937 cells and HUVEC cells (FIG. 9).

In order to determine whether Bst2 protein affects the adhesion of HUVEC cells to U937 cells, Bst2 protein was transiently overexpressed in HUVEC cells by transfection.

Figure 10:
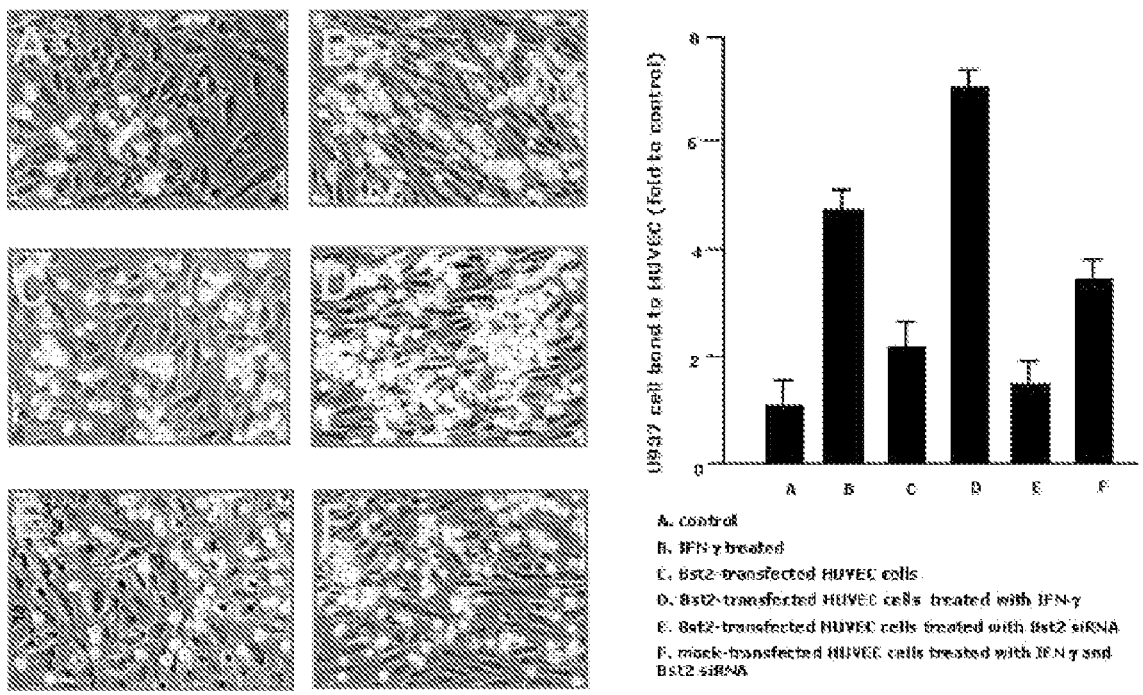
FIG. 10 shows the effect of Bst2 siRNA on intercellular adhesion between HUVEC cells and U937 cells upon Bst2 overexpression.

Quantitative analysis of heterotypic cell aggregation resulted in the finding that the increased expression of Bst2 protein increased aggregation by 50% or higher compared to a single treatment of IFN-ɣ. When Bst2 protein-overexpressed HUVEC cells were treated with siRNA of the Bst2 gene, heterotypic cell aggregation increased by Bst2 overexpression was inhibited again. These results indicate that Bst2 protein expression is important for heterotypic cell aggregation (FIG. 10).

Example 7

Evaluation of the Effect of Bst2 Protein on Homotypic Aggregation of T Lymphocytes and Activity of the Aggregation

Example 7-1

The effect of Bst2 Overexpression on Homotypic Aggregation of T Lymphocytes and IL-2 Production Human Jurkat T cells were induced to form homotypic cell aggregation and activated, as follows.

Figure 11:
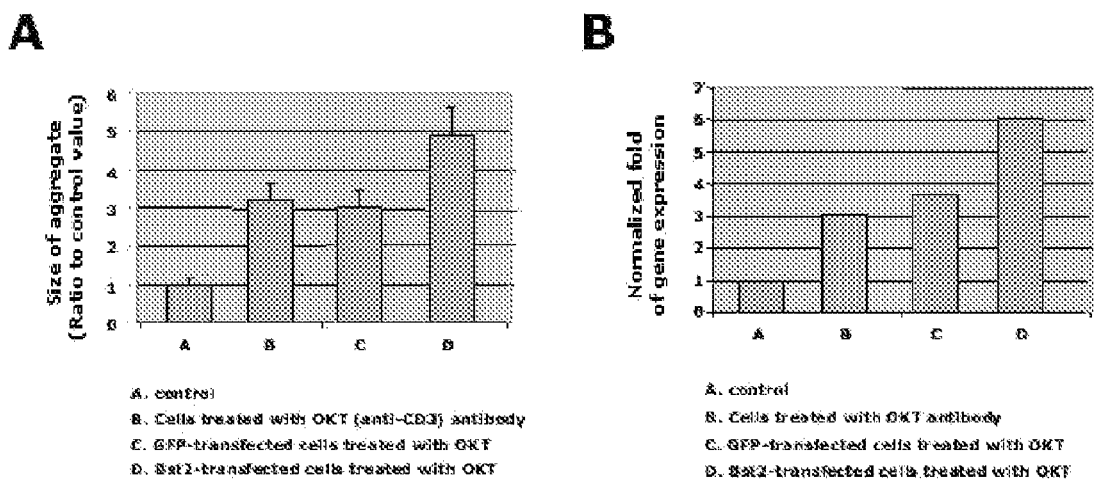
FIGS. 11A-11B show the effect of Bst2 overexpression on aggregation of Jurkat cells and interleukin-2 (IL-2) production in Jurkat cells.
Figure 12:
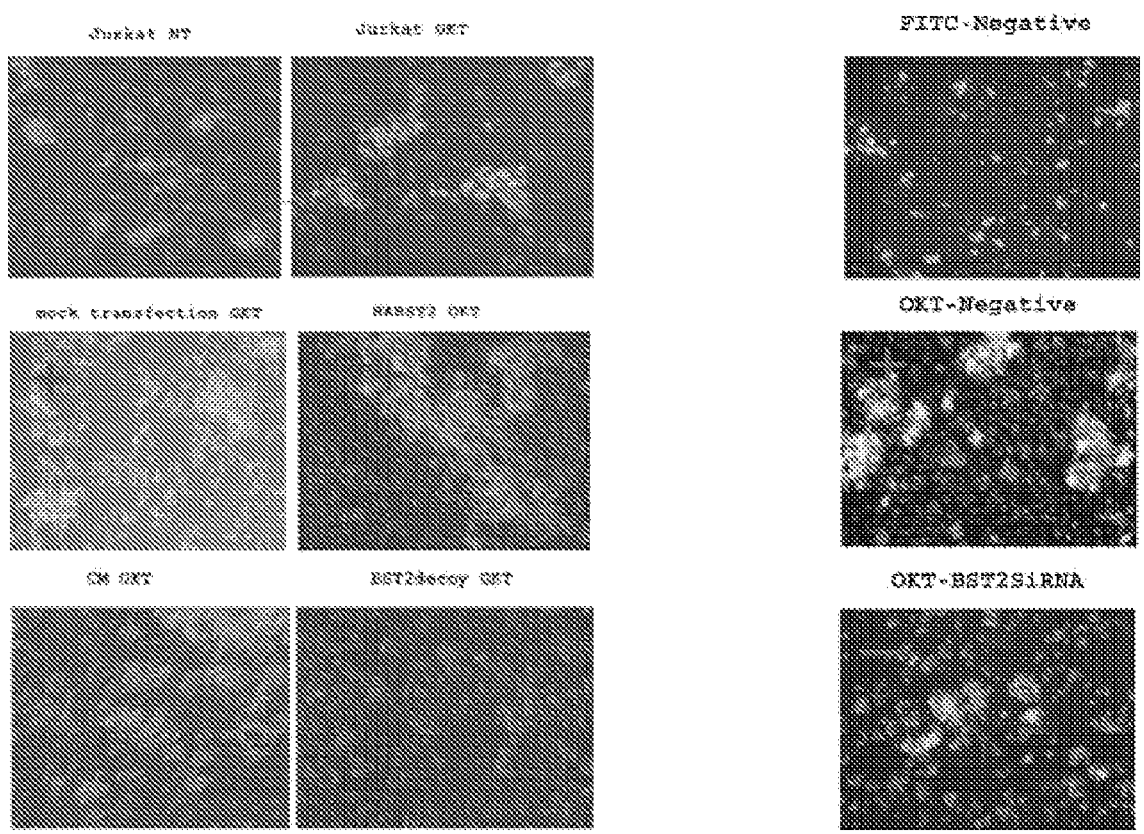
FIG. 12 shows the effect of a Bst2 soluble fragment and Bst2 siRNA on aggregation of Jurkat cells.

When Jurkat cells ($5 \times 10^5$ cells/ml) were incubated with anti-CD3 monoclonal antibody (OKT3: 10 µg/ml, BD Pharmingen) at 4° C. for 20 min and then with anti-mouse immunoglobulin polyclonal antibody (25 µg/ml, Zymed) 37° C. for 1 hr, cell aggregation occurred, and the cells were activated and induced to produce interleukin-2 (IL-2) (FIGS. 11 and 12). According to the same method, when green fluorescent protein (GFP) overexpression was induced, there was no effect. In contrast, when Jurkat cells were transfected with a Bst2-overexpressing vector and were induced to activate, homotypic cell aggregation increased by 5% or higher (FIG. 11, panel A). IL-2 mRNA levels upon T cell activation were measured by real-time RT-PCR (Example 3). IL-2 mRNA expression was elevated by about two times under Bst2 overexpression in comparison with GFP overexpression (FIG. 11, panel B).

Example 7-2

The Effect of Bst2 Soluble Fragment and Bst2 siRNA on Homotypic Aggregation of T Lymphocytes and IL-2 Production Jurkat cells were pretreated with a Bst2 soluble fragment 30 min before activation, were activated using anti-CD3 monoclonal antibody, and were evaluated for inhibition of cell aggregation. The cells were treated with a relative amount of serial dilutions of an animal cell culture fluid containing a Bst2 soluble fragment. The size aggregates were represented as a ratio to the size of aggregates of a non-treatment group.

The Bst2 soluble fragment pretreatment under the activation condition resulted in a 50% decrease in aggregation of Jurkat cells. In addition, the 3-fold increased expression of IL-2 by Jurkat cell activation was decreased again to the basal level by the Bst2 soluble fragment treatment (FIGS. 12 and 13).

Example 8

Evaluation of the Action of Bst2 Soluble Fragment in a Mouse Model of Asthma

Example 8-1

Asthma Induction in Mice

A mouse model of asthma was prepared by sensitizing mice (BALB/c, 8 weeks) with ovalbumin. In detail, mice were initially sensitized for five continuous days by intranasal injection of ovalbumin. After three weeks, mice were intranasally sensitized again with ovalbumin for five continuous days. One week after the secondary sensitization, mice were challenged intranasally with ovalbumin three times every 24 hrs to induce asthma. Herein, a Bst2 soluble fragment was intravenously injected into mice 30 min before sensitization with ovalbumin, and was injected to mice 30 min before the first sensitization and the last injection of ovalbumin. Three days after the last injection, serum samples, lung tissues, and the like were collected from mice.

Example 8-2

Figure 14:
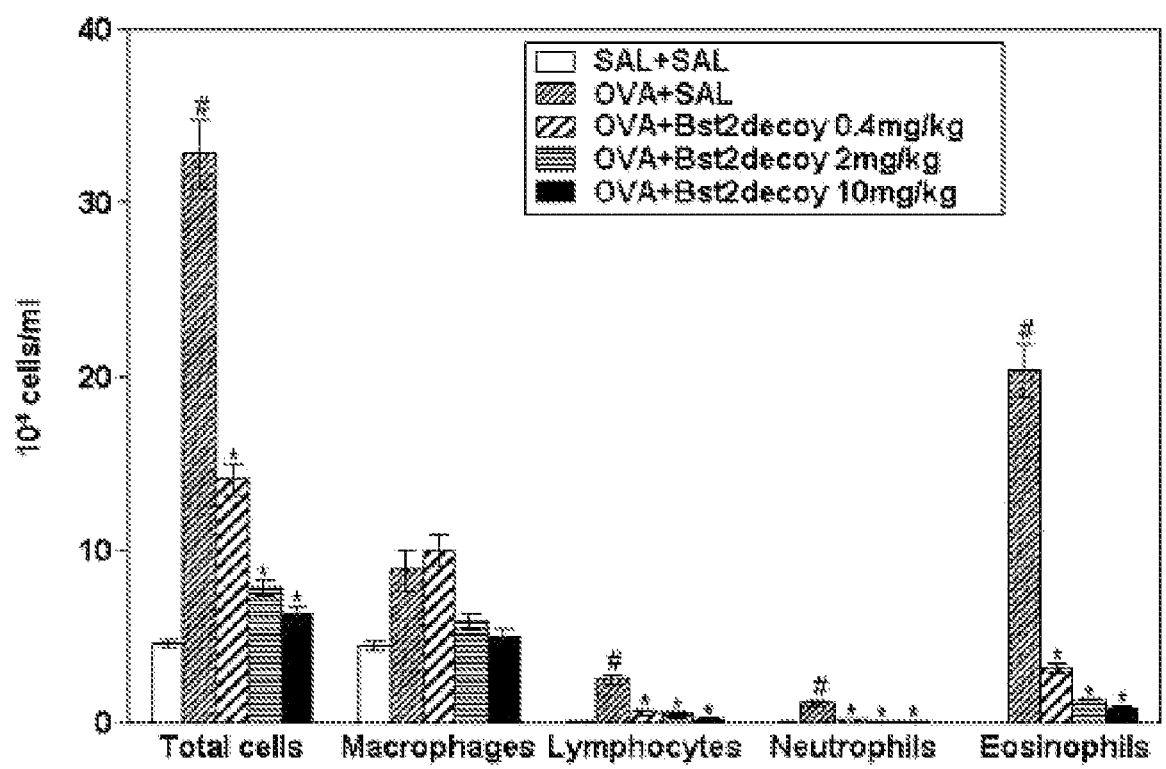
FIG. 14 shows the change in the number of sedimented immune cells upon treatment of a Bst2 soluble fragment.

Bst2 Soluble Fragment-induced Changes in the Number of Sedimented Immune Cells When a Bst2 or Damp1 soluble fragment was injected in a dose of 10 mg/kg into a mouse model of asthma which was induced by sensitization and challenge with ovalbumin, changes in the number of neutrophils, eosinophils, macrophages, lymphocytes and other cell types were assessed. Three days after the last injection of ovalbumin, mice were sacrificed, and the chest was incised to expose the lung and other organs. After the trachea was dissected at its upper part, a cannula was carefully inserted into the trachea, and bronchoalveolar lavage was performed with physiological saline pre-warmed to 37° C. The lavage fluids were collected, pooled, and centrifuged at 4° C. The sedimented cells were used for total cell counting or differential cell counting after being stained. The cell counting was performed with a hemocytometer under a microscope. In bronchoalveolar lavage fluid collected 72 hrs after sensitization with ovalbumin, the total number of cells, including neutrophils, eosinophils, macrophages and lymphocytes, increased in comparison with a control pretreated with physiological saline. When ovalbumin-sensitized mice were treated with a Bst2 soluble fragment, the total cell number and the number of each cell type (neutrophils, eosinophils and lymphocytes) remarkably decreased in bronchoalveolar lavage fluid (FIG. 14).

Example 8-3

The Effect of Bst2 Soluble Fragment on Cytokine Production

Figure 15:
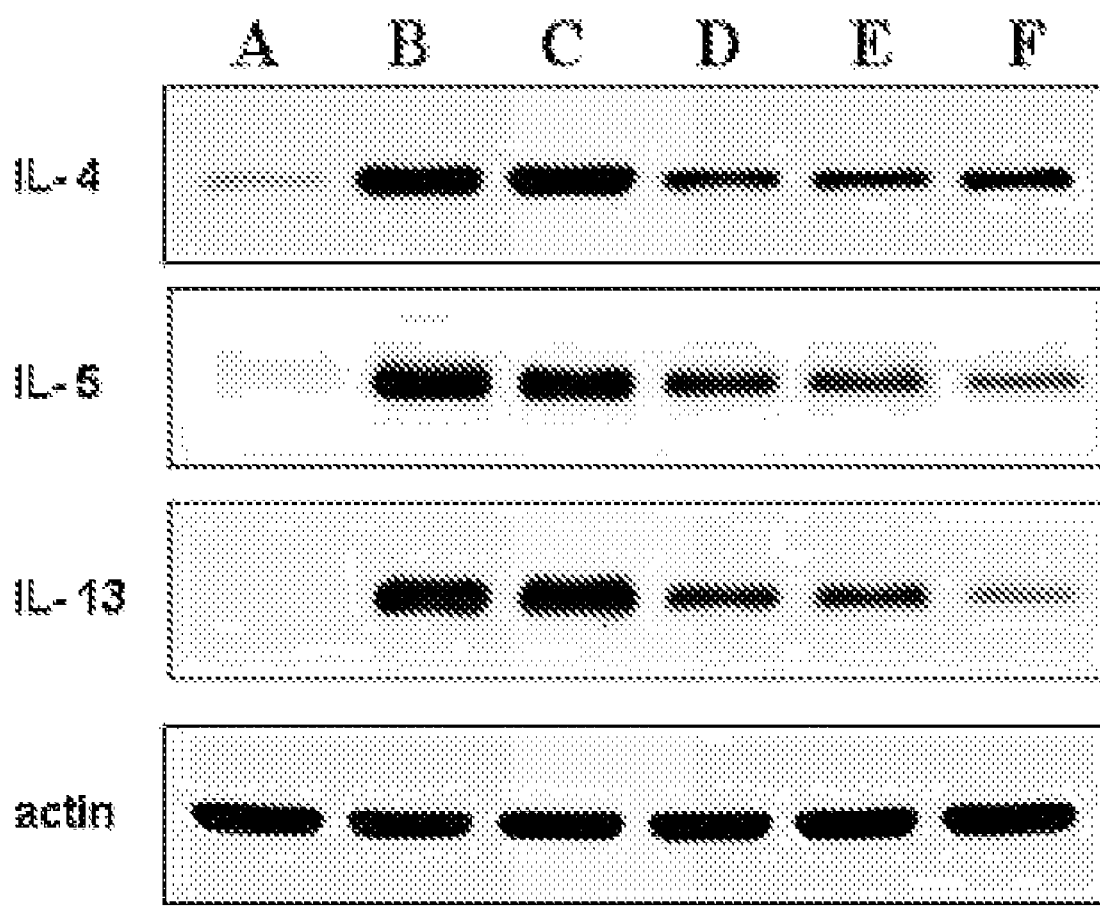
FIG. 15 shows the decreased levels of cytokines upon treatment of a Bst2 soluble fragment.

When a Bst2 or Damp1 soluble fragment was injected into a mouse model of asthma which was induced by sensitization and challenge with ovalbumin, expression levels of cytokines (interleukin-4 (IL-4), interleukin-5 (IL-5) and interleukin-13 (IL-13)) were measured, as follows. After bronchoalveolar lavage, lung tissues were excised from mice, and proteins were isolated from the lung tissues. Cytosolic proteins were isolated using lysis buffer containing NP-40. The isolated proteins were separated on a SDS-PAGE gel, and were transferred onto a PVDF membrane by a wet transfer method. The blot was incubated in a 1:1000 dilution of each several primary antibodies (anti-IL-4 antibody (Setotec Inc.), anti-IL-5 antibody (Santa Cruz Inc.), anti-IL-13 antibody (R&D Inc.), and anti-actin antibody (Sigma Inc.)). The bound primary antibodies were detected with a HRP-conjugated secondary antibody (anti-rabbit HRP-conjugated IgG) using ECL reagent. The levels of cytokines, such as IL-4, IL-5 and IL-13, were found to increase in the lung tissue of mice with asthma induced by sensitization and challenge with ovalbumin. Also, when ovalbumin-sensitized asthmatic mice were injected with a Bst2 decoy protein, cytokine levels decreased with increasing doses of the decoy protein. These results indicate that the Bst2 decoy protein has a therapeutic effect on asthma (FIG. 15).

Example 9

Figure 16:
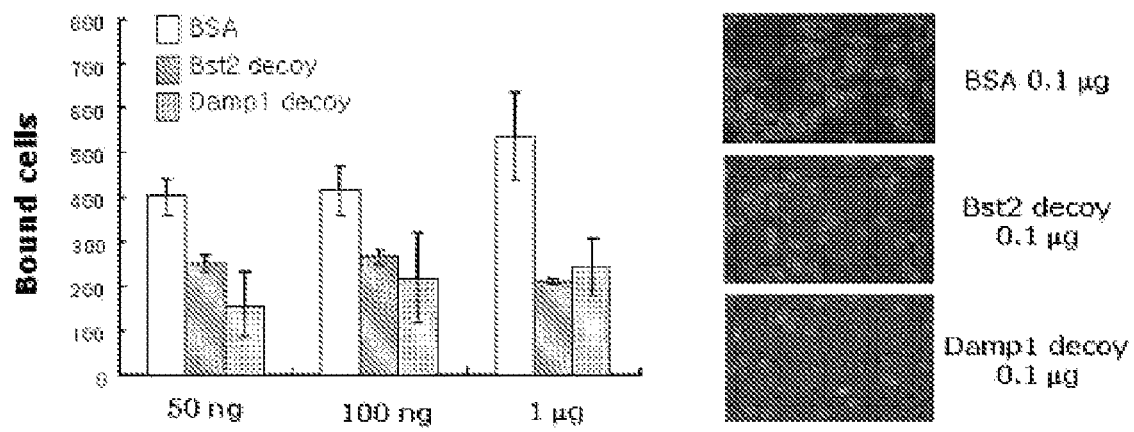
FIG. 16 shows the functional similarity between human Bst2 and mouse Damp1.
Figure 17:
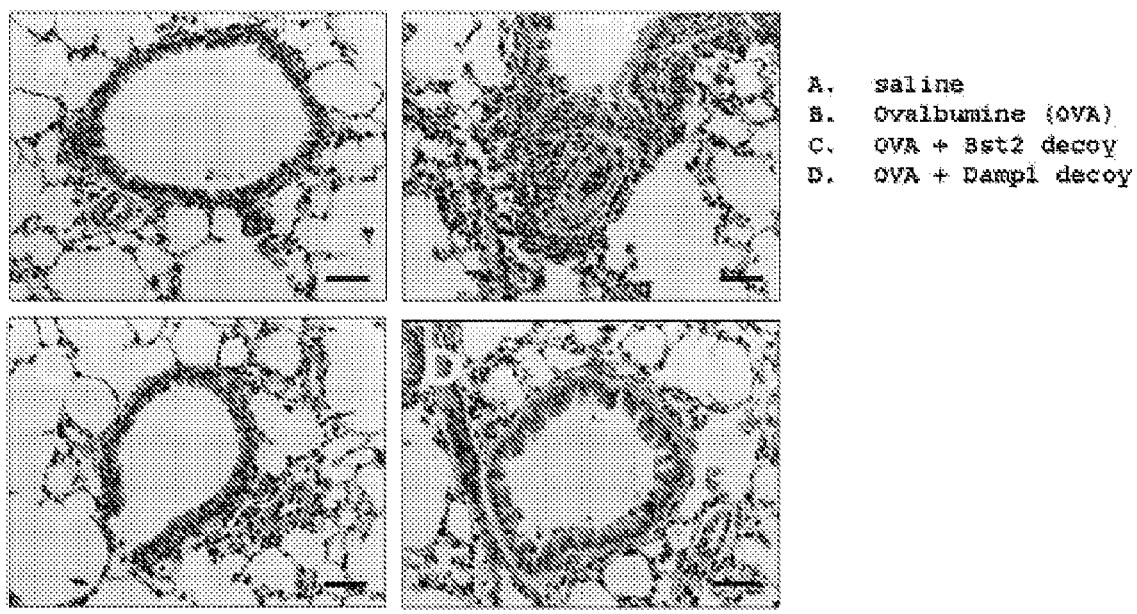
FIG. 17 shows the inhibitory effect of a mouse Damp1 soluble fragment on asthma induced in mice.

Evaluation of Functional Similarity Between Human Bst2 Protein and Mouse Damp1 Protein There is an about 35% amino acid sequence similarity between human Bst2 protein and mouse Damp1 protein. In this regard, it was examined that the two proteins interact with each other in vivo. Human Bst2 and mouse Damp1 proteins were examined for an inhibitory effect on adhesion between IFN-ɣ-treated HUVEC cells and U937 cells according to the same method as in Example 5. The treatment of bovine serum albumin (BSA) as a control protein resulted in no change in the number of U937 cells bound to HUVEC cells in comparison with the case of being treated with only culture medium. When cells were treated with human Bst2 decoy protein and mouse Damp1 decoy protein, the intercellular adhesion between HUVEC cells and U937 cells were inhibited in a dose-dependent manner (FIG. 16). Separately, the lung tissue collected in Example 8 from asthmatic mice three days after asthma induction was fixed in 10% formaldehyde, embedded in paraffin and sectioned. The paraffin sections were stained with hematoxylin and eosin. Neutrophils, eosinophils, macrophages, lymphocytes and other cell types were recruited to and filled the alveolar tissue of ovalbumin-sensitized asthmatic mice, and the airway epithelial tissue was thickened and covered with mucous secretions and cellular debris (FIG. 17). When asthmatic mice were treated with a mouse Damp1 soluble fragment or human Bst2 soluble fragment, the number of neutrophils, eosinophils, macrophages, lymphocytes and other cell types, recruited into the alveolar tissue, was greatly reduced, and no histopathological abnormality was observed in the alveolar tissue like that of non-asthmatic mice (treated with physiological saline). These results indicate that a mouse Damp1 soluble fragment has an asthma-inhibiting effect comparable to that of a human Bst2 soluble fragment protein.

Example 10

Preparation of Anti-Bst2 Polyclonal Antibody

The purified Bst2 and Damp1 decoy proteins expressed in CHO—S cells were mixed with a Ribi adjuvant at a ratio of 1:1, and were injected into rabbits with time intervals of two weeks. During immunization, blood samples were collected and examined for antibody production. After three immunizations, serum samples were obtained from rabbits. Anti-Bst2 polyclonal antibody was purified by affinity chromatography using a column in which Bst2 protein was bound to an immobilized support.

Example 11

Preparation of PEG-conjugated Forms for Improvement of Metabolism of Bst2 Soluble Fragment Example 11-1

Preparation of PEG-conjugated Forms

PEG conjugation was carried out by two types of PEG: (1) aldehyde PEG and (2) succinimidyl carbonate PEG (FIG. 18). First, aldehyde PEG conjugation was carried out as follows. 1 mg of Bst2 soluble fragment protein was dialyzed in 0.1 M phosphate buffer (pH 7.5), and was mixed with a 30-fold molar ratio of (mPEG12000-OCH$_2$COGly-Gly)$_2$(2, 4-diamino butylic acid)-PEG'-NHS, followed by incubation at room temperature of 2 hrs with agitation. Separately, for carbonate PEG conjugation, 1 mg of Bst2 soluble fragment protein was dialyzed in 0.1 M phosphate buffer (pH 5.0), and was mixed with a 20-fold molar ratio of succinimidyl carbonate PEG, followed by incubation at room temperature of 2 hrs with agitation. After the reaction was completed, PEG-conjugated Bst2 soluble fragments were isolated and purified using a size exclusion column (SUPERDEX® 200, Pharmacia), and were dialyzed in 50 mM phosphate buffer (pH 7.4).

Example 11-2

Figure 19:
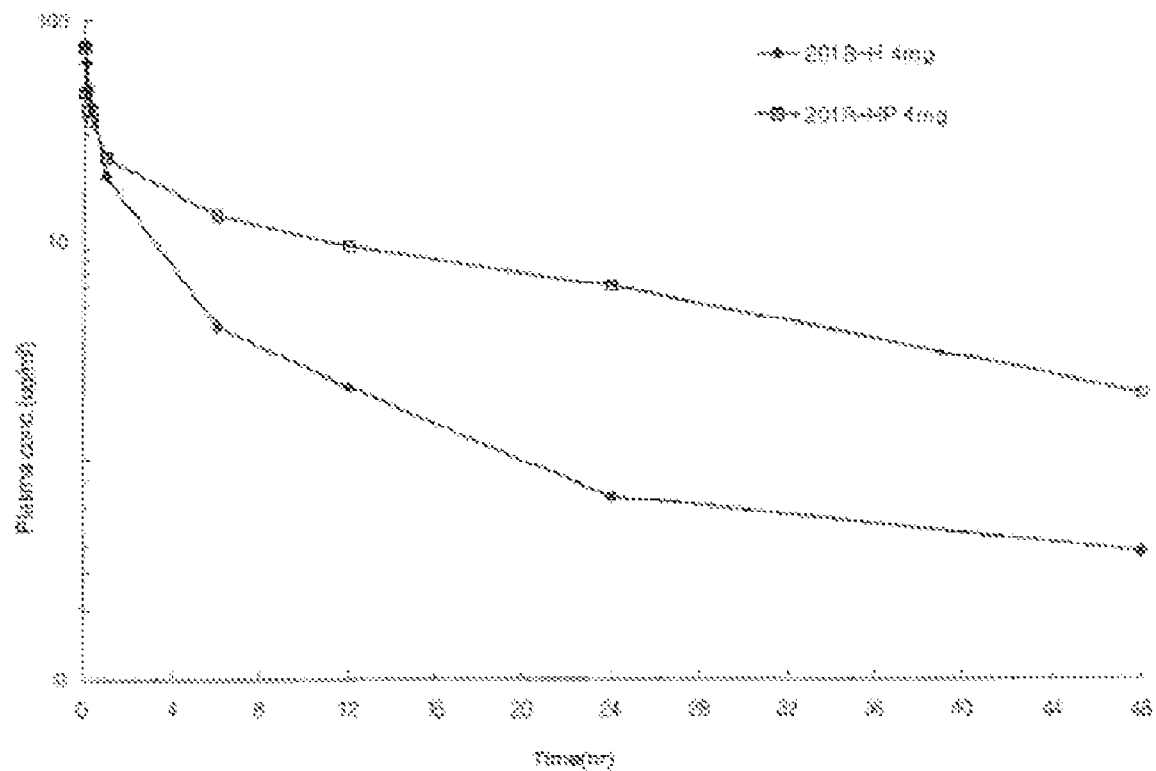
FIG. 19 shows the improved metabolic degradation of PEG-conjugated Bst2.

The Enhancing Effect of PEG-conjugated Forms on in vivo Stability of Bst2 Soluble Fragment The PEG-conjugated forms of Bst2 soluble fragment, prepared in Example 11-1, were injected into the tail vein of 7 week-old male Sprague-Dawley rats in a dose of 0.4 to 2 mg/kg. A negative control group was injected with an equal dose of physiological saline. Also, an equal dose of Bst2 soluble fragment protein was used as a positive control. Blood samples were collected before drug administration, and 2 min, 5 min, 10 min, 30 min, 1 hr, 2 hrs, 6 hrs, 12 hrs and 24 hrs after drug administration from the jugular vein using a cannula. The collected blood samples were analyzed by ELISA. A 96-well plate was coated with an anti-Bst2 soluble fragment antibody (100 ng/ml in PBS) at 4° C. for 8 hrs or longer, and was blocked with albumin in PBS at 37° C. for 2 hrs. The plate was reacted with a proper dilution of rat serum or Bst2 soluble fragment (standard sample) at 37° C. for 2 hrs. The plate was then reacted with a monoclonal antibody (mAb conjugated with horseradish peroxidase, Roche Inc.) recognizing the histidine tag added to the C-terminus of Bst2 soluble fragment at 37° C. for 2 hrs. After being well washed, the plate was treated with a substance of peroxidase, and absorbance was measured at 450 nm. Quantization of the PEG-conjugated Bst2 soluble fragments present in blood was performed using the standard samples (FIG. 19). In FIG. 19, "201B-H" indicates a human Bst2 soluble fragment sample, and "201B-HP" indicates an aldehyde PEG-conjugated human Bst2 soluble fragment sample.

Example 12

Expression and Distribution of Bst2 in Inflammation-associated Diseases

Expression levels of Bst2 protein were examined in inflammation-associated diseases including asthma, atherosclerosis, rheumatoid arthritis, psoriasis, Crohn's disease and ulcerative colitis. A paraffin block of the lung tissue, prepared by fixing the lung tissue in 10% formaldehyde and embedding the tissue in paraffin, was sectioned into a thickness of 1.5 μm, and was mounted onto glass slides. The slides were stained with hematoxylin and eosin to investigate the changes in the lung tissue according to allergen and drug administration. Histostaining was performed with the polyclonal antibody prepared in Example 10. As a result, compared to the normal tissue, Bst2 protein was overexpressed in inflammation-associated diseases, and was expressed in immune cells, vascular endothelial cells and other cell types (FIG. 20).

Example 13

Cell Culture

A human monocytic cell line U937 (ATCC, Cat. CRL-1593.2) was suspension-cultured in RPMI-1640 (Gibco-BRL) supplemented with 10% fetal bovine serum (FBS; Gibco-BRL), 100 U/ml of penicillin (Gibco-BRL) and 100 μg/ml of streptomycin (Gibco-BRL) at 37° C. under a 5% $CO_2$ atmosphere.

Human umbilical vein endothelium cell line HUVEC (Cambrex, Cat. CC-2517A) was cultured in EGM-2 medium (Cambrex) supplemented with 10% FBS at 37° C. under a 5% $CO_2$ atmosphere. In the following examples, cells were pretreated with 0.5% FBS, instead of 10% FBS, for 16 hrs. According to given conditions, cells were pretreated with human recombinant interferon-gamma (10 ng/ml, Cambiochem) for a predetermined period of time.

Mouse endothelium cell line SVEC 4-10 (ATCC, CRL-2181) was cultured in DMEM medium (Gibco-BRL) supplemented with 10% FBS at 37° C. under 5% $CO_2$ atmosphere. In the following examples, cells were pretreated with 2% FBS, instead of 10% FBS, for 16 hrs. According to given conditions, cells were pretreated with human recombinant interferon-gamma (10 ng/ml, Cambiochem, U.S.) for a predetermined period of time.

Example 14

Cloning of Human Bst2 Gene and Human Immunoglobulin Genes

Fusion constructs are prepared based on expression vector pCDNA 3.1 or other dhfr vectors commercially available.

Figure 21:
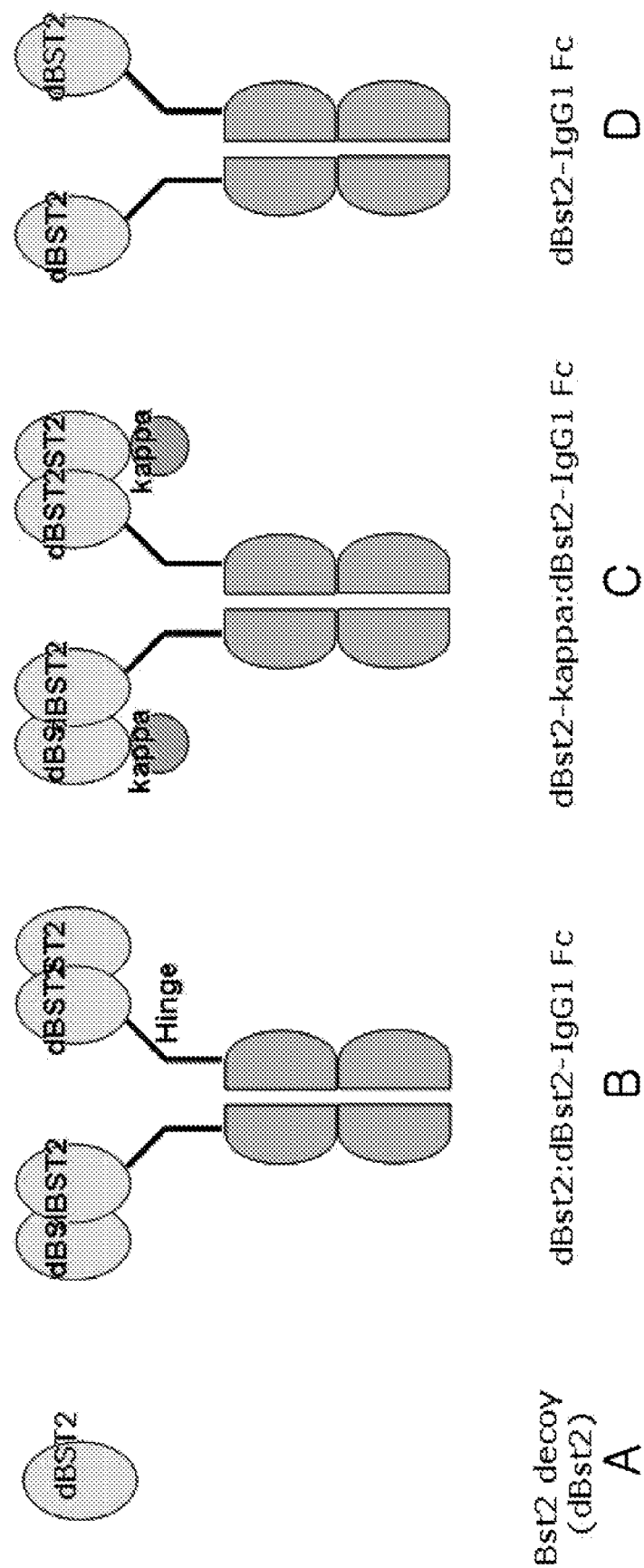
FIGS. 21A-21D show schematics of Bst2 decoy fused to Fc region. A, the Bst2 decoy itself; B, the Bst2 decoy fused to the hinge-CH2-CH3 portion of an IgG heavy chain Fc; C, Bst2 fusion protein that is stabilized through the naturally occurring IgG kappa chain-heavy chain disulfide bonding; D, Bst2 decoy-IgG Fc is expressed without other Bst2 dimerization counterparts.

FIG. 21 shows a schematic of Bst2 decoy and other Fc fusions. These are schematic representations of possible fusion proteins. Referring to FIG. 21, FIG. 21A shows the Bst2 decoy itself, FIG. 21B shows the Bst2 decoy fused to the hinge-CH2-CH3 portion of an IgG heavy chain Fc with separate expression of Bst2 decoy to form a Bst2 decoy dimer on the head of each fusion protein. FIG. 21C shows a form in which Bst2-kappa fusion is expressed in concert with the Bst2-IgG Fc fusion to allow the stable formation of Bst2 decoy dimer on the head of each fusion protein that is stabilized through the naturally-occurring IgG kappa chain-heavy chain disulfide bonding. FIG. 21D shows a form in which the Bst2 decoy-IgG Fc is expressed without other Bst2 dimerization counterparts. Dimerization of the hinge-CH2-CH3 portion of the fusion occurs in each case where the IgG Fc portion is expressed due to the naturally-occurring disulfide bonding between these chains.

FIG. 22 shows vector maps of Bst2 decoy-IgG Fc fusion proteins described above. Representative expression vectors depicting the expression vectors for the IgG1 and IgG2 Fc fusions are illustrated. FIG. 22A shows Bst2 decoy (dBst2). The Bst2 decoy expression vector was constructed by PCR-cloning an Xba1 site 5' of the start of the decoy protein with an N-terminal tPA signal peptide and C-terminal His-tag followed by a BamH1 site on the 3' end; this insert was cloned into pcDNA3.1 cut with Xba1 and BamH1. FIG. 22B shows dBst2-IgG1Fc fusion. The hinge-CH2-CH3 region of IgG1 heavy chain was PCR-cloned and fused to the C-terminal end of Bst2 decoy with a 5' Xho1 and 3' Not1 site; this insert was cloned into pcDNA3.1 cut with Xho1 and Not1. FIG. 22C shows dBST-kappa fusion. The constant region of the IgG kappa light chain was PCR-cloned and fused to the C-terminal end of Bst2 decoy with a 5' Xho1 and 3' Not1 site; this insert was cloned into pcDNA3.1 cut with Xho1 and Not1. (d) dBST-IgG2HC fusion. The hinge-CH2-CH3 region of IgG2 heavy chain was PCR-cloned and fused to the C-terminal end of Bst2 decoy with a 5' Xho1 and 3' Not1 site; this insert was cloned into pcDNA3.1 cut with Xho1 and Not 1.

Example 15

Vector Construction

An expression vector of histidine-tagged Bst2 was constructed as follows. Full-length cDNA (NM004335; SEQ ID NO:1) of human Bst2 gene was synthesized by Origene Technologies (USA), and amplified by PCR using Pfu ultra HF DNA polymerase (Stratagene) in a volume of 50 μl. A PCR product was cloned into a pCMV HA vector (Clontech) using SalI and NotI. A DNA fragment coding for the extracellular region of human Bst2 protein was obtained by PCR, and was fused at the N-terminus to a signal sequence P of tPA (tissue Plasminogen activator) to promote extracellular secretion after being expressed. The DNA fragment was also fused at the C-terminus to a six-histidine tag to facilitate determination of protein expression levels and protein purification. The Bst2 soluble fragment did not contain 11 amino acid residues at the C-terminus and also did not contain the transmembrane and cytoplasmic domains. The PCR product was digested with BamHI and XbaI, and cloned into a pCDNA 3.1 vector (Invitrogen).

Immunoglobulin gene fragments were cloned from a human blood cell cDNA library (Clontech) by PCR: the Fc region (hinge, CH1 and CH2 region) of human IgG1 heavy chain (Genbank No: BC089417, primers 1, 2), the constant region of human immunoglobulin kappa chain (Genbank No: BC067092, primers 3, 4), and the constant region (CH1-hinge-CH2-CH3) of human IgG2 heavy chain (Genbank No: AJ294731, primer 5, 6). The sequence of PCR primers used in cloning the fragment are as follows.

```
Sequence 1
                                    (SEQ ID NO: 10)
201-H-5':    5'-ctc cca gga cga gcc caa atc ttg-3'

Sequence 2
                                    (SEQ ID NO: 11)
201-IgG1-3': 5'-ggcggccgc TCA ttt acc cgg gga-3'

Sequence 3
                                    (SEQ ID NO: 12)
201-L-5':    5'-ctc cca gga ccg tac ggt ggc tgc-3'

Sequence 4
                                    (SEQ ID NO: 13)
201-kappa-3':5'-ggcggccgc TTA aca ctc tcc cct-3'

Sequence 5
                                    (SEQ ID NO: 14)
201-H2-5':   5'-ctc cca gga cgc ctc cac caa ggg-3'

Sequence 6
                                    (SEQ ID NO: 15)
201-IgG2-3': 5'-ggcggccgc TCA ttt acc cag aga-3'
```

Example 16

Cloning of Human Bst2 Decoy-Fc Fusion Constructs (IgG1, 2, and 4)

Three different constructions of human Bst2 decoy-Fc fusion were cloned into the expression vector pCDNA3.1 (Invitrogen). A DNA fragment coding for the extracellular region of human Bst2 protein was obtained by PCR, and was fused at the N-terminus to the signal peptide sequence of tPA to promote extracellular secretion after being expressed. The BST2 extracellular fragment was also fused at the C-terminus to IgG1 Fc region of IgG1, IgG2 and IgG4 or the constant region of kappa chain. The overlapped PCR product was digested with XhoI and NotI, and cloned into the vector pCDNA3.1 (Invitrogen). These fused fragments were produced by overlap PCR and primers were as follows and designated "pcDNA-dBST2-IgG1 Fc", "pcDNA-dBST2-kappa", and "pcDNA-dBST-IgG2HC" or "pcDNA-dBST2-IgG4Fc".

Example 17

Figure 23:
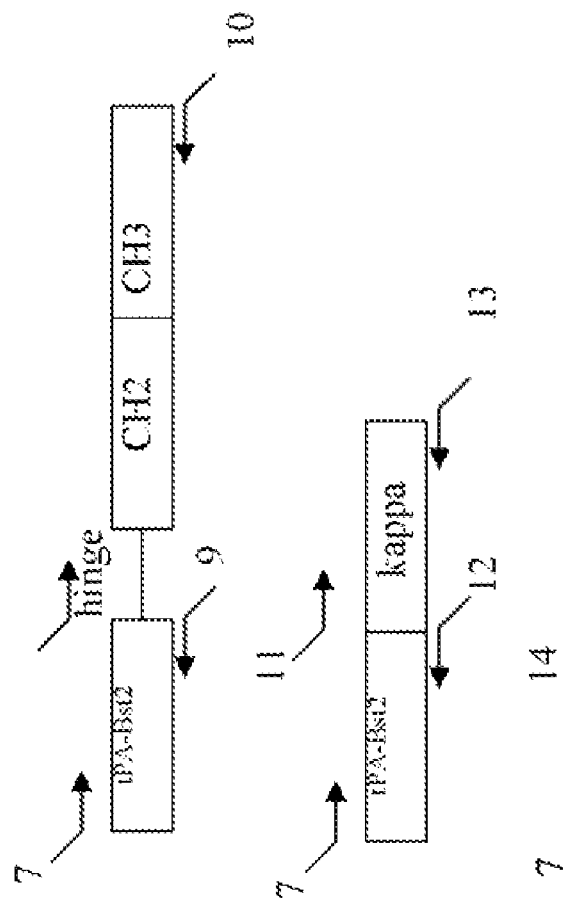
FIG. 23 shows PCR-cloning and fusion strategy.

PCR cloning and fusion strategy is set forth in FIG. 23. The following primers were used.

```
Sequence 7
                                    (SEQ ID NO: 16)
tPAsig_XhoI_Fw:  5'-cgctcgagacagccatcATGgatg-3'

Sequence 8
                                    (SEQ ID NO: 17)
201-H-5':       5'-ctc cca gga cga gcc caa atc
                ttg-3'

Sequence 9
                                    (SEQ ID NO: 18)
201-H-3':       5'-ttg ggc tcg tcc tgg gag ctg
                ggg-3'

Sequence 10
                                    (SEQ ID NO: 19)
201-IgG1-3':    5'-ggcggccgc TCA ttt acc cgg gga-
                3'

Sequence 11
                                    (SEQ ID NO: 20)
201-L-5':       5'-ctc cca gga ccg tac ggt ggc
                tgc-3'

Sequence 12
                                    (SEQ ID NO: 21)
201-L-3':       5'-acc gta cgg tcc tgg gag ctg
                ggg-3'

Sequence 13
                                    (SEQ ID NO: 22)
201-kappa-3':   5'-ggcggccgc TTA aca ctc tcc cct-
                3'

Sequence 14
                                    (SEQ ID NO: 23)
201-H2-5':      5'-ctc cca gga cgc ctc cac caa
                ggg-3'

Sequence 15
                                    (SEQ ID NO: 24)
201-H2-3':      5'-gtg gag gcg tcc tgg gag ctg
                ggg-3'

Sequence 16
                                    (SEQ ID NO: 25)
201-IgG2-3':    5'-ggcggccgc TCA ttt acc cag aga-
                3'

Sequence 17
                                    (SEQ ID NO: 26)
201-H4-3';      5'-cat att tgg act cgt cct ggg
                agc-3'

Sequence 18
                                    (SEQ ID NO: 27)
201-H4-5';      5'-ctc cca gga cga gtc caa ata tgg
                tcc c-3'

Sequence 19
                                    (SEQ ID NO: 28)
201-IgG4-3';    5'-ggc ggc cgc TCA ttt acc cag aga
                cag g-3'
```

Example 18

Expression of Soluble Decoy-Fc Fusion Proteins

In order to express soluble Bst2 decoy-Fc fusion proteins, the expression vector DNA was transiently or stably introduced into mammalian cells. Transient transfection was performed by calcium phosphate ($CaPO_4$) precipitation, as follows. One day before transfection, $7\times10^6$ cells of 293T (ATCC) were seeded and cultured onto a 150-mm cell culture plate. One hour before transfection, the culture medium was exchanged with IMDM medium (Cambrex) supplemented with 2% fetal bovine serum (GIBCO-BRL). TE buffer (1 mM Tris, 0.1 mM EDTA, pH 8.0) containing 75 μg of DNA and 250 mM calcium chloride in a volume of 1.5 ml, was mixed with equal volume of HEPES buffer (50 mM HEPES, 140 mM NaCl, 1.4 mM $Na_2HPO_4$, pH 7.05). The mixture was incubated for about 1 min at room temperature and was applied to the pre-cultured cells. The cells were incubated in a $CO_2$ incubator at 37° C. for 6 hrs. The DNA/calcium solution was removed, serum-free medium was added and the transfected cells were further cultured for 72 hrs or longer, and then the culture medium was harvested.

A cell line for stable expression was established using lipofectamine transfection method. Two days before transfection, $1.35\times10^6$ cells of CHO-DUKX-B11 (dhfr$^-$) were seeded onto a 100-mm cell culture plate and cultured in IMDM medium complemented with 10% FBS. Serum-free IMDM medium containing 18 μg of DNA in a volume of 0.6 ml was mixed with equal volume of serum-free IMDM medium containing 54 μl of Lipofectamine 2000 (Invitrogen), and was incubated at room temperature for 45 minutes. The DNA/lipofectamine mixture was supplemented with 8.8 ml of serum-free IMDM medium and applied to the pre-cultured cells. After a 6 hr incubation, the cells were treated with a selection medium, 10% dialyzed FBS-containing IMDM medium.

Since the expression vector carried a dhfr gene, dihydrofolate reductase was used as a selectable marker. After 48 hrs, the transfected CHO cells were seeded onto a 96-well cell culture plate in a density of $1\times10^3$ cells/well and cultured in a medium containing 20 nM methotrexate (MTX) to amplify the DHFR gene. After two weeks, the medium was recovered and subjected to ELISA using anti-Bst2 antibody to compare clones for the expression levels of Bst2 soluble fragment protein. Clones exhibiting high expression levels were selected and exposed to gradually increased concentrations of MTX up to 300 nM to complete gene amplification. Thereafter, the medium was collected from each clone and subjected to ELISA and immunoblotting in order to finally select a production cell line exhibiting the highest protein expression levels. The Bst2 soluble fragment protein in culture medium was analyzed by immunoblotting using anti-Bst2 polyclonal antibody (Roche).

Example 19

PAGE of Purified Bst2 Decoy and Other Fc Fusions

Fc fusion proteins were purified from the culture media. After concentration by ultra-filtration, a two-step chromatography process was used, including Protein A affinity chromatography (Amersham Biosciences, MabSelect) and size-exclusion chromatography (Amersham Biosciences, SUPERDEX® 200).

Fc fusion proteins were loaded on protein A-packed column previously equilibrated with PBS buffer (1.06 mM potassium phosphate monobasic, 155.17 mM sodium chloride, 2.97 mM sodium phosphate dibasic, pH 7.4). The column was washed with PBS buffer for removing the contaminants about 20 column volumes. Bound antibodies were eluted by low pH buffer, such as 50 mM glycine-HCl using a step gradient and neutralized with the equal volume of 1M Tris (pH 8.0).

An additional size-exclusion chromatography step is utilized to remove immunoglobulin multimers. The purified antibody multimer mixture was loaded onto a SUPERDEX® 200 column previously equilibrated with PBS (pH 7.4). The linear flow rate of the buffer was selected from rates within the range of 50 cm/h to 150 cm/h.

Figure 24:
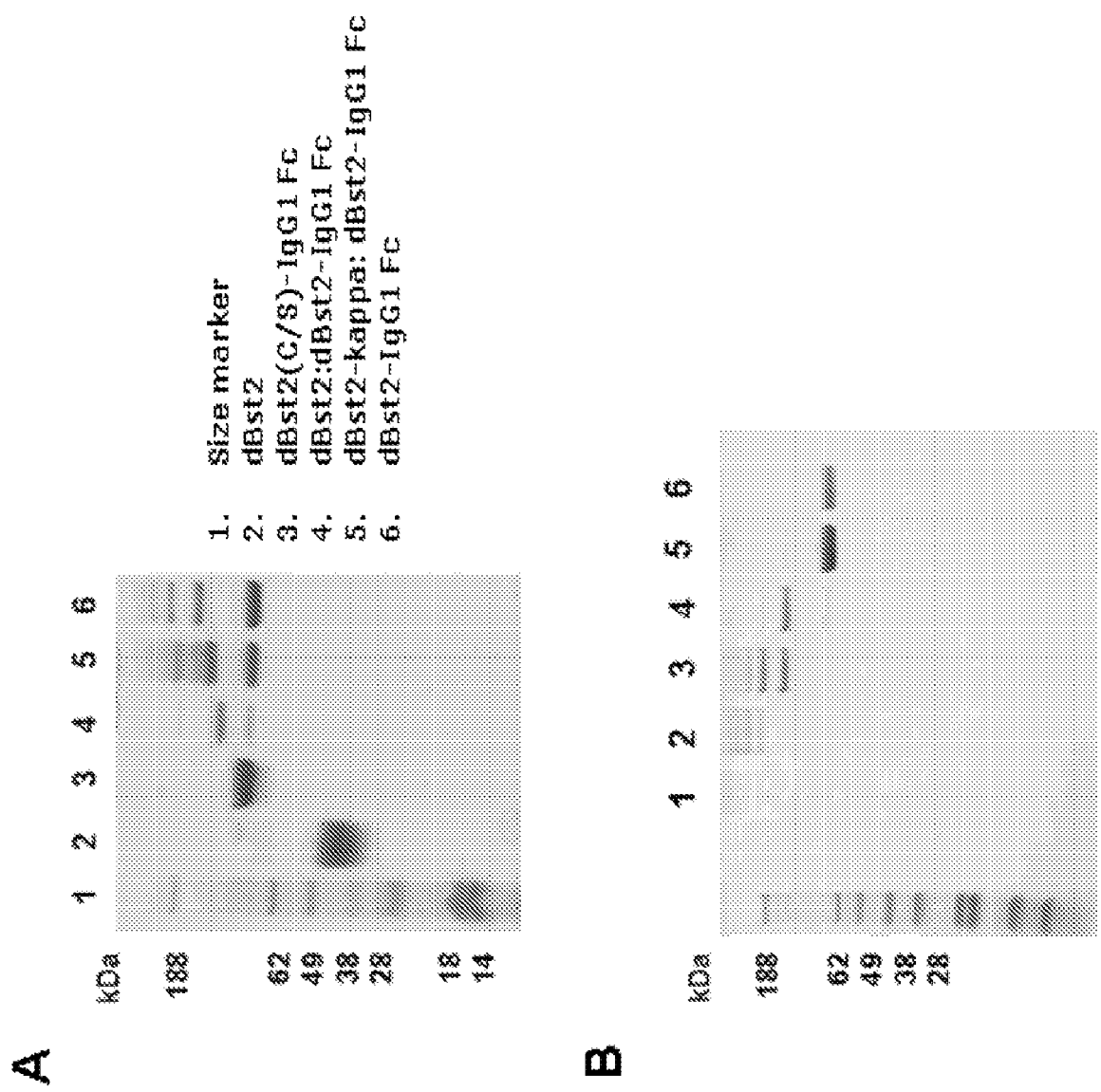
FIGS. 24A-24B show PAGE gels of purified Bst2 decoy and other Fc fusions. A, representative PAGE gel (4~12% gradient gel, Invitrogen) stained with Coomassie depicting various Bst2 fusion proteins following affinity purification. B. PAGE gel after size-exclusion chromatography of the sample from lane 6 in FIG. 24A.

FIG. 24 shows a representative PAGE gel (4~12% gradient gel, Invitrogen) stained with Coomassie depicting various Bst2 fusion proteins following affinity purification. FIG. 24B shows high molecular weight, multimeric forms can be removed by appropriate size-exclusion chromatography as depicted in FIG. 24B where the lanes are fractions of the proteins from lane 6 following chromatography.

Example 20

Direct Binding of Bst2 Decoy to Immune Cells

Flat-bottomed 96-well plates were coated with 100 mL of Bst2 decoy (50 mg) with sodium bicarbonate (100 mM, pH 9.5) for 2 hrs at 37° C. The plates were washed with PBS (pH 7.4) and incubated with 1% bovine serum albumin (BSA) at 25° C. After a rinse with PBS (pH 7.4) containing 1 mM $CaCl_2$ and 0.5 mM $MgCl_2$, 50 mL of a $1\times10^6$/ml U937 cell suspension were added to each dBst2-coated well. Total adhesion cell counts were assessed after incubation for 2 hrs at 37° C. Non-adherent cells were removed by two gentle washes with RPM11640 media (Gibco-BRL) and residual attached cells were fixed with 2% paraformaldehyde for 20 minutes, washed, and stained with 0.5% crystal violet. After 30 minutes at 25° C., the plates were washed with PBS and adherent cells were counted.

Figure 25:
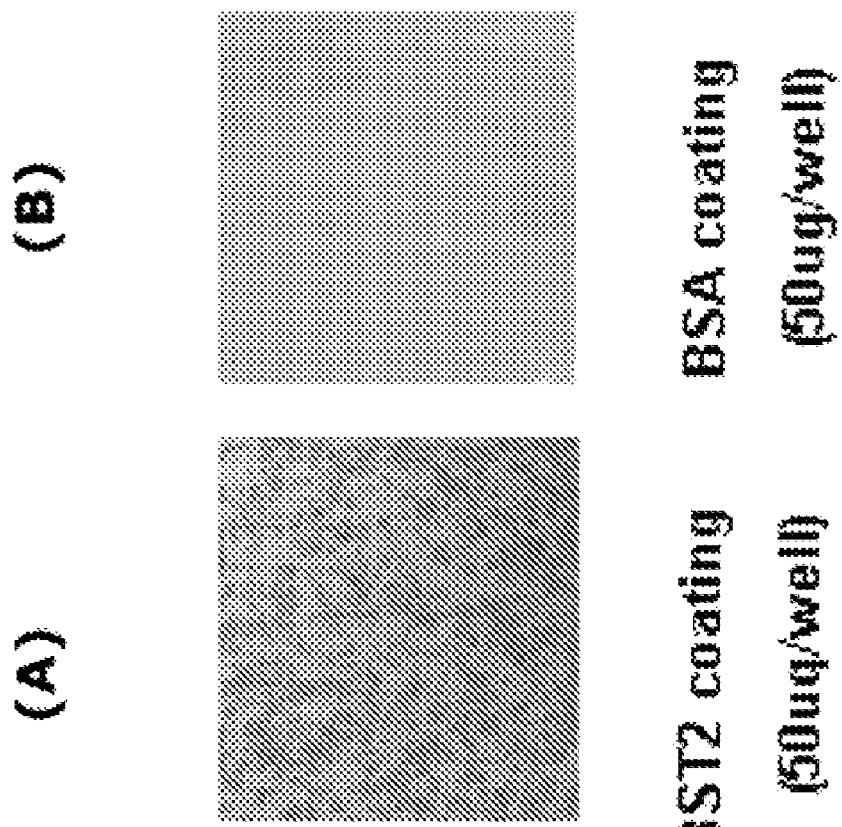
FIGS. 25A-25B show direct binding of Bst2 decoy to immune cells on A, Bst2 coated plate; and B, BSA coated plate.

FIG. 25 shows direct binding of Bst2 decoy to immune cells. Cell culture plates coated with Bst2 directly bind to and retain U937 cells (left panel), whereas BSA-coated control plates cannot retain the U937 cells.

Example 21

Plasma Half-life of Bst2 Decoy-Fc Fusions

Figure 26:
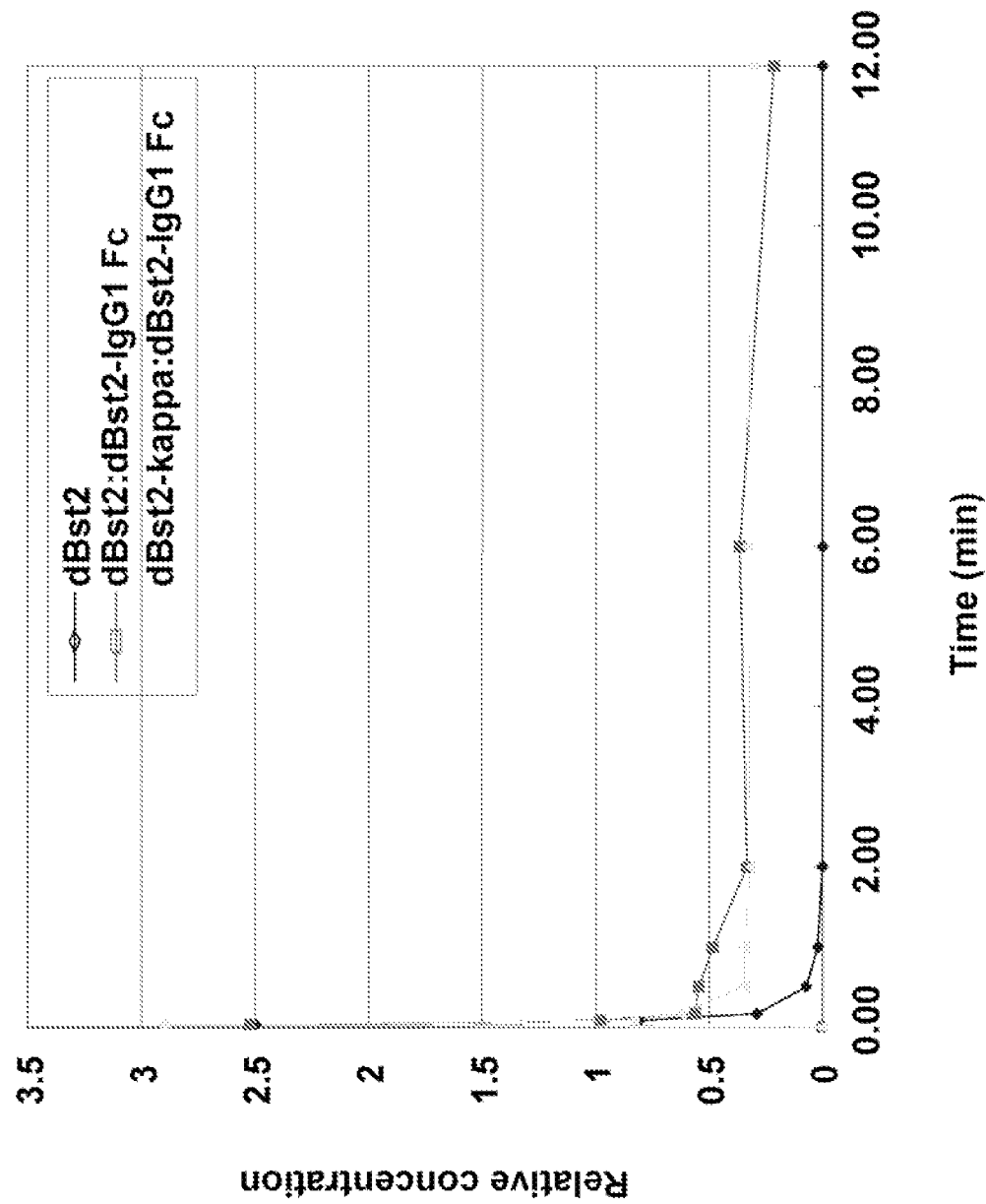
FIG. 26 shows plasma half-life of Bst2 decoy or Fc fusions.
Figure 27:
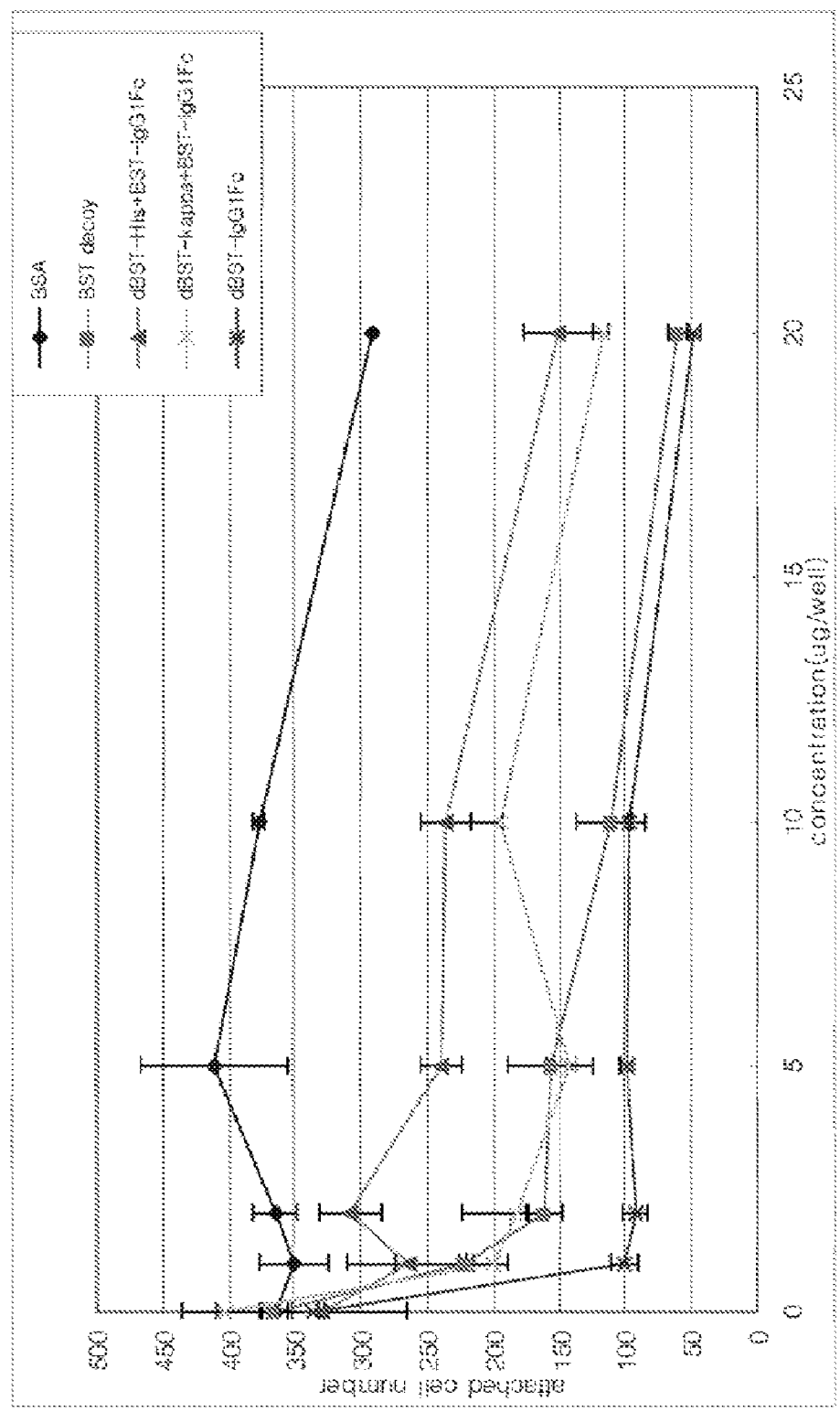
FIG. 27 shows inhibition of Bst2 decoy-Fc fusions in the binding between Bst2 decoy and cells.

FIG. 26 shows plasma half-life of Bst2 decoy or Fc fusions. The Bst2 decoy protein fused to various stabilizing IgG Fc regions demonstrate enhanced serum stability, as indicated by a representative pharmacokinetics plot for two Bst2 decoy-IgG1 fusions compared to Bst2 decoy alone.

To determine plasma half-life of Bst2 decoy or other Fc fusions, rats (Sprague-Dawley males) were surgically implanted with intravenous catheter. During subsequent sessions, the catheters were connected to an infusion pump. The protein sample was infused by hand over 1 min through catheters flushed with heparinized saline to reduce the risk of clotting. The end of the infusion was designated as time 0. Blood samples (0.4 ml) were withdrawn from the catheters at various time points. The plasma was separated by centrifugation and applied to a sandwich ELISA assay for determination of the plasma concentration of BST2 decoy or other Fc fusion proteins. The wells in a 96 well plate were coated with (100 μl/well) a 5 ug/ml solution of rabbit anti-BST2 polyclonal antibody in 50 mM carbonate buffer (pH 9.2) and blocked with 1% BSA/PBS. Each plasma sample diluted to fall into the linear range of the standard curve were incubated at 25° C. for 90 min. After PBS washing, the wells were incubated with horseradish peroxidase-labeled goat anti-Human IgG (1:50,000 dilution, Fc specific, Sigma, Cat. No. A-0170) at room temperature for 1 hour and then treated with TMB substrate (Pierce). The plates were read at 450 nm in a plate reader and the data were analyzed using the four-parameter curve-fitting program. For standard curve for each different protein, each purified protein standard was used in the solution of 1% BSA, 1% rat pre-immune serum with appropriate concentrations.

Example 22

Inhibition of Bst2 Decoy-Fc Fusions in the Binding Between Bst2 Decoy and Cells

Bst2 decoy-IgG Fc fusion proteins demonstrate a concentration-dependent inhibition of U937 cell binding to Bst2 decoy coated cell culture plates indicating that the Bst2 decoy-IgG Fc fusion proteins are functional.

Competitive inhibition of Fc Fusion proteins in the binding between BST2 decoy and cells was measured as follows. Flat-bottomed 96-well plates were coated with 100 mL of Bst2 decoy (50 mg) with sodium bicarbonate (100 mM, pH 9.5) for 2 hrs at 37° C. The plates were washed with PBS (pH 7.4) and incubated with 1% bovine serum albumin (BSA) at 25° C. After a rinse with PBS (pH 7.4) containing 1 mM $CaCl_2$ and 0.5 mM $MgCl_2$, 50 mL of a $1\times10^6$/ml U937 cell suspension were added to each Bst2-coated well. Before the addition, cells were pre-incubated with BST2 decoy-Fc fusion proteins for 2 hrs at 37° C. Total adhesion cell counts were assessed after incubation for 2 hrs at 37° C. Non-adherent cells were removed by two gentle washes with RPM11640 media (Gibco-BRL) and residual attached cells were fixed with 2% paraformaldehyde for 20 minutes, washed, and stained with 0.5% crystal violet. After 30 minutes at 25° C., the plates were washed with PBS and adherent cells were counted.

Example 23

The Effect of Bst2 Decoy-Fc Fusions on a Mouse Model of Asthma

A mouse model of asthma was prepared by sensitizing mice (BALB/c, 8 weeks) with ovalbumin. In detail, mice were initially sensitized for five continuous days by intranasal injection of ovalbumin. After three weeks, mice were intranasally sensitized again with ovalbumin for five continuous days. One week after the secondary sensitization, mice were challenged intranasally with ovalbumin three times every 24 hours to induce asthma. Herein, a Bst2 decoy or other Fc fusion proteins was intravenously injected into mice 24 hours before challenge with ovalbumin, and was injected into mice 30 minutes before the first challenge and the last challenge of ovalbumin. Three days after the last injection, serum samples, lung tissues, and the like were collected from mice.

When Bst2 or Fc fusion protein was injected in a dose of 10 mg/kg into a mouse model of asthma which was induced by sensitization and challenge with ovalbumin, changes in the number of neutrophils, eosinophils, macrophages, lymphocytes and other cell types were assessed. Three days after the last challenge of ovalbumin, mice were sacrificed to expose the lung and other organs. After the trachea was dissected at its upper part, a cannula was carefully inserted into the trachea and bronchoalveolar lavage was washed with physiological saline prewarmed to 37° C. The lavage fluids were collected, pooled, and centrifuged at 4° C. The sedimented cells were used for total cell counting or different cell counting under a microscope. In bronchoalveolar lavage fluid collected 72 hrs after sensitization with ovalbumin, the total number of cells, including neutrophils, eosinophils, macrophages and lymphocytes, increased in comparison with a control pretreated with physiological saline. When ovalbumin-sensitized mice were treated with a Bst2 soluble fragment, the total cell number remarkably decreased fluid and, especially, the number of neutrophils, eosinophils and lymphocytes except for macrophage decreased in bronchoalveolar lavage (BAL).

Example 23-1

Diagnostic Methods to Measure the Inflammatory Status

Bst2 mRNA expression is increased in inflammatory condition. Measuring Bst2 mRNA level with quantitative PCR, real-time PCR or northern blot in cells and tissues isolated from a subject can yield useful information on the inflammation status of those cells and tissues. Measuring Bst2 protein levels by immunoblotting with antibody specific for Bst2 or alternatively with immunofluorescence microscopy and FACS (fluorescence activated cell sorter) using fluorescently-labeled antibody capable of binding to Bst2 on the cell membrane may also yield information regarding the inflammation status of those cells. Frequently, membrane proteins such as Bst2 can be cleaved to produce soluble Bst2 fragment which circulate in the body. Bst2 circulating in body fluids such as serum and urine, may be quantified with antibody specific for circulating Bst2 fragment, using commonly utilized methods such as radioimmunological assay (RIA) and ELISA. Quantification of circulating Bst2 fragment may reflect the inflammation status of the host and may be useful for diagnostic and therapeutic purposes.

Figure 28:
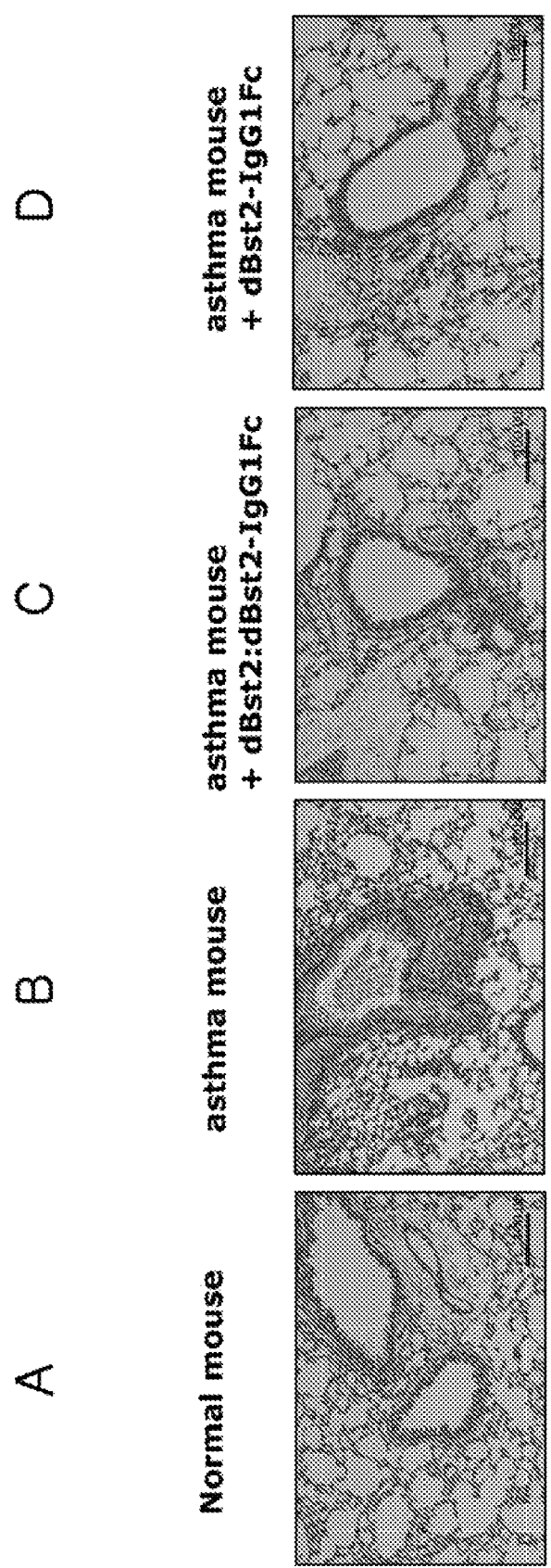
FIGS. 28A-28D show H & E staining of tissue, which show the effect of Bst2 decoy-Fc fusions on a mouse model of asthma. A. Normal mouse, B. asthma mouse untreated, C. asthma mouse treated with dBst2:dBst2-IgG1 Fc, D. asthma mouse treated with dBst2-IgG1 Fc.

When a Bst2 decoy or Fc fusion protein was injected into a mouse model of asthma which was induced by sensitization and challenge with ovalbumin, expression levels of cytokines (interleukin-4 (IL-4), interleukin-5 (IL-5) and interleukin-13 (IL-13)) were measured, as follows. After sampling BAL fluid, cytosolic proteins from lung tissue were isolated using lysis buffer containing NP-40. The isolated proteins were subject to immunoblot with several cytokine antibodies: anti-IL-4 antibody (Setotec Inc.), anti-IL-5 antibody (Santa Cruz Inc.), anti-IL-13 antibody (R&D Inc.) and anti-actin antibody (Sigma Inc.). The levels of cytokines, such as IL-4, IL-5 and IL-13, were found to increase in the lung tissue of mice with asthma induced by sensitization and challenge with ovalbumin. Also, when ovalbumin-sensitized asthmatic mice were injected with a Bst2 decoy protein, cytokine levels decreased with increasing doses of the decoy protein. These results indicate that the Bst2 decoy protein has a therapeutic effect on asthma. FIG. 28 shows the effect of Bst2 decoy-Fc fusions on a mouse model of asthma.

Example 30

Construction of Bst2/Damp1 Oriented Fab library

Human Bst2-decoy or mouse Damp1-decoy protein expressed in CHO cells was immunized into rabbits (New Zealand White) by the appropriate amount of injection with adjuvant (RIBI's or Freund's Incomplete/Complete) until the saturation of antibody titer specific to Bst2/Damp1 antigens. The antibody titer of immunized rabbits was determined by enzyme linked immunosorbent assay (ELISA) using horseradish peroxidase (HRP)-conjugated anti-His antibodies which recognize His tagged at C-termini of decoy proteins.

For preparation of Fab-display phage libraries, total RNA was prepared from bone marrow and spleen of the immunized rabbit using TRI reagent. First-strand cDNA was synthesized by using the Superscript II First-strand synthesis system with oligo (dT) priming (Invitrogen).

The first-strand cDNAs from each rabbit were subjected to first round PCR using Expand High Fidelity PCR System (Roche Molecular System) and 10 primer combinations for the amplification of rabbit $V_L$ coding sequence and 4 primer combinations for the amplification of rabbit VH coding sequences were used. Human Cκ and $C_H1$ coding sequences were amplified from Fab. The anti-sense primers consist of a hybrid rabbit/human sequences designed for the fusion of rabbit $V_L$ and $V_H$ coding sequences to human $C_k$ and CH1 coding sequences. In the second round of PCR, the first round variable region rabbit $V_H$ were overlapped with human constant CH1, and the first round variable region rabbit VL were overlapped with human constant Cκ. In the third round of PCR, the chimeric light chain products and chimeric heavy chain fragments were joined by an overlap extension PCR.

Example 30-1

The First Round PCR Primer Sets

\*Vκ 5' sense Primers
```
                        (SEQ ID NO: 29)
RSCVK1      5' ggg ccc agg cgg ccg agc tcg tgm
            tga ccc aga ctc ca 3'

(SEQ ID NO: 30)
RSCVK2      5' ggg ccc agg cgg ccg agc tcg atm
            tga ccc aga ctc ca 3'

(SEQ ID NO: 31)
RSCVK3      5' ggg ccc agg cgg ccg agc tcg tga
            tga ccc aga ctg aa 3'
```
\*Vκ 3' reverse Primers
```
                        (SEQ ID NO: 32)
RHybK1-B    5' aga tgg tgc agc cac agt tcg ttt
            gat ttc cac att ggt gcc 3'

(SEQ ID NO: 33)
RHybK2-B    5' aga tgg tgc agc cac agt tcg tag
            gat ctc cag ctc ggt ccc 3'

(SEQ ID NO: 34)
RHybK3-B    5' aga tgg tgc agc cac agt tcg ttt
            gac sac cac ctc ggt ccc 3'
```
\*Vλ 5' sense Primers
```
                        (SEQ ID NO: 35)
RSCL1       5' ggg ccc agg cgg ccg agc tcg tgc
            tga ctc agt cgc cct c 3'
```
\*Vλ 3' reverse Primers
```
                        (SEQ ID NO: 36)
RHybL-B     5' aga tgg tgc agc cac agt tcg gcc
            tgt gac ggt cag ctg ggt ccc 3'
```
\*VH 5' sense Primers
```
                        (SEQ ID NO: 37)
RHyVH1      5' gct gcc caa cca gcc atg gcc cag
            tcg gtg gag gag tcc rgg 3'

(SEQ ID NO: 38)
RHyVH2      5' gct gcc caa caa gcc atg gcc cag
            tcg gtg aag gag tcc gag 3'

(SEQ ID NO: 39)
RHyVH3      5' gct gcc caa cca gcc atg gcc cag
            tcg ytg gag gag tcc ggg 3'
```

```
                        (SEQ ID NO: 40)
RHyVH4      5' gct gcc caa cca gcc atg gcc cag
            sag cag ctg rtg gag tcc gg 3'
```
\*VH 3' reverse Primers
```
                        (SEQ ID NO: 41)
RHyIgGCH1-B 5' cga tgg gcc ctt ggt gga ggc tga
            rga gay ggt gac cag ggt gcc 3'
```
\*Primer for Amplification of the Human Cκ Region and the pelB Leader Sequence from a Cloned Human Fab
```
                        (SEQ ID NO: 42)
HKC-F(sense)    5' cga act gtg gct gca cca tct gtc
                3'

(SEQ ID NO: 43)
Lead-B(reverse) 5' ggc cat ggc tgg ttg ggc agc 3'
```
\*Primers for Amplification of the Human CH1 chain from a Cloned Human Fab
```
                        (SEQ ID NO: 44)
HIgGCH1-F(sense) 5' aga agc gta gtc cgg aac gtc 3'

(SEQ ID NO: 45)
dpseq(reverse)   5' aga agc gta gtc cgg aac gtc 3'
```

Example 30-2

The Second Round PCR Primer Sets

\*Primers for PCR Assembly of Rabbit VL Sequences with the Human CK PCR Product
```
                        (SEQ ID NO: 46)
RSC-F(sense)    5' gag gag gag gag gag gag gcg ggg
                ccc agg cgg ccg agc tc 3'

(SEQ ID NO: 47)
Lead-B(reverse) 5' ggc cat ggc tgg ttg ggc agc 3'
```
\*Primers for PCR Assembly of Rabbit VH Sequences with the Human CH1 PCR Product
```
                        (SEQ ID NO: 48)
lead VH(sense)  5' gct gcc caa cca gcc atg gcc 3'

(SEQ ID NO: 49)
dpseq(reverse)  5' aga agc gta gtc cgg aac gtc 3'
```

Example 30-3

The Third Round PCR Primer Sets

\*Primers for PCR Assembly of Chimeric Light-chain Sequences whth Chimeric Heavy-chain(Fd) Sequences
```
                        (SEQ ID NO: 50)
RSC-F(sense)    5' gag gag gag gag gag gag gcg ggg
                ccc agg cgg ccg agc tc 3'

(SEQ ID NO: 51)
dp-EX(reverse)  5' gag gag gag gag gag gag aga agc
                gta gtc cgg aac gtc 3'
```

The resulting PCR products digested with SfiI were ligated into phagemid vector pComb3X (gene bank AF268281) and transformed into XL1-Blue/F'. The phage library was obtained from the overnight culture media after absorption of helper phage VSCM13, followed by the addition of PEG and NaCl.

Example 31

Panning of Fab Libraries for Anti-Bst2 or Anti-Damp1 Antibodies

A Total of four rounds of panning were performed. For high affinity antibody clone to Bst2 and Damp1, DYNABEADS® (Dynal, Cat. No. 143.01) panning method using obtained chimeric Fab phage library was used.

DYNABEADS® M270, Epoxy were coated with Bst2 decoy, Damp1 decoy or bovine serum albumin (BSA) for 16~24 hr at 37° C. Bst2 decoy coated beads were washed with PBS (1.06 mM potassium phosphate monobasic, 155.17 mM sodium chloride, 2.97 mM sodium phosphate dibasic, pH 7.4) and 0.5% TWEEN® 20 in PBS and then suspended in 0.5% BSA in PBS. For removal of nonspecific binding, Bst2 phage library were preincubated with BSA coated beads. The precleared phage pools were incubated with Bst2-beads for 2 hours at room temperature and washed with 0.5% TWEEN® 20 in PBS at several times by the magnetic separation method for removal of nonspecific binding phages. Specific binding phage were eluted by the incubation of 0.1M sodium citrate (pH 3.0, 0.45 ml) for 10 min twice and neutralized with the addition of 1M Tris-HCl (pH 9.5, 0.1 ml). The eluted phages were infected to logarithmically growing XL1-Blue F' and amplified by helper phage VSCM13 for overnight. Phages were prepared by the precipitation with 4% PEG and 3% NaCl (w/v), and then suspended with 1% BSA and 0.02% NaN₃ in PBS buffer. The output phage pool of each round was monitored by phage ELISA in using anti-HA-Horseradish peroxidase (Roche, Cat No 2 013 819). The Damp1 decoy specific phage pools were selected as the same protocol as Bst2 specific ones described above.

Example 32

Screening of Fab Libraries for Antibodies Specific for Both Bst2 and Damp1

For selection of clones reactive to both Bst2 and Damp1, single phage clone was inoculated in 2xYT broth containing 30 µg/ml tetracyclin, 50 ug/ml carbenicillin, and 1% glucose and cultured at 37° C. overnight. Culture supernatant was sub-cultured in 2xYT broth containing 30 µg/ml tetracyclin, 50 µg/ml carbenicillin on a 96 deep-well plate and amplified in using helper phage VSCM13 and kanamycin. After overnight culture, the phage supernatant was obtained by centrifugation for 30 min at 3000 rpm and used in the Bst2/damp1 binding assay in an ELISA format.

Figure 29:
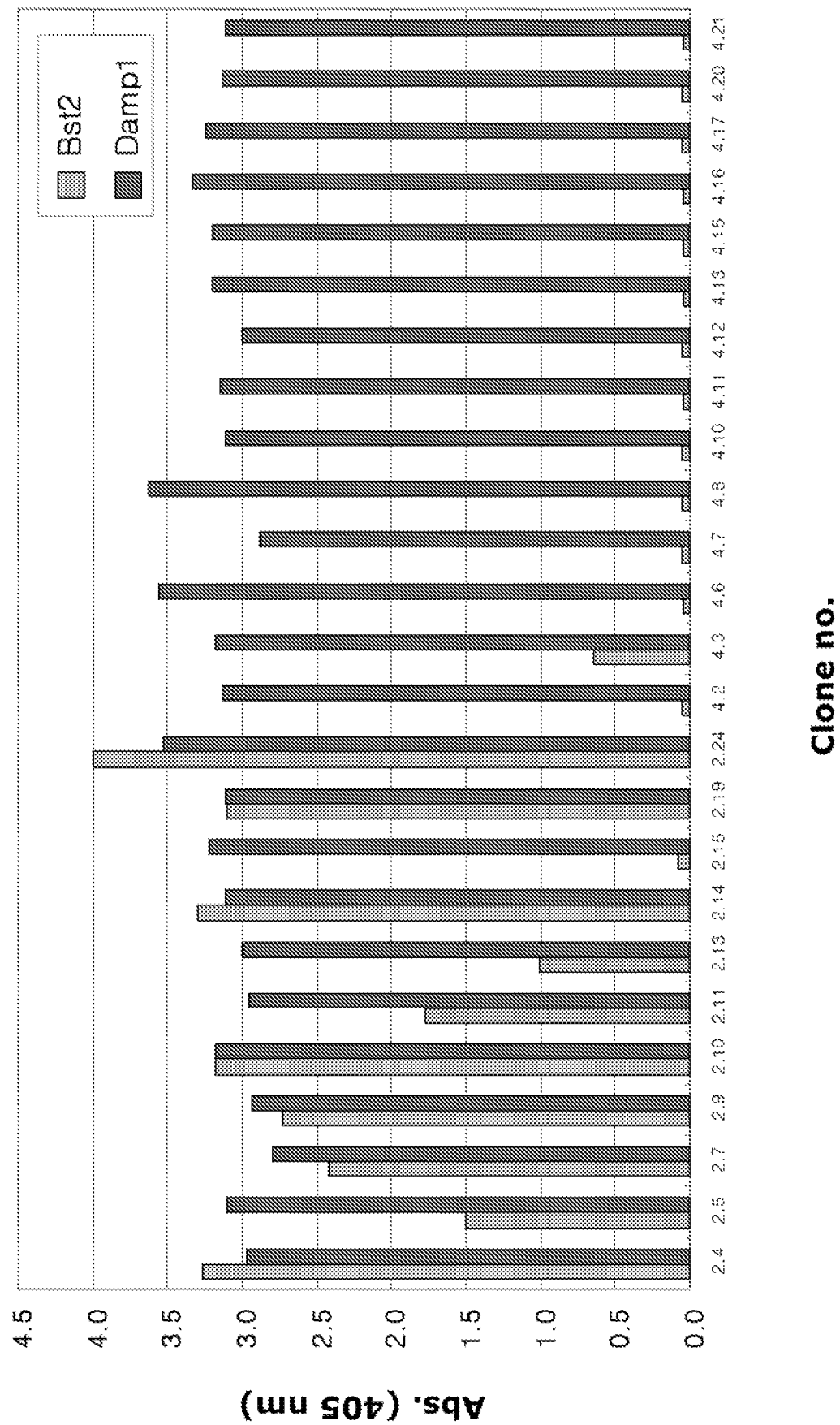
FIG. 29 shows binding of phage clones to Bst2/Damp1 decoy.

Each well on a 96 well MAXISORP™ plate (Nunc) was coated with 1 µg of Bst2 decoy or Damp1 decoy at 4° C. overnight and blocked by incubation of 5% BSA in TBS (50 mM Tris-HCl, 150 mM NaCl, pH 7.4) for 2 hr 37° C. Then, 100 µl of phage supernatant was subsequently added for 1 hr 37° C. Each well was washed with 0.05% TWEEN® 20 in TBS (7.4 pH) and added with 100 µl of horseradish peroxidase conjugated anti-HA antibody for 1 hr at 37° C. After washing as above, 200 µl OPD (o-Phenylenediamine dihydrochloride, 0.4 mg/ml, Sigma) solution was added, followed by the addition of 50 ul of 3M sulfuric acid (50 µl) as a stop solution. Results are shown in FIG. 29.

Example 33

Expression of Selected Antibodies

Positive phage clones obtained above were analyzed by DNA sequencing and chosen based on sequence alignment. See FIG. 30.

Table 1 below shows the CDR1, CDR2 and CDR3 regions for the heavy chain variable regions.

TABLE 1

| | Heavy chain variable region complementarity determining regions | | |
|---|---|---|---|
| | CDR1 | CDR2 | CDR3 |
| 2-15 | NSGMS (SEQ ID NO: 68) | LINSYGTTYYASWAKG (SEQ ID NO: 69) | GAGSSYGL (SEQ ID NO: 70) |
| 2-14 | SYEMN (SEQ ID NO: 71) | IIRSDGSTYYASWAKS (SEQ ID NO: 72) | DLGYSNDV (SEQ ID NO: 73) |
| 2-10 | SYMIY (SEQ ID NO: 74) | FIYGSGDTYYATWAKG (SEQ ID NO: 75) | SSGWGYGLDL (SEQ ID NO: 76) |
| 2-4 | SYHMQ (SEQ ID NO: 77) | FIDTVGSAYYASWAKG (SEQ ID NO: 78) | DSGYSIGTL (SEQ ID NO: 79) |
| 2-5 | SYAMI (SEQ ID NO: 80) | IIRSSGNTYYASWAKG (SEQ ID NO: 81) | DSGYSFGL (SEQ ID NO: 82) |
| 2-7 | SHEMN (SEQ ID NO: 83) | IINSYANTYYAGWAKS (SEQ ID NO: 84) | DLGYSSDI (SEQ ID NO: 85) |
| 2-9 | SYEMS (SEQ ID NO: 86) | FISTSGNTYYASWAKG (SEQ ID NO: 87) | GPAKSGYGTRLDL (SEQ ID NO: 88) |
| 2-11 | SYRMG (SEQ ID NO: 89) | FINNYGSAYYASWAKS (SEQ ID NO: 90) | ESYSYGYAYDI (SEQ ID NO: 91) |
| 2-13 | GYAMG (SEQ ID NO: 92) | IIGTSDTTYYASWAKG (SEQ ID NO: 93) | SPGGSADL (SEQ ID NO: 94) |

TABLE 1-continued

Heavy chain variable region complementarity determining regions

| | CDR1 | CDR2 | CDR3 |
|---|---|---|---|
| 2-19 | SYEMN (SEQ ID NO: 95) | IIRSDGSTYYASWAKS (SEQ ID NO: 96) | DLGYSNDV (SEQ ID NO: 97) |
| 2-24 | TYEMN (SEQ ID NO: 98) | IINSAGTTYYASWAKS (SEQ ID NO: 99) | DLGYSSDI (SEQ ID NO: 100) |

Table 2 below shows the CDR1, CDR2 and CDR3 regions for the kappa chain variable regions.

TABLE 2

Kappa chain variable region complementarity determining regions

| | CDR1 | CDR2 | CDR3 |
|---|---|---|---|
| 2-15 | QASQSIGSNLA (SEQ ID NO: 101) | ASNLAS (SEQ ID NO: 102) | LGSDSSWDTV (SEQ ID NO: 103) |
| 2-14 | QASQNIGINLA (SEQ ID NO: 104) | YASDLAS (SEQ ID NO: 105) | LGTYGSGDRA (SEQ ID NO: 106) |
| 2-10 | QASQSINVWLS (SEQ ID NO: 107) | QASKLAS (SEQ ID NO: 108) | LGIYNDIDTA (SEQ ID NO: 109) |
| 2-4 | QATKNIGINLA (SEQ ID NO: 110) | YASDLAS (SEQ ID NO: 111) | LGSYGSGDRA (SEQ ID NO: 112) |
| 2-5 | QASKNIGINLA (SEQ ID NO: 113) | YASDLAS (SEQ ID NO: 111) | LGSYGSGDRA (SEQ ID NO: 112) |
| 2-7 | QASQNIGINLA (SEQ ID NO: 104) | YASDLAS (SEQ ID NO: 111) | LGSYGSGDRA (SEQ ID NO: 112) |
| 2-9 | QASQNIGINLA (SEQ ID NO: 104) | YASDLAS (SEQ ID NO: 111) | LGTYGSGDRA (SEQ ID NO: 106) |
| 2-11 | RASQIIGINLA (SEQ ID NO: 114) | YASDLAS (SEQ ID NO: 111) | LGTYGSGVRA (SEQ ID NO: 115) |
| 2-13 | QASQNIGINLA (SEQ ID NO: 104) | YASDLAS (SEQ ID NO: 111) | LGTYGSGVRA (SEQ ID NO: 115) |
| 2-19 | QASQNIGINLA (SEQ ID NO: 104) | YTSDLAS (SEQ ID NO: 116) | LGTYGSGVRA (SEQ ID NO: 115) |
| 2-24 | QASQNIGINLA (SEQ ID NO: 104) | YASDLAS (SEQ ID NO: 111) | LGTYGSGDRA (SEQ ID NO: 106) |

For expression in whole IgG1 form, each phage Fab DNA fragment was cloned into the expression vector, pCDH and pCDK, derived from pCDNA 3.1 (Invitrogen).

pCDH is an intermediate cloning vector for the expression of a full-length IgG heavy chain. The CH1-CH2-CH3 domains of an IgG heavy chain was PCR amplified from a whole blood cell cDNA library (Clontech) using primers R1-CH1 and CH3-Not1 cloned into the EcoR1, Not1 site of pcDNA3.1 following EcoR1 and Not1 restriction digestion. A secretable full length IgG heavy chain was reconstructed by fusing the secretion signal for tPA 5' to the heavy chain variable region through overlap PCR cloning by first PCRing the tPA signal peptide with primers R1-tPA5 and tPA3 from the library used above and PCRing the variable region and CH1 from the phagemid used to express the Fab fragment with Heavy_CH1_Rev and the primer specific for the variable region (Ra_Hv_Fw1 through Ra_Hv_Fw9); these two PCR fragment were then fused through an overlap PCR reaction with primers R1-tPA5 and Heavy_CH1_Rev, digested with EcoR1 and Age1 and cloned into pCDH digested with the same enzymes.

pCDK is an intermediate vector for the expression of the IgG light chain made by PCR cloning the light chain with primers H3-light and light-Xba1, digesting the PCR product with HindIII and XbaI and cloning into pcDNA3.1 digested with the same enzymes. A secretable full length IgG light chain was reconstructed by fusing the secretion signal for tPA 5' to the light chain variable region through overlap PCR cloning by first PCRing the tPA signal peptide with primers H3-tPA5 and tPA3 from the library used above and PCRing the variable region and CK from the phagemid used to express the Fab fragment with specific primer pairs for the variable regions (Ra_Kp_F1 through 6 and Ra_Kp_Rva through d); these two PCR fragment were then fused through an overlap PCR reaction with primers H3-tPA5 and the specific light chain 3' primer, digested with HinDIII and BsiWI and cloned into pCDK digested with the same enzymes.

```
                                              (SEQ ID NO: 52)
R1-CH1          5' cgcgaattcgcctccaccaagggcccatcg 3'

(SEQ ID NO: 53)
CH3-Not1        5' ggcggccgctcatttacccggga 3'

(SEQ ID NO: 54)
R1-tPA5         5' cgcgaattcaggacctcaccatgggatgg 3'

(SEQ ID NO: 55)
tPA3            5' ggagtggacacctgtagct 3'

(SEQ ID NO: 56)
Heavy_CH_1_Rev  5' ccacgctgctgagggagtagagtc 3'

(SEQ ID NO: 57)
Ra_Hv_F1:       5' gcaacagctacaggtgtccactcc
                   cagcagcagctgatggag 3' 42mer (SEQ ID NO: 58)
Ra_Hv_F2:       5' gcaacagctacaggtgtccactcc
                   caggagcagctgatggagt 3' 43mer (SEQ ID NO: 59)
Ra_Hv_F3:       5' gcaacagctacaggtgtccactcc
                   caggagcagctggtggagt 3' 43mer (SEQ ID NO: 60)
Ra_Hv_F4:       5' gcaacagctacaggtgtccactcc
                   cagtcggtgaaggagtccg 3' 43mer (SEQ ID NO: 61)
Ra_Hv_F5:       5' gcaacagctacaggtgtccactcc
                   cagtcgttggaggagtccg 3' 43mer (SEQ ID NO: 62)
Ra_Hv_F6:       5' gcaacagctacaggtgtccactcc
                   cagtcggtggaggagtcc 3' 42mer (SEQ ID NO 63)
Ra_Hv_F7:       5' gcaacagctacaggtgtccactcc
                   cagcggttggaggagtcc 3' 42mer (SEQ ID NO: 64)
Ra_Hv_F8:       5' gcaacagctacaggtgtccactcc
                   cagcagcagctggtggag 3' 42mer (SEQ ID NO: 65)
Ra_Hv_F9:       5' gcaacagctacaggtgtccactcc
                   cagtcgctggaggagtcc 3' 42mer (SEQ ID NO: 66)
H3-light:       5' gcgaagcttcgaactgtggctgcaccatct 3'

(SEQ ID NO: 67)
light-Xba1:     5' gcgtctagattaacactctcccctgttga 3'

(SEQ ID NO: 117)
H3-tPA5:        5' gcgaagcttaggacctcaccatgggatgg 3'

(SEQ ID NO: 118)
Ra_Kp_F1:       5' gcaacagctacaggtgtccactcc
                   gagctcgatatgacccagac 3' 44mer (SEQ ID NO: 119)
Ra_Kp_F2:       5' gcaacagctacaggtgtccactcc
                   gagctcgtgctgaaccca 3' 42mer (SEQ ID NO: 120)
Ra_Kp_F3:       5' gcaacagctacaggtgtccactcc
                   gagctcgtgatgacccagac 3' 44mer (SEQ ID NO: 154)
Ra_Kp_F4:       5' gcaacagctacaggtgtccactcc
                   gagctcgatctgacccagac 3' 44mer (SEQ ID NO: 122)
Ra_Kp_Rva:      5' cgccgtacg taggatctccagctcggtcc 3'
                   29mer (SEQ ID NO: 123)
Ra_Kp_Rvb:      5' cgccgtacg tttgatttccacattggtgcc
                   3' 30mer (SEQ ID NO: 124)
Ra_Kp_Rvc:      5' cgccgtacg tttgacgaccacctcggtc 3'
                   28mer (SEQ ID NO: 125)
Ra_Kp_Rvd:      5' cgccgtacg taggatctccagctcggtccc
                   3' 30mer
```

For expression in whole IgG1 form, each phage Fab DNA fragment was cloned into the expression vector, pCDNA 3.1 (Invitrogen).

In order to express monoclonal antibodies (mAb, IgG1) selected above, a vector DNA was transiently or stably introduced into mammalian cells. Transient transfection was performed by calcium phosphate ($CaPO_4$) precipitation, as follows. One day before transfection, $7 \times 10^6$ cells of 293T (ATCC) were seeded and cultured onto a 150-mm cell culture plate. One hour before transfection, the culture medium was exchanged with IMDM medium (Cambrex) supplemented with 2% fetal bovine serum (GIBCO-BRL). TE buffer (1 mM Tris, 0.1 mM EDTA, pH 8.0) containing 75 µg of DNA and 250 mM calcium in a volume of 1.5 ml, was mixed with the equal volume of HEPES buffer (50 mM HEPES, 140 mM NaCl, 1.4 mM $Na_2HPO_4$, pH 7.05). The mixture was incubated for about 1 min at room temperature and was applied to the pre-cultured cells. The cells were incubated in a $CO_2$ incubator at 37° C. for 6 hrs. After the DNA/calcium solution was removed, the cells were added with serum-free medium and further cultured for 72 hrs or longer, and then the culture medium was harvested. Each mAb was purified from the culture media in using Protein A affinity chromatography (Amersham Biosciences, MabSelect). Culture media were loaded on protein A-packed column previously equilibrated with PBS buffer (1.06 mM potassium phosphate monobasic, 155.17 mM sodium chloride, 2.97 mM sodium phosphate dibasic, pH 7.4). The column was washed with PBS buffer for removing the contaminants about 20 column volumes. Bound antibodies were eluted by low pH buffer, such as 50 mM glycine-HCl using a step gradient and neutralized with the equal volume of 1M Tris (pH 8.0). The purified protein samples were subject to gel electrophoresis in 4-20% native PAGE (4-20% native PAGE, Invitrogen). See FIG. 31 for the purified proteins in gel.

Example 34

Competitive Binding Assay (in vitro)

Competitive inhibition of mAbs specific for Bst2 or Damp1 in the binding between BST2 decoy and cells was measured as follows. Flat-bottomed 96-well plates were coated with 100 mL of Bst2 decoy (50 mg) with sodium bicarbonate (100 mM, pH 9.5) for 2 hrs at 37° C. The plates were washed with PBS (pH 7.4) and incubated with 1% bovine serum albumin (BSA) at 25° C. After a rinse with PBS (pH 7.4) containing 1 mM $CaCl_2$ and 0.5 mM $MgCl_2$, 50 mL of a $1 \times 10^6$/ml U937 cell suspension were added to each Bst2-coated well. Before the addition, cells were pre-incubated with each mAb for 2 hrs at 37° C. Total adhesion cell counts were assessed after incubation for 2 hrs at 37° C.

Non-adherent cells were removed by two gentle washes with RPMI1640 media (Gibco-BRL) and residual attached cells were fixed with 2% paraformaldehyde for 20 minutes, washed, and stained with 0.5% crystal violet. After 30 minutes at 25° C., the plates were washed with PBS and adherent cells were counted.

Example 35

The Effect of mAbs on a Mouse Model of Asthma

A mouse model of asthma was prepared by sensitizing mice (BALB/c, 8 weeks) with ovalbumin. In detail, mice were initially sensitized for five continuous days by intranasal injection of ovalbumin. After three weeks, mice were intranasally sensitized again with ovalbumin for five continuous days. One week after the secondary sensitization, mice were challenged intranasally with ovalbumin three times every 24 hr to induce asthma. Herein, each mAb was intravenously injected into mice 24 hour before challenge with ovalbumin, and was injected to mice 30 min before the first challenge and the last challenge of ovalbumin. Three days after the last injection, serum samples, lung tissues, and the like were collected from mice.

When mAb clones specific for Bst2/Damp1 was injected in a dose of 10 mg/kg into a mouse model of asthma which was induced by sensitization and challenge with ovalbumin, changes in the number of neutrophils, eosinophils, macrophages, lymphocytes and other cell types were assessed. Three days after the last challenge of ovalbumin, mice were sacrificed to expose the lung and other organs. After the trachea was dissected at its upper part, a cannula was carefully inserted into the trachea and bronchoalveolar lavage was washed with physiological saline prewarmed to 37° C. The lavage fluids were collected, pooled, and centrifuged at 4° C. The sedimented cells were used for total cell counting or different cell counting under a microscope. In bronchoalveolar lavage fluid collected 72 hrs after sensitization with ovalbumin, the total number of cells, including neutrophils, eosinophils, macrophages and lymphocytes, increased in comparison with a control pretreated with physiological saline. When ovalbumin-sensitized mice were treated with a Bst2 soluble fragment, the total cell number remarkably decreased fluid and, especially, the number of neutrophils, eosinophils and lymphocytes except for macrophage decreased in bronchoalveolar lavage (BAL). When ovalbumin-sensitized mice are treated with each mAb, the total cell number and the number of each cell type (neutrophils, eosinophils and lymphocytes) remarkably decreased in bronchoalveolar lavage fluid.

When a Bst2 decoy or Fc fusion protein is injected into a mouse model of asthma which was induced by sensitization and challenge with ovalbumin, expression levels of cytokines (interleukin-4 (IL-4), interleukin-5 (IL-5) and interleukin-13 (IL-13)) are measured, as follows. After sampling BAL fluid, cytosolic proteins from lung tissue are isolated using lysis buffer containing NP-40. The isolated proteins are subject to immunoblot with several cytokine antibodies: anti-IL-4 antibody (Setotec Inc.), anti-IL-5 antibody (Santa Cruz Inc.), anti-IL-13 antibody and anti-actin antibody (Sigma Inc.). The levels of cytokines, such as IL-4, IL-5 and IL-13, increase in the lung tissue of mice with asthma induced by sensitization and challenge with ovalbumin. The levels of cytokines, such as IL-4, IL-5 and IL-13, increase in the lung tissue of mice with asthma induced by sensitization and challenge with ovalbumin. Also, when ovalbumin-sensitized asthmatic mice are injected with each mAb specific for Bst2/Damp1, cytokine levels decrease under the treatment of mAb in a dose-dependent manner. This indicates that the Damp-1 specific mAb has a therapeutic effect on asthma.

All of the references cited herein are incorporated by reference in their entirety.

Those skilled in the art will recognize, or be able to ascertain using no more than routine experimentation, many equivalents to the specific embodiments of the invention specifically described herein. Such equivalents are intended to be encompassed in the scope of the claims.

What is claimed is:

1. A method of reducing inflammation in a subject suffering from asthma comprising administering a composition comprising a bone marrow stromal cell antigen 2 (Bst2) antagonist to a site of the inflammation, wherein said Bst2 antagonist comprises a soluble portion of Bst2, which comprises an extracellular portion of Bst2 or a fragment of the extracellular portion, in an amount effective to inhibit binding between a first leukocyte and a second leukocyte or an endothelial cell, wherein the extracellular portion is shown in amino acid positions 44 to 180 of SEQ ID NO:3.

2. The method according to claim 1, wherein the Bst2 antagonist is a Fc chimeric or fusion construct, an albumin chimeric or fusion construct, or linked to a non-proteinaceous polymer.

3. A method of treating asthma in a subject comprising administering a composition comprising a bone marrow stromal cell antigen 2 (Bst2) antagonist to the person in need thereof, wherein said Bst2 antagonist comprises a soluble portion of Bst2, which comprises an extracellular portion of Bst2 or a fragment of the extracellular portion, in an amount effective to inhibit binding between a first leukocyte and a second leukocyte or an endothelial cell, wherein the extracellular portion is shown in amino acid positions 44 to 180 of SEQ ID NO:3.

4. The method according to claim 1, wherein the extracellular portion is shown in amino acid positions 44 to 159 of SEQ ID NO:3.

5. The method according to claim 1, wherein said first leukocyte and the second leukocyte or the endothelial cell are located either at a site of inflammation or at a site distant from inflammation but can transmit inflammatory and immune cytokines or other inflammatory signals to a site of inflammation.

6. The method according to claim 3, wherein the extracellular portion is shown in amino acid positions 44 to 159 of SEQ ID NO:3.

7. The method according to claim 3, wherein the Bst2 antagonist is a Fc chimeric or fusion construct, an albumin chimeric or fusion construct, or linked to a non-proteinaceous polymer.

8. The method according to claim 3, wherein said first leukocyte and the second leukocyte or the endothelial cell are located either at a site of inflammation or at a site distant from inflammation but can transmit inflammatory and immune cytokines or other inflammatory signals to a site of inflammation.

* * * * *

SEQUENCE LISTING

```
<160> NUMBER OF SEQ ID NOS: 171

<210> SEQ ID NO 1
<211> LENGTH: 983
<212> TYPE: DNA
<213> ORGANISM: Homo sapiens

<400> SEQUENCE: 1
gtggaattca tggcatctac ttcgtatgac tattgcagag tgcccatgga agacggggat      60
aagcgctgta agcttctgct ggggatagga attctggtgc tcctgatcat cgtgattctg     120
ggggtgccct tgattatctt caccatcaag gccaacagcg aggcctgccg ggacggcctt     180
cgggcagtga tggagtgtcg caatgtcacc catctcctgc aacaagagct gaccgaggcc     240
cagaagggct tcaggatgt ggaggcccag gccgccacct gcaaccacac tgtgatggcc     300
ctaatggctt ccctggatgc agagaaggcc caaggacaaa agaaagtgga ggagcttgag     360
ggagagatca ctacattaaa ccataagctt caggacgcgt ctgcagaggt ggagcgactg     420
agaagagaaa accaggtctt aagcgtgaga atcgcggaca gaagtacta ccccagctcc     480 caggactcca gctccgctgc ggcgcccag ctgctgattg tgctgctggg cctcagcgct     540
```

-continued

```
ctgctgcagt gagatcccag gaagctggca catcttggaa ggtccgtcct gctcggcttt      600
tcgcttgaac attcccttga tctcatcagt tctgagcggg tcatgggca acacggttag       660 cggggagagc acgggtagc cggagaaggg cctctggagc aggtctggag gggccatggg       720
gcagtcctgg gtgtggggac acagtcgggt tgacccaggg ctgtctccct ccagagcctc     780
cctccggaca tgagtcccc cctcttgtct cccaccctga gattgggcat ggggtgcggt      840 gtgggggca tgtgctgcct gttgttatgg gtttttttg cggggggggt tgctttttc       900 tggggtcttt gagctccaaa aaataaacac ttcctttgag ggagagcaaa aaaaaaaaa      960 aaaaaaaaa aaaaaaaaaa aaa                                              983
```

<210> SEQ ID NO 2
<211> LENGTH: 900
<212> TYPE: DNA
<213> ORGANISM: Mus musculus
<400> SEQUENCE: 2

```
gacgcgtggg cggacgcgtg ggcggacgcg tggggacgga tcacatggcg ccctctttct     60
atcactatct gcccgtgccc atggatgaga tgggggggaa gcaaggatgg ggcagccacc    120
ggcagtggct gggggccgcg atcttggtgg tcctgttcgg ggttacctta gtcatcctga    180
caatctactt cgccgtcaca gcgaacagcg tggcctgtag agacgggttg cgagcgcagg    240
ctgagtgccg gaacaccacg cacctgttgc agcgccagct cacccgcacc caggacagtc    300
tgctgcaggc cgagacacag gcaaactcct gcaacctgac cgtggtgacc cttcaggagt    360
ccctggagaa gaaggtgtct caagccctgg agcagcaggc ccgcatcaag gagcttgaga    420
atgaagtcac gaagctgaac caggagctgg agaatctgag gatccaaaag gagacttcta    480
gcacagtgca ggtgaactct ggcagctcca tggtggtctc cagcctactg gtgctcaaag    540
tgtcactgtt cctgctcttt tgaggactca ttagttggca ggtcacagtt gtttgaagtc    600
actatgggtc atagtgactc tggagaggtc ctggcagccc tgaggatgtg gaaaccacta    660
gggggctcca gattgggtct tcctccgcag aactttagga ctggggagtg gggagggagt    720
tctgctttat tgcttttgca gttattgggg ggggtcacat atttctggtg tctttgacct    780
ggaaaaataa agtaatttaa aaaaaaaaa aaaaaaaaa aaaaaaaaa aaaaaaaaa       840 aaaaaaaaa aaaaaaaaaa aaaaaaaaa aaaaaaaaa aaaaaaaaa aaaaaaaaa       900
```

<210> SEQ ID NO 3
<211> LENGTH: 180
<212> TYPE: PRT
<213> ORGANISM: Homo sapiens
<400> SEQUENCE: 3

```
Met Ala Ser Thr Ser Tyr Asp Tyr Cys Arg Val Pro Met Glu Asp Gly
  1               5                  10                  15

Asp Lys Arg Cys Lys Leu Leu Leu Gly Ile Gly Ile Leu Val Leu Leu
                 20                  25                  30

Ile Ile Val Ile Leu Gly Val Pro Leu Ile Ile Phe Thr Ile Lys Ala
             35                  40                  45

Asn Ser Glu Ala Cys Arg Asp Gly Leu Arg Ala Val Met Glu Cys Arg
         50                  55                  60

Asn Val Thr His Leu Leu Gln Gln Glu Leu Thr Glu Ala Gln Lys Gly
     65                  70                  75                  80

Phe Gln Asp Val Glu Ala Gln Ala Ala Thr Cys Asn His Thr Val Met
```

85                  90                  95
Ala Leu Met Ala Ser Leu Asp Ala Glu Lys Ala Gln Gly Gln Lys Lys
                100                 105                 110

Val Glu Leu Glu Gly Glu Ile Thr Thr Leu Asn His Lys Leu Gln
        115                 120                 125

Asp Ala Ser Ala Glu Val Glu Arg Leu Arg Arg Glu Asn Gln Val Leu
    130                 135                 140

Ser Val Arg Ile Ala Asp Lys Lys Tyr Tyr Pro Ser Ser Gln Asp Ser
145                 150                 155                 160

Ser Ser Ala Ala Ala Pro Gln Leu Leu Ile Val Leu Gly Leu Ser
                165                 170                 175

Ala Leu Leu Gln
        180

<210> SEQ ID NO 4
<211> LENGTH: 172
<212> TYPE: PRT
<213> ORGANISM: Mus musculus

<400> SEQUENCE: 4

Met Ala Pro Ser Phe Tyr His Tyr Leu Pro Val Pro Met Asp Glu Met
1               5                   10                  15

Gly Gly Lys Gln Gly Trp Gly Ser His Arg Gln Trp Leu Gly Ala Ala
            20                  25                  30

Ile Leu Val Val Leu Phe Gly Val Thr Leu Val Ile Leu Thr Ile Tyr
        35                  40                  45

Phe Ala Val Thr Ala Asn Ser Val Ala Cys Arg Asp Gly Leu Arg Ala
    50                  55                  60

Gln Ala Glu Cys Arg Asn Thr Thr His Leu Leu Gln Arg Gln Leu Thr
65                  70                  75                  80

Arg Thr Gln Asp Ser Leu Leu Gln Ala Glu Thr Gln Ala Asn Ser Cys
                85                  90                  95

Asn Leu Thr Val Val Thr Leu Gln Glu Ser Leu Glu Lys Lys Val Ser
                100                 105                 110

Gln Ala Leu Glu Gln Gln Ala Arg Ile Lys Glu Leu Glu Asn Glu Val
            115                 120                 125

Thr Lys Leu Asn Gln Glu Leu Glu Asn Leu Arg Ile Gln Lys Glu Thr
        130                 135                 140

Ser Ser Thr Val Gln Val Asn Ser Gly Ser Ser Met Val Val Ser Ser
145                 150                 155                 160

Leu Leu Val Leu Lys Val Ser Leu Phe Leu Leu Phe
                165                 170

<210> SEQ ID NO 5
<211> LENGTH: 18
<212> TYPE: DNA
<213> ORGANISM: Artificial sequence
<220> FEATURE:
<223> OTHER INFORMATION: Primer

<400> SEQUENCE: 5
ttttctcttc tcagtctc                                                18

<210> SEQ ID NO 6
<211> LENGTH: 18
<212> TYPE: DNA
<213> ORGANISM: Artificial sequence
<220> FEATURE:

-continued

<223> OTHER INFORMATION: Primer

<400> SEQUENCE: 6
gcatctactt cgtatgac                                                         18

<210> SEQ ID NO 7
<211> LENGTH: 21
<212> TYPE: DNA
<213> ORGANISM: Artificial sequence
<220> FEATURE:
<223> OTHER INFORMATION: Target sequence

<400> SEQUENCE: 7
aagcgtgaga atcgcggaca a                                                     21

<210> SEQ ID NO 8
<211> LENGTH: 19
<212> TYPE: RNA
<213> ORGANISM: Artificial sequence
<220> FEATURE:
<223> OTHER INFORMATION: Sense oligomer

<400> SEQUENCE: 8
uuguccgcga uucucacgc                                                        19

<210> SEQ ID NO 9
<211> LENGTH: 19
<212> TYPE: DNA
<213> ORGANISM: Artificial sequence
<220> FEATURE:
<223> OTHER INFORMATION: Antisense oligomer

<400> SEQUENCE: 9
gcgtgagaat cgcggacaa                                                        19

<210> SEQ ID NO 10
<211> LENGTH: 24
<212> TYPE: DNA
<213> ORGANISM: Artificial sequence
<220> FEATURE:
<223> OTHER INFORMATION: Primer

<400> SEQUENCE: 10
ctcccaggac gagcccaaat cttg                                                  24

<210> SEQ ID NO 11
<211> LENGTH: 24
<212> TYPE: DNA
<213> ORGANISM: Artificial sequence
<220> FEATURE:
<223> OTHER INFORMATION: Primer

<400> SEQUENCE: 11
ggcggccgct catttacccg ggga                                                  24

<210> SEQ ID NO 12
<211> LENGTH: 24
<212> TYPE: DNA
<213> ORGANISM: Artificial sequence
<220> FEATURE:
<223> OTHER INFORMATION: Primer

<400> SEQUENCE: 12
ctcccaggac cgtacggtgg ctgc                                                  24

```
<210> SEQ ID NO 13
<211> LENGTH: 24
<212> TYPE: DNA
<213> ORGANISM: Artificial sequence
<220> FEATURE:
<223> OTHER INFORMATION: Primer

<400> SEQUENCE: 13
ggcggccgct taacactctc ccct                                              24

<210> SEQ ID NO 14
<211> LENGTH: 24
<212> TYPE: DNA
<213> ORGANISM: Artificial sequence
<220> FEATURE:
<223> OTHER INFORMATION: Primer

<400> SEQUENCE: 14
ctcccaggac gcctccacca aggg                                              24

<210> SEQ ID NO 15
<211> LENGTH: 24
<212> TYPE: DNA
<213> ORGANISM: Artificial sequence
<220> FEATURE:
<223> OTHER INFORMATION: Primer

<400> SEQUENCE: 15
ggcggccgct catttaccca gaga                                              24

<210> SEQ ID NO 16
<211> LENGTH: 24
<212> TYPE: DNA
<213> ORGANISM: Artificial sequence
<220> FEATURE:
<223> OTHER INFORMATION: Primer

<400> SEQUENCE: 16
cgctcgagac agccatcatg gatg                                              24

<210> SEQ ID NO 17
<211> LENGTH: 24
<212> TYPE: DNA
<213> ORGANISM: Artificial sequence
<220> FEATURE:
<223> OTHER INFORMATION: Primer

<400> SEQUENCE: 17
ctcccaggac gagcccaaat cttg                                              24

<210> SEQ ID NO 18
<211> LENGTH: 24
<212> TYPE: DNA
<213> ORGANISM: Artificial sequence
<220> FEATURE:
<223> OTHER INFORMATION: Primer

<400> SEQUENCE: 18
ttgggctcgt cctgggagct gggg                                              24

<210> SEQ ID NO 19
<211> LENGTH: 24
<212> TYPE: DNA
<213> ORGANISM: Artificial sequence
<220> FEATURE:
<223> OTHER INFORMATION: Primer
```

```
<400> SEQUENCE: 19
ggcggccgct catttacccg ggga                                          24

<210> SEQ ID NO 20
<211> LENGTH: 24
<212> TYPE: DNA
<213> ORGANISM: Artificial sequence
<220> FEATURE:
<223> OTHER INFORMATION: Primer

<400> SEQUENCE: 20
ctcccaggac cgtacggtgg ctgc                                          24

<210> SEQ ID NO 21
<211> LENGTH: 24
<212> TYPE: DNA
<213> ORGANISM: Artificial sequence
<220> FEATURE:
<223> OTHER INFORMATION: Primer

<400> SEQUENCE: 21
accgtacggt cctgggagct gggg                                          24

<210> SEQ ID NO 22
<211> LENGTH: 24
<212> TYPE: DNA
<213> ORGANISM: Artificial sequence
<220> FEATURE:
<223> OTHER INFORMATION: Primer

<400> SEQUENCE: 22
ggcggccgct taacactctc ccct                                          24

<210> SEQ ID NO 23
<211> LENGTH: 24
<212> TYPE: DNA
<213> ORGANISM: Artificial sequence
<220> FEATURE:
<223> OTHER INFORMATION: Primer

<400> SEQUENCE: 23
ctcccaggac gcctccacca aggg                                          24

<210> SEQ ID NO 24
<211> LENGTH: 24
<212> TYPE: DNA
<213> ORGANISM: Artificial sequence
<220> FEATURE:
<223> OTHER INFORMATION: Primer

<400> SEQUENCE: 24
gtggaggcgt cctgggagct gggg                                          24

<210> SEQ ID NO 25
<211> LENGTH: 24
<212> TYPE: DNA
<213> ORGANISM: Artificial sequence
<220> FEATURE:
<223> OTHER INFORMATION: Primer

<400> SEQUENCE: 25
ggcggccgct catttaccca gaga                                          24

<210> SEQ ID NO 26
<211> LENGTH: 24
```

```
<212> TYPE: DNA
<213> ORGANISM: Artificial sequence
<220> FEATURE:
<223> OTHER INFORMATION: Primer

<400> SEQUENCE: 26
catatttgga ctcgtcctgg gagc                                           24

<210> SEQ ID NO 27
<211> LENGTH: 28
<212> TYPE: DNA
<213> ORGANISM: Artificial sequence
<220> FEATURE:
<223> OTHER INFORMATION: Primer

<400> SEQUENCE: 27
ctcccaggac gagtccaaat atggtccc                                       28

<210> SEQ ID NO 28
<211> LENGTH: 28
<212> TYPE: DNA
<213> ORGANISM: Artificial sequence
<220> FEATURE:
<223> OTHER INFORMATION: Primer

<400> SEQUENCE: 28
ggcggccgct catttaccca gagacagg                                       28

<210> SEQ ID NO 29
<211> LENGTH: 38
<212> TYPE: DNA
<213> ORGANISM: Artificial sequence
<220> FEATURE:
<223> OTHER INFORMATION: Primer

<400> SEQUENCE: 29
gggcccaggc ggccgagctc gtgmtgaccc agactcca                            38

<210> SEQ ID NO 30
<211> LENGTH: 38
<212> TYPE: DNA
<213> ORGANISM: Artificial seqeunce
<220> FEATURE:
<223> OTHER INFORMATION: Primer

<400> SEQUENCE: 30
gggcccaggc ggccgagctc gatmtgaccc agactcca                            38

<210> SEQ ID NO 31
<211> LENGTH: 38
<212> TYPE: DNA
<213> ORGANISM: Artificial sequence
<220> FEATURE:
<223> OTHER INFORMATION: Primer

<400> SEQUENCE: 31
gggcccaggc ggccgagctc gtgatgaccc agactgaa                            38

<210> SEQ ID NO 32
<211> LENGTH: 42
<212> TYPE: DNA
<213> ORGANISM: Artificial sequence
<220> FEATURE:
<223> OTHER INFORMATION: Primer

<400> SEQUENCE: 32
```
agatggtgca gccacagttc gtttgatttc cacattggtg cc 42

<210> SEQ ID NO 33
<211> LENGTH: 42
<212> TYPE: DNA
<213> ORGANISM: Artificial sequence
<220> FEATURE:
<223> OTHER INFORMATION: Primer

<400> SEQUENCE: 33
agatggtgca gccacagttc gtaggatctc cagctcggtc cc 42

<210> SEQ ID NO 34
<211> LENGTH: 42
<212> TYPE: DNA
<213> ORGANISM: Artificial sequence
<220> FEATURE:
<223> OTHER INFORMATION: Primer

<400> SEQUENCE: 34
agatggtgca gccacagttc gtttgacsac cacctcggtc cc 42

<210> SEQ ID NO 35
<211> LENGTH: 40
<212> TYPE: DNA
<213> ORGANISM: Artificial sequence
<220> FEATURE:
<223> OTHER INFORMATION: Primer

<400> SEQUENCE: 35
gggcccaggc ggccgagctc gtgctgactc agtcgccctc 40

<210> SEQ ID NO 36
<211> LENGTH: 45
<212> TYPE: DNA
<213> ORGANISM: Artificial sequence
<220> FEATURE:
<223> OTHER INFORMATION: Primer

<400> SEQUENCE: 36
agatggtgca gccacagttc ggcctgtgac ggtcagctgg gtccc 45

<210> SEQ ID NO 37
<211> LENGTH: 42
<212> TYPE: DNA
<213> ORGANISM: Artificial sequence
<220> FEATURE:
<223> OTHER INFORMATION: Primer

<400> SEQUENCE: 37
gctgcccaac cagccatggc ccagtcggtg gaggagtccr gg 42

<210> SEQ ID NO 38
<211> LENGTH: 42
<212> TYPE: DNA
<213> ORGANISM: Artificial sequence
<220> FEATURE:
<223> OTHER INFORMATION: Primer

<400> SEQUENCE: 38
gctgcccaac aagccatggc ccagtcggtg aaggagtccg ag 42

<210> SEQ ID NO 39
<211> LENGTH: 42
<212> TYPE: DNA
<213> ORGANISM: Artificial sequence
<220> FEATURE:
<223> OTHER INFORMATION: Primer

<400> SEQUENCE: 39
gctgcccaac cagccatggc ccagtcgytg gaggagtccg gg                42

<210> SEQ ID NO 40
<211> LENGTH: 44
<212> TYPE: DNA
<213> ORGANISM: Artificial sequence
<220> FEATURE:
<223> OTHER INFORMATION: Primer

<400> SEQUENCE: 40
gctgcccaac cagccatggc ccagsagcag ctgrtggagt ccgg             44

<210> SEQ ID NO 41
<211> LENGTH: 45
<212> TYPE: DNA
<213> ORGANISM: Artificial sequence
<220> FEATURE:
<223> OTHER INFORMATION: Primer

<400> SEQUENCE: 41
cgatgggccc ttggtggagg ctgargagay ggtgaccagg gtgcc            45

<210> SEQ ID NO 42
<211> LENGTH: 24
<212> TYPE: DNA
<213> ORGANISM: Artificial seqeunce
<220> FEATURE:
<223> OTHER INFORMATION: Primer

<400> SEQUENCE: 42
cgaactgtgg ctgcaccatc tgtc                                   24

<210> SEQ ID NO 43
<211> LENGTH: 21
<212> TYPE: DNA
<213> ORGANISM: Artificial sequence
<220> FEATURE:
<223> OTHER INFORMATION: Primer

<400> SEQUENCE: 43
ggccatggct ggttgggcag c                                      21

<210> SEQ ID NO 44
<211> LENGTH: 21
<212> TYPE: DNA
<213> ORGANISM: Artificial sequence
<220> FEATURE:
<223> OTHER INFORMATION: Primer

<400> SEQUENCE: 44
agaagcgtag tccggaacgt c                                      21

<210> SEQ ID NO 45
<211> LENGTH: 21
<212> TYPE: DNA
<213> ORGANISM: Artificial sequence
<220> FEATURE:
<223> OTHER INFORMATION: Primer

<400> SEQUENCE: 45
agaagcgtag tccggaacgt c                                      21

<210> SEQ ID NO 46
<211> LENGTH: 41
<212> TYPE: DNA
<213> ORGANISM: Artificial sequence
<220> FEATURE:
<223> OTHER INFORMATION: Primer

<400> SEQUENCE: 46
gaggaggagg aggaggaggc ggggcccagg cggccgagct c         41

<210> SEQ ID NO 47
<211> LENGTH: 21
<212> TYPE: DNA
<213> ORGANISM: Artificial sequence
<220> FEATURE:
<223> OTHER INFORMATION: Primer

<400> SEQUENCE: 47
ggccatggct ggttgggcag c                              21

<210> SEQ ID NO 48
<211> LENGTH: 21
<212> TYPE: DNA
<213> ORGANISM: Artificial sequence
<220> FEATURE:
<223> OTHER INFORMATION: Primer

<400> SEQUENCE: 48
gctgcccaac cagccatggc c                              21

<210> SEQ ID NO 49
<211> LENGTH: 21
<212> TYPE: DNA
<213> ORGANISM: Artificial sequence
<220> FEATURE:
<223> OTHER INFORMATION: Primer

<400> SEQUENCE: 49
agaagcgtag tccggaacgt c                              21

<210> SEQ ID NO 50
<211> LENGTH: 41
<212> TYPE: DNA
<213> ORGANISM: Artificial sequence
<220> FEATURE:
<223> OTHER INFORMATION: Primer

<400> SEQUENCE: 50
gaggaggagg aggaggaggc ggggcccagg cggccgagct c         41

<210> SEQ ID NO 51
<211> LENGTH: 39
<212> TYPE: DNA
<213> ORGANISM: Artificial sequence
<220> FEATURE:
<223> OTHER INFORMATION: Primer

<400> SEQUENCE: 51
gaggaggagg aggaggagag aagcgtagtc cggaacgtc            39

<210> SEQ ID NO 52
<211> LENGTH: 30
<212> TYPE: DNA
<213> ORGANISM: Artificial sequence
<220> FEATURE:
<223> OTHER INFORMATION: Primer

<400> SEQUENCE: 52
cgcgaattcg cctccaccaa gggcccatcg                                    30

<210> SEQ ID NO 53
<211> LENGTH: 24
<212> TYPE: DNA
<213> ORGANISM: Artificial sequence
<220> FEATURE:
<223> OTHER INFORMATION: Primer

<400> SEQUENCE: 53
ggcggccgct catttacccg ggga                                          24

<210> SEQ ID NO 54
<211> LENGTH: 29
<212> TYPE: DNA
<213> ORGANISM: Artificial sequence
<220> FEATURE:
<223> OTHER INFORMATION: Primer

<400> SEQUENCE: 54
cgcgaattca ggacctcacc atgggatgg                                     29

<210> SEQ ID NO 55
<211> LENGTH: 19
<212> TYPE: DNA
<213> ORGANISM: Artificial sequence
<220> FEATURE:
<223> OTHER INFORMATION: Primer

<400> SEQUENCE: 55
ggagtggaca cctgtagct                                                19

<210> SEQ ID NO 56
<211> LENGTH: 24
<212> TYPE: DNA
<213> ORGANISM: Artificial sequence
<220> FEATURE:
<223> OTHER INFORMATION: Primer

<400> SEQUENCE: 56
ccacgctgct gagggagtag agtc                                          24

<210> SEQ ID NO 57
<211> LENGTH: 42
<212> TYPE: DNA
<213> ORGANISM: Artificial sequence
<220> FEATURE:
<223> OTHER INFORMATION: Primer

<400> SEQUENCE: 57
gcaacagcta caggtgtcca ctcccagcag cagctgatgg ag                      42

<210> SEQ ID NO 58
<211> LENGTH: 43
<212> TYPE: DNA
<213> ORGANISM: Artificial sequence
<220> FEATURE:
<223> OTHER INFORMATION: Primer

<400> SEQUENCE: 58
gcaacagcta caggtgtcca ctcccaggag cagctgatgg agt                     43

<210> SEQ ID NO 59

```
<211> LENGTH: 43
<212> TYPE: DNA
<213> ORGANISM: Artificial sequence
<220> FEATURE:
<223> OTHER INFORMATION: Primer

<400> SEQUENCE: 59
gcaacagcta caggtgtcca ctcccaggag cagctggtgg agt            43

<210> SEQ ID NO 60
<211> LENGTH: 43
<212> TYPE: DNA
<213> ORGANISM: Artificial sequence
<220> FEATURE:
<223> OTHER INFORMATION: Primer

<400> SEQUENCE: 60
gcaacagcta caggtgtcca ctcccagtcg gtgaaggagt ccg            43

<210> SEQ ID NO 61
<211> LENGTH: 43
<212> TYPE: DNA
<213> ORGANISM: Artificial sequence
<220> FEATURE:
<223> OTHER INFORMATION: Primer

<400> SEQUENCE: 61
gcaacagcta caggtgtcca ctcccagtcg ttggaggagt ccg            43

<210> SEQ ID NO 62
<211> LENGTH: 42
<212> TYPE: DNA
<213> ORGANISM: Artificial sequence
<220> FEATURE:
<223> OTHER INFORMATION: Primer

<400> SEQUENCE: 62
gcaacagcta caggtgtcca ctcccagtcg gtggaggagt cc             42

<210> SEQ ID NO 63
<211> LENGTH: 42
<212> TYPE: DNA
<213> ORGANISM: Artificial sequence
<220> FEATURE:
<223> OTHER INFORMATION: Primer

<400> SEQUENCE: 63
gcaacagcta caggtgtcca ctcccagcgg ttggaggagt cc             42

<210> SEQ ID NO 64
<211> LENGTH: 42
<212> TYPE: DNA
<213> ORGANISM: Artificial sequence
<220> FEATURE:
<223> OTHER INFORMATION: Primer

<400> SEQUENCE: 64
gcaacagcta caggtgtcca ctcccagcag cagctggtgg ag             42

<210> SEQ ID NO 65
<211> LENGTH: 42
<212> TYPE: DNA
<213> ORGANISM: Artificial sequence
<220> FEATURE:
<223> OTHER INFORMATION: Primer

<400> SEQUENCE: 65
```

-continued gcaacagcta caggtgtcca ctcccagtcg ctggaggagt cc          42

<210> SEQ ID NO 66
<211> LENGTH: 30
<212> TYPE: DNA
<213> ORGANISM: Artificial sequence
<220> FEATURE:
<223> OTHER INFORMATION: Primer

<400> SEQUENCE: 66
gcgaagcttc gaactgtggc tgcaccatct          30

<210> SEQ ID NO 67
<211> LENGTH: 29
<212> TYPE: DNA
<213> ORGANISM: Artificial sequence
<220> FEATURE:
<223> OTHER INFORMATION: Primer

<400> SEQUENCE: 67
gcgtctagat taacactctc ccctgttga          29

<210> SEQ ID NO 68
<211> LENGTH: 5
<212> TYPE: PRT
<213> ORGANISM: Homo sapiens

<400> SEQUENCE: 68

Asn Ser Gly Met Ser
1               5

<210> SEQ ID NO 69
<211> LENGTH: 16
<212> TYPE: PRT
<213> ORGANISM: Homo sapiens

<400> SEQUENCE: 69

Leu Ile Asn Ser Tyr Gly Thr Thr Tyr Tyr Ala Ser Trp Ala Lys Gly
1               5                   10                  15

<210> SEQ ID NO 70
<211> LENGTH: 8
<212> TYPE: PRT
<213> ORGANISM: Homo sapiens

<400> SEQUENCE: 70

Gly Ala Gly Ser Ser Tyr Gly Leu
1               5

<210> SEQ ID NO 71
<211> LENGTH: 5
<212> TYPE: PRT
<213> ORGANISM: Homo sapiens

<400> SEQUENCE: 71

Ser Tyr Glu Met Asn
1               5

<210> SEQ ID NO 72
<211> LENGTH: 16
<212> TYPE: PRT
<213> ORGANISM: Homo sapiens

<400> SEQUENCE: 72

```
Ile Ile Arg Ser Asp Gly Ser Thr Tyr Tyr Ala Ser Trp Ala Lys Ser
1               5                   10                  15
```

<210> SEQ ID NO 73
<211> LENGTH: 8
<212> TYPE: PRT
<213> ORGANISM: Homo sapiens

<400> SEQUENCE: 73

```
Asp Leu Gly Tyr Ser Asn Asp Val
1               5
```

<210> SEQ ID NO 74
<211> LENGTH: 5
<212> TYPE: PRT
<213> ORGANISM: Homo sapiens

<400> SEQUENCE: 74

```
Ser Tyr Met Ile Tyr
1               5
```

<210> SEQ ID NO 75
<211> LENGTH: 16
<212> TYPE: PRT
<213> ORGANISM: Homo sapiens

<400> SEQUENCE: 75

```
Phe Ile Tyr Gly Ser Gly Asp Thr Tyr Tyr Ala Thr Trp Ala Lys Gly
1               5                   10                  15
```

<210> SEQ ID NO 76
<211> LENGTH: 10
<212> TYPE: PRT
<213> ORGANISM: Homo sapiens

<400> SEQUENCE: 76

```
Ser Ser Gly Trp Gly Tyr Gly Leu Asp Leu
1               5                   10
```

<210> SEQ ID NO 77
<211> LENGTH: 5
<212> TYPE: PRT
<213> ORGANISM: Homo sapiens

<400> SEQUENCE: 77

```
Ser Tyr His Met Gln
1               5
```

<210> SEQ ID NO 78
<211> LENGTH: 16
<212> TYPE: PRT
<213> ORGANISM: Homo sapiens

<400> SEQUENCE: 78

```
Phe Ile Asp Thr Val Gly Ser Ala Tyr Tyr Ala Ser Trp Ala Lys Gly
1               5                   10                  15
```

<210> SEQ ID NO 79
<211> LENGTH: 9
<212> TYPE: PRT
<213> ORGANISM: Homo sapiens

<400> SEQUENCE: 79

```
Asp Ser Gly Tyr Ser Ile Gly Thr Leu
1               5
```

```
<210> SEQ ID NO 80
<211> LENGTH: 5
<212> TYPE: PRT
<213> ORGANISM: Homo sapiens

<400> SEQUENCE: 80

Ser Tyr Ala Met Ile
1               5

<210> SEQ ID NO 81
<211> LENGTH: 16
<212> TYPE: PRT
<213> ORGANISM: Homo sapiens

<400> SEQUENCE: 81

Ile Ile Arg Ser Ser Gly Asn Thr Tyr Tyr Ala Ser Trp Ala Lys Gly
1               5                   10                  15

<210> SEQ ID NO 82
<211> LENGTH: 8
<212> TYPE: PRT
<213> ORGANISM: Homo sapiens

<400> SEQUENCE: 82

Asp Ser Gly Tyr Ser Phe Gly Leu
1               5

<210> SEQ ID NO 83
<211> LENGTH: 5
<212> TYPE: PRT
<213> ORGANISM: Homo sapiens

<400> SEQUENCE: 83

Ser His Glu Met Asn
1               5

<210> SEQ ID NO 84
<211> LENGTH: 16
<212> TYPE: PRT
<213> ORGANISM: Homo sapiens

<400> SEQUENCE: 84

Ile Ile Asn Ser Tyr Ala Asn Thr Tyr Tyr Ala Gly Trp Ala Lys Ser
1               5                   10                  15

<210> SEQ ID NO 85
<211> LENGTH: 8
<212> TYPE: PRT
<213> ORGANISM: Homo sapiens

<400> SEQUENCE: 85

Asp Leu Gly Tyr Ser Ser Asp Ile
1               5

<210> SEQ ID NO 86
<211> LENGTH: 5
<212> TYPE: PRT
<213> ORGANISM: Homo sapiens

<400> SEQUENCE: 86

Ser Tyr Glu Met Ser
1               5
```

```
<210> SEQ ID NO 87
<211> LENGTH: 16
<212> TYPE: PRT
<213> ORGANISM: Homo sapiens

<400> SEQUENCE: 87

Phe Ile Ser Thr Ser Gly Asn Thr Tyr Tyr Ala Ser Trp Ala Lys Gly
1               5                   10                  15

<210> SEQ ID NO 88
<211> LENGTH: 13
<212> TYPE: PRT
<213> ORGANISM: Homo sapiens

<400> SEQUENCE: 88

Gly Pro Ala Lys Ser Gly Tyr Gly Thr Arg Leu Asp Leu
1               5                   10

<210> SEQ ID NO 89
<211> LENGTH: 5
<212> TYPE: PRT
<213> ORGANISM: Homo sapiens

<400> SEQUENCE: 89

Ser Tyr Arg Met Gly
1               5

<210> SEQ ID NO 90
<211> LENGTH: 16
<212> TYPE: PRT
<213> ORGANISM: Homo sapiens

<400> SEQUENCE: 90

Phe Ile Asn Asn Tyr Gly Ser Ala Tyr Tyr Ala Ser Trp Ala Lys Ser
1               5                   10                  15

<210> SEQ ID NO 91
<211> LENGTH: 11
<212> TYPE: PRT
<213> ORGANISM: Homo sapiens

<400> SEQUENCE: 91

Glu Ser Tyr Ser Tyr Gly Tyr Ala Tyr Asp Ile
1               5                   10

<210> SEQ ID NO 92
<211> LENGTH: 5
<212> TYPE: PRT
<213> ORGANISM: Homo sapiens

<400> SEQUENCE: 92

Gly Tyr Ala Met Gly
1               5

<210> SEQ ID NO 93
<211> LENGTH: 16
<212> TYPE: PRT
<213> ORGANISM: Homo sapiens

<400> SEQUENCE: 93

Ile Ile Gly Thr Ser Asp Thr Thr Tyr Tyr Ala Ser Trp Ala Lys Gly
1               5                   10                  15

<210> SEQ ID NO 94
<211> LENGTH: 8
```

```
<212> TYPE: PRT
<213> ORGANISM: Homo sapiens

<400> SEQUENCE: 94

Ser Pro Gly Gly Ser Ala Asp Leu
1               5

<210> SEQ ID NO 95
<211> LENGTH: 5
<212> TYPE: PRT
<213> ORGANISM: Homo sapiens

<400> SEQUENCE: 95

Ser Tyr Glu Met Asn
1               5

<210> SEQ ID NO 96
<211> LENGTH: 16
<212> TYPE: PRT
<213> ORGANISM: Homo sapiens

<400> SEQUENCE: 96

Ile Ile Arg Ser Asp Gly Ser Thr Tyr Tyr Ala Ser Trp Ala Lys Ser
1               5                   10                  15

<210> SEQ ID NO 97
<211> LENGTH: 8
<212> TYPE: PRT
<213> ORGANISM: Homo sapiens

<400> SEQUENCE: 97

Asp Leu Gly Tyr Ser Asn Asp Val
1               5

<210> SEQ ID NO 98
<211> LENGTH: 5
<212> TYPE: PRT
<213> ORGANISM: Homo sapiens

<400> SEQUENCE: 98

Thr Tyr Glu Met Asn
1               5

<210> SEQ ID NO 99
<211> LENGTH: 16
<212> TYPE: PRT
<213> ORGANISM: Homo sapiens

<400> SEQUENCE: 99

Ile Ile Asn Ser Ala Gly Thr Thr Tyr Tyr Ala Ser Trp Ala Lys Ser
1               5                   10                  15

<210> SEQ ID NO 100
<211> LENGTH: 8
<212> TYPE: PRT
<213> ORGANISM: Homo sapiens

<400> SEQUENCE: 100

Asp Leu Gly Tyr Ser Ser Asp Ile
1               5

<210> SEQ ID NO 101
<211> LENGTH: 11
<212> TYPE: PRT
<213> ORGANISM: Homo sapiens
```

```
<400> SEQUENCE: 101

Gln Ala Ser Gln Ser Ile Gly Ser Asn Leu Ala
1               5                   10

<210> SEQ ID NO 102
<211> LENGTH: 6
<212> TYPE: PRT
<213> ORGANISM: Homo sapiens

<400> SEQUENCE: 102

Ala Ser Asn Leu Ala Ser
1               5

<210> SEQ ID NO 103
<211> LENGTH: 10
<212> TYPE: PRT
<213> ORGANISM: Homo sapiens

<400> SEQUENCE: 103

Leu Gly Ser Asp Ser Ser Trp Asp Thr Val
1               5                   10

<210> SEQ ID NO 104
<211> LENGTH: 11
<212> TYPE: PRT
<213> ORGANISM: Homo sapiens

<400> SEQUENCE: 104

Gln Ala Ser Gln Asn Ile Gly Ile Asn Leu Ala
1               5                   10

<210> SEQ ID NO 105
<211> LENGTH: 7
<212> TYPE: PRT
<213> ORGANISM: Homo sapiens

<400> SEQUENCE: 105

Tyr Ala Ser Asp Leu Ala Ser
1               5

<210> SEQ ID NO 106
<211> LENGTH: 10
<212> TYPE: PRT
<213> ORGANISM: Homo sapiens

<400> SEQUENCE: 106

Leu Gly Thr Tyr Gly Ser Gly Asp Arg Ala
1               5                   10

<210> SEQ ID NO 107
<211> LENGTH: 11
<212> TYPE: PRT
<213> ORGANISM: Homo sapiens

<400> SEQUENCE: 107

Gln Ala Ser Gln Ser Ile Asn Val Trp Leu Ser
1               5                   10

<210> SEQ ID NO 108
<211> LENGTH: 7
<212> TYPE: PRT
<213> ORGANISM: Homo sapiens

<400> SEQUENCE: 108
```

```
Gln Ala Ser Lys Leu Ala Ser
1               5
```

<210> SEQ ID NO 109
<211> LENGTH: 10
<212> TYPE: PRT
<213> ORGANISM: Homo sapiens

<400> SEQUENCE: 109

```
Leu Gly Ile Tyr Asn Asp Ile Asp Thr Ala
1               5                   10
```

<210> SEQ ID NO 110
<211> LENGTH: 11
<212> TYPE: PRT
<213> ORGANISM: Homo sapiens

<400> SEQUENCE: 110

```
Gln Ala Thr Lys Asn Ile Gly Ile Asn Leu Ala
1               5                   10
```

<210> SEQ ID NO 111
<211> LENGTH: 7
<212> TYPE: PRT
<213> ORGANISM: Homo sapiens

<400> SEQUENCE: 111

```
Tyr Ala Ser Asp Leu Ala Ser
1               5
```

<210> SEQ ID NO 112
<211> LENGTH: 10
<212> TYPE: PRT
<213> ORGANISM: Homo sapiens

<400> SEQUENCE: 112

```
Leu Gly Ser Tyr Gly Ser Gly Asp Arg Ala
1               5                   10
```

<210> SEQ ID NO 113
<211> LENGTH: 11
<212> TYPE: PRT
<213> ORGANISM: Homo sapiens

<400> SEQUENCE: 113

```
Gln Ala Ser Lys Asn Ile Gly Ile Asn Leu Ala
1               5                   10
```

<210> SEQ ID NO 114
<211> LENGTH: 11
<212> TYPE: PRT
<213> ORGANISM: Homo sapiens

<400> SEQUENCE: 114

```
Arg Ala Ser Gln Ile Ile Gly Ile Asn Leu Ala
1               5                   10
```

<210> SEQ ID NO 115
<211> LENGTH: 10
<212> TYPE: PRT
<213> ORGANISM: Homo sapiens

<400> SEQUENCE: 115

```
Leu Gly Thr Tyr Gly Ser Gly Val Arg Ala
```

```
1               5                    10
```

<210> SEQ ID NO 116
<211> LENGTH: 7
<212> TYPE: PRT
<213> ORGANISM: Homo sapiens

<400> SEQUENCE: 116

Tyr Thr Ser Asp Leu Ala Ser
1               5

<210> SEQ ID NO 117
<211> LENGTH: 29
<212> TYPE: DNA
<213> ORGANISM: Artificial sequence
<220> FEATURE:
<223> OTHER INFORMATION: Primer

<400> SEQUENCE: 117
gcgaagctta ggacctcacc atgggatgg                                    29

<210> SEQ ID NO 118
<211> LENGTH: 44
<212> TYPE: DNA
<213> ORGANISM: Artificial sequence
<220> FEATURE:
<223> OTHER INFORMATION: Primer

<400> SEQUENCE: 118
gcaacagcta caggtgtcca ctccgagctc gatatgaccc agac                   44

<210> SEQ ID NO 119
<211> LENGTH: 42
<212> TYPE: DNA
<213> ORGANISM: Artificial sequence
<220> FEATURE:
<223> OTHER INFORMATION: Primer

<400> SEQUENCE: 119
gcaacagcta caggtgtcca ctccgagctc gtgctgaacc ca                     42

<210> SEQ ID NO 120
<211> LENGTH: 44
<212> TYPE: DNA
<213> ORGANISM: Artificial sequence
<220> FEATURE:
<223> OTHER INFORMATION: Primer

<400> SEQUENCE: 120
gcaacagcta caggtgtcca ctccgagctc gtgatgaccc agac                   44

<210> SEQ ID NO 121
<211> LENGTH: 44
<212> TYPE: DNA
<213> ORGANISM: Artificial sequence
<220> FEATURE:
<223> OTHER INFORMATION: Primer

<400> SEQUENCE: 121
gcaacagcta caggtgtcca ctccgagctc gatctgaccc agac                   44

<210> SEQ ID NO 122
<211> LENGTH: 29
<212> TYPE: DNA
<213> ORGANISM: Artificial sequence
<220> FEATURE:

<223> OTHER INFORMATION: Primer

<400> SEQUENCE: 122
cgccgtacgt aggatctcca gctcggtcc                             29

<210> SEQ ID NO 123
<211> LENGTH: 30
<212> TYPE: DNA
<213> ORGANISM: Artificial sequence
<220> FEATURE:
<223> OTHER INFORMATION: Primer

<400> SEQUENCE: 123
cgccgtacgt ttgatttcca cattggtgcc                            30

<210> SEQ ID NO 124
<211> LENGTH: 28
<212> TYPE: DNA
<213> ORGANISM: Artificial sequence
<220> FEATURE:
<223> OTHER INFORMATION: Primer

<400> SEQUENCE: 124
cgccgtacgt ttgacgacca cctcggtc                              28

<210> SEQ ID NO 125
<211> LENGTH: 30
<212> TYPE: DNA
<213> ORGANISM: Artificial sequence
<220> FEATURE:
<223> OTHER INFORMATION: Primer

<400> SEQUENCE: 125
cgccgtacgt aggatctcca gctcggtccc                            30

<210> SEQ ID NO 126
<211> LENGTH: 21
<212> TYPE: DNA
<213> ORGANISM: Homo sapiens

<400> SEQUENCE: 126
aagacgggga taagcgctat a                                     21

<210> SEQ ID NO 127
<211> LENGTH: 21
<212> TYPE: DNA
<213> ORGANISM: Homo sapiens

<400> SEQUENCE: 127
aagcgctata agcttctgct g                                     21

<210> SEQ ID NO 128
<211> LENGTH: 21
<212> TYPE: DNA
<213> ORGANISM: Homo sapiens

<400> SEQUENCE: 128
aagcttctgc tggggatagg a                                     21

<210> SEQ ID NO 129
<211> LENGTH: 21
<212> TYPE: DNA
<213> ORGANISM: Homo sapiens

<400> SEQUENCE: 129

-continued aattctggtg ctcctgatca t					21

<210> SEQ ID NO 130
<211> LENGTH: 21
<212> TYPE: DNA
<213> ORGANISM: Homo sapiens

<400> SEQUENCE: 130
aaggccaaca gcgaggcctg c					21

<210> SEQ ID NO 131
<211> LENGTH: 21
<212> TYPE: DNA
<213> ORGANISM: Homo sapiens

<400> SEQUENCE: 131
aacagcgagg cctgccggga c					21

<210> SEQ ID NO 132
<211> LENGTH: 21
<212> TYPE: DNA
<213> ORGANISM: Homo sapiens

<400> SEQUENCE: 132
aatgtcaccc atctcctgca a					21

<210> SEQ ID NO 133
<211> LENGTH: 21
<212> TYPE: DNA
<213> ORGANISM: Homo sapiens

<400> SEQUENCE: 133
aacaagagct gaccgaggcc c					21

<210> SEQ ID NO 134
<211> LENGTH: 21
<212> TYPE: DNA
<213> ORGANISM: Homo sapiens

<400> SEQUENCE: 134
aagagctgac cgaggcccag a					21

<210> SEQ ID NO 135
<211> LENGTH: 21
<212> TYPE: DNA
<213> ORGANISM: Homo sapiens

<400> SEQUENCE: 135
aagggctttc aggatgtgga g					21

<210> SEQ ID NO 136
<211> LENGTH: 21
<212> TYPE: DNA
<213> ORGANISM: Homo sapiens

<400> SEQUENCE: 136
aaccacactg tgatggccct a					21

<210> SEQ ID NO 137
<211> LENGTH: 21
<212> TYPE: DNA
<213> ORGANISM: Homo sapiens

```
<400> SEQUENCE: 137
aatggcttcc ctggatgcag a                                              21

<210> SEQ ID NO 138
<211> LENGTH: 21
<212> TYPE: DNA
<213> ORGANISM: Homo sapiens

<400> SEQUENCE: 138
aaggcccaag gacaaaagaa a                                              21

<210> SEQ ID NO 139
<211> LENGTH: 20
<212> TYPE: DNA
<213> ORGANISM: Homo sapiens

<400> SEQUENCE: 139
aaggacaaaa gaagtggagg                                                20

<210> SEQ ID NO 140
<211> LENGTH: 21
<212> TYPE: DNA
<213> ORGANISM: Homo sapiens

<400> SEQUENCE: 140
aagaaagtgg aggagcttga g                                              21

<210> SEQ ID NO 141
<211> LENGTH: 19
<212> TYPE: DNA
<213> ORGANISM: Homo sapiens

<400> SEQUENCE: 141
ggagagatca ctacattaa                                                 19

<210> SEQ ID NO 142
<211> LENGTH: 21
<212> TYPE: DNA
<213> ORGANISM: Homo sapiens

<400> SEQUENCE: 142
aaaccataag cttcaggacg c                                              21

<210> SEQ ID NO 143
<211> LENGTH: 21
<212> TYPE: DNA
<213> ORGANISM: Homo sapiens

<400> SEQUENCE: 143
aagcttcagg acgcgtctgc a                                              21

<210> SEQ ID NO 144
<211> LENGTH: 21
<212> TYPE: DNA
<213> ORGANISM: Homo sapiens

<400> SEQUENCE: 144
aagagaaaac caggtcttaa g                                              21

<210> SEQ ID NO 145
<211> LENGTH: 20
<212> TYPE: DNA
<213> ORGANISM: Homo sapiens
```

```
<400> SEQUENCE: 145
aaccaggtct taagcgtaga                                                      20

<210> SEQ ID NO 146
<211> LENGTH: 21
<212> TYPE: DNA
<213> ORGANISM: Homo sapiens

<400> SEQUENCE: 146
aagcgtgaga atcgcggaca a                                                    21

<210> SEQ ID NO 147
<211> LENGTH: 21
<212> TYPE: DNA
<213> ORGANISM: Homo sapiens

<400> SEQUENCE: 147
aatcgcggac aagaagtact a                                                    21

<210> SEQ ID NO 148
<211> LENGTH: 21
<212> TYPE: DNA
<213> ORGANISM: Homo sapiens

<400> SEQUENCE: 148
aagaagtact accccagctc c                                                    21

<210> SEQ ID NO 149
<211> LENGTH: 117
<212> TYPE: PRT
<213> ORGANISM: Homo sapiens

<400> SEQUENCE: 149
```

Met Ala Gln Ser Val Lys Glu Ser Glu Gly Arg Leu Val Thr Pro Gly
1               5                   10                  15

Thr Pro Leu Thr Leu Thr Cys Thr Val Ser Gly Phe Ser Leu Ser Asn
            20                  25                  30

Ser Gly Met Ser Trp Val Arg Gln Ala Pro Gly Lys Gly Leu Glu Trp
        35                  40                  45

Ile Gly Leu Ile Asn Ser Tyr Gly Thr Thr Tyr Ala Ser Trp Ala
    50                  55                  60

Lys Gly Arg Phe Thr Ile Ser Lys Thr Ser Thr Val Glu Leu Lys
65                  70                  75                  80

Ile Thr Ser Pro Thr Thr Glu Asp Thr Ala Thr Tyr Phe Cys Ala Arg
                85                  90                  95

Gly Ala Gly Ser Ser Tyr Gly Leu Trp Gly Gln Gly Thr Leu Val Thr
            100                 105                 110

Val Ser Ser Ala Ser
        115

```
<210> SEQ ID NO 150
<211> LENGTH: 120
<212> TYPE: PRT
<213> ORGANISM: Homo sapiens

<400> SEQUENCE: 150
```

Met Ala Gln Ser Val Lys Glu Ser Glu Gly Gly Leu Phe Lys Pro Thr
1               5                   10                  15

Asp Thr Leu Thr Leu Thr Cys Thr Val Ser Gly Phe Ser Leu Ser Ser

-continued

```
                        20                  25                  30
Tyr Glu Met Asn Trp Val Arg Gln Ala Pro Gly Lys Gly Leu Glu Tyr
                35                  40                  45
Ile Gly Ile Ile Arg Ser Asp Gly Ser Thr Tyr Tyr Ala Ser Trp Ala
        50                  55                  60
Lys Ser Arg Ser Thr Ile Thr Arg Asn Thr Asn Leu Asn Val Thr
65                  70                  75                  80
Leu Lys Met Thr Ser Leu Thr Ala Ala Asp Thr Ala Thr Tyr Phe Cys
                85                  90                  95
Ala Arg Asp Leu Gly Tyr Ser Asn Asp Val Trp Gly Pro Gly Thr Leu
            100                 105                 110
Val Thr Val Ser Ser Ala Ser Thr
            115                 120

<210> SEQ ID NO 151
<211> LENGTH: 120
<212> TYPE: PRT
<213> ORGANISM: Homo sapiens

<400> SEQUENCE: 151

Met Ala Gln Ser Leu Glu Glu Ser Gly Gly Arg Leu Val Lys Pro Asp
1               5                   10                  15
Glu Thr Leu Thr Leu Thr Cys Thr Val Ser Gly Ile Asp Leu Ser Ser
                20                  25                  30
Tyr Met Ile Tyr Trp Val Arg Gln Ala Pro Gly Lys Gly Leu Glu Tyr
                35                  40                  45
Ile Gly Phe Ile Tyr Gly Ser Gly Asp Thr Tyr Tyr Ala Thr Trp Ala
        50                  55                  60
Lys Gly Arg Phe Thr Ile Ser Arg Pro Ser Thr Val Asp Leu Lys
65                  70                  75                  80
Ile Thr Ser Pro Thr Thr Gly Asp Thr Ala Thr Tyr Phe Cys Ala Arg
                85                  90                  95
Ser Ser Gly Trp Gly Tyr Gly Leu Asp Leu Trp Gly Pro Gly Thr Leu
            100                 105                 110
Val Thr Ile Ser Ser Ala Ser Thr
            115                 120

<210> SEQ ID NO 152
<211> LENGTH: 119
<212> TYPE: PRT
<213> ORGANISM: Homo sapiens

<400> SEQUENCE: 152

Met Ala Gln Gln Leu Val Glu Ser Gly Gly Arg Leu Val Thr Pro Gly
1               5                   10                  15
Gly Thr Leu Thr Leu Thr Cys Thr Ala Ser Gly Ile Asp Leu Ser Ser
                20                  25                  30
Tyr His Met Gln Trp Val Arg Gln Ala Pro Gly Lys Gly Leu Glu Tyr
                35                  40                  45
Ile Gly Phe Ile Asp Thr Val Gly Ser Ala Tyr Tyr Ala Ser Trp Ala
        50                  55                  60
Lys Gly Arg Phe Thr Ile Ser Arg Thr Ser Thr Thr Val Asp Leu Lys
65                  70                  75                  80
Met Thr Ser Leu Thr Ala Ala Asp Thr Ala Thr Tyr Phe Cys Ala Gly
                85                  90                  95
Asp Ser Gly Tyr Ser Ile Gly Thr Leu Trp Gly Gln Gly Thr Leu Val
```

-continued

```
                  100                 105                 110
Thr Val Ser Ser Ala Ser Thr
        115

<210> SEQ ID NO 153
<211> LENGTH: 119
<212> TYPE: PRT
<213> ORGANISM: Homo sapiens

<400> SEQUENCE: 153

Met Ala Gln Gln Gln Leu Val Glu Ser Gly Gly Gly Leu Val Thr Pro
1               5                   10                  15

Gly Thr Pro Leu Thr Leu Thr Cys Thr Val Ser Gly Phe Ser Leu Ser
                20                  25                  30

Ser Tyr Ala Met Ile Trp Val Arg Gln Ala Pro Gly Lys Gly Leu Glu
            35                  40                  45

Tyr Ile Gly Ile Ile Arg Ser Ser Gly Asn Thr Tyr Tyr Ala Ser Trp
        50                  55                  60

Ala Lys Gly Arg Phe Thr Ile Ser Lys Thr Ser Thr Thr Val Asp Leu
65                  70                  75                  80

Lys Ile Thr Ser Pro Thr Thr Glu Asp Thr Ala Thr Tyr Phe Cys Ala
                85                  90                  95

Arg Asp Ser Gly Tyr Ser Phe Gly Leu Trp Gly Gln Gly Thr Leu Val
                100                 105                 110

Thr Val Ser Ser Ala Ser Thr
        115

<210> SEQ ID NO 154
<211> LENGTH: 120
<212> TYPE: PRT
<213> ORGANISM: Homo sapiens

<400> SEQUENCE: 154

Met Ala Gln Ser Val Lys Glu Ser Glu Gly Gly Leu Phe Lys Pro Thr
1               5                   10                  15

Asp Thr Leu Thr Leu Thr Cys Thr Val Ser Gly Phe Ser Leu Ser Ser
                20                  25                  30

His Glu Met Asn Trp Val Arg Gln Ala Pro Gly Asn Gly Leu Glu Tyr
            35                  40                  45

Ile Gly Ile Ile Asn Ser Tyr Ala Asn Thr Tyr Tyr Ala Gly Trp Ala
        50                  55                  60

Lys Ser Arg Ser Thr Ile Thr Arg Asn Thr Asn Glu Asn Thr Val Thr
65                  70                  75                  80

Leu Thr Met Thr Ser Leu Thr Ala Ala Asp Thr Ala Thr Tyr Phe Cys
                85                  90                  95

Val Arg Asp Leu Gly Tyr Ser Asp Ile Trp Gly Pro Gly Thr Leu
                100                 105                 110

Val Thr Ile Ser Ser Ala Ser Thr
        115                 120

<210> SEQ ID NO 155
<211> LENGTH: 123
<212> TYPE: PRT
<213> ORGANISM: Homo sapiens

<400> SEQUENCE: 155

Met Ala Gln Ser Leu Glu Glu Ser Gly Gly Arg Leu Val Thr Pro Gly
1               5                   10                  15
```

Thr Pro Leu Thr Leu Thr Cys Thr Val Ser Gly Ile Asp Leu Ser Ser
            20                  25                  30

Tyr Glu Met Ser Trp Val Arg Gln Ala Pro Gly Lys Gly Leu Glu Tyr
        35                  40                  45

Ile Gly Phe Ile Ser Thr Ser Gly Asn Thr Tyr Tyr Ala Ser Trp Ala
    50                  55                  60

Lys Gly Arg Phe Thr Ile Ser Lys Thr Ser Thr Thr Val Asp Leu Lys
65                  70                  75                  80

Ile Thr Ser Pro Thr Ile Glu Asp Thr Ala Ala Tyr Phe Cys Ala Arg
                85                  90                  95

Gly Pro Ala Lys Ser Gly Tyr Gly Thr Arg Leu Asp Leu Trp Gly Gln
            100                 105                 110

Gly Thr Leu Val Thr Val Ser Ser Ala Ser Thr
            115                 120

<210> SEQ ID NO 156
<211> LENGTH: 124
<212> TYPE: PRT
<213> ORGANISM: Homo sapiens

<400> SEQUENCE: 156

Met Ala Gln Glu Gln Leu Met Glu Ser Gly Gly Gly Leu Val Thr Pro
1               5                   10                  15

Gly Gly Ile Leu Ser Leu Thr Cys Thr Ala Ser Gly Phe Ser Ile Ser
            20                  25                  30

Ser Tyr Arg Met Gly Trp Val Arg Gln Ala Pro Gly Lys Gly Leu Glu
        35                  40                  45

Trp Ile Gly Phe Ile Asn Asn Tyr Gly Ser Ala Tyr Tyr Ala Ser Trp
    50                  55                  60

Ala Lys Ser Arg Ser Thr Ile Thr Arg Asn Thr Asn Leu Asn Thr Val
65                  70                  75                  80

Thr Leu Lys Met Thr Ser Leu Thr Ala Ala Asp Thr Ala Thr Tyr Phe
                85                  90                  95

Cys Ala Arg Glu Ser Tyr Ser Tyr Gly Tyr Ala Tyr Asp Ile Trp Gly
            100                 105                 110

Pro Gly Thr Leu Val Thr Val Ser Ser Ala Ser Thr
            115                 120

<210> SEQ ID NO 157
<211> LENGTH: 118
<212> TYPE: PRT
<213> ORGANISM: Homo sapiens

<400> SEQUENCE: 157

Met Ala Gln Glu Gln Leu Val Glu Ser Gly Gly Arg Leu Val Thr Pro
1               5                   10                  15

Gly Gly Ser Leu Thr Ile Thr Cys Thr Val Ser Gly Ile Asp Leu Ser
            20                  25                  30

Gly Tyr Ala Met Gly Trp Val Arg Gln Ala Pro Gly Lys Gly Leu Glu
        35                  40                  45

Tyr Ile Gly Ile Ile Gly Thr Ser Asp Thr Tyr Tyr Ala Ser Trp
    50                  55                  60

Ala Lys Gly Arg Phe Thr Ile Ser Lys Thr Ser Ser Thr Thr Val Asp
65                  70                  75                  80

Leu Lys Met Thr Ser Leu Thr Thr Glu Asp Thr Ala Thr Tyr Phe Cys
                85                  90                  95

Val Arg Ser Pro Gly Gly Ser Ala Trp Gly Gln Gly Thr Leu Val Thr
            100                 105                 110

Ile Ser Ser Ala Ser Thr
            115

<210> SEQ ID NO 158
<211> LENGTH: 120
<212> TYPE: PRT
<213> ORGANISM: Homo sapiens

<400> SEQUENCE: 158

Met Ala Gln Ser Val Lys Glu Ser Glu Gly Leu Phe Lys Pro Thr
1               5                   10                  15

Asp Thr Leu Thr Leu Thr Cys Thr Val Ser Gly Phe Ser Leu Ser Ser
            20                  25                  30

Tyr Glu Met Asn Trp Val Arg Gln Ala Pro Gly Lys Gly Leu Glu Tyr
        35                  40                  45

Ile Gly Ile Ile Arg Ser Asp Gly Ser Thr Tyr Tyr Ala Ser Trp Ala
    50                  55                  60

Lys Ser Arg Ser Thr Ile Thr Arg Asn Thr Asn Leu Asn Thr Val Thr
65                  70                  75                  80

Leu Lys Met Thr Ser Leu Thr Ala Ala Asp Thr Ala Thr Tyr Phe Cys
                85                  90                  95

Ala Arg Asp Leu Gly Tyr Ser Asn Asp Val Trp Gly Pro Gly Thr Leu
            100                 105                 110

Val Thr Ile Ser Ser Ala Ser Thr
            115                 120

<210> SEQ ID NO 159
<211> LENGTH: 120
<212> TYPE: PRT
<213> ORGANISM: Homo sapiens

<400> SEQUENCE: 159

Met Ala Gln Ser Val Glu Glu Ser Arg Gly Gly Leu Phe Lys Pro Thr
1               5                   10                  15

Asp Thr Leu Thr Leu Thr Cys Thr Val Ser Gly Phe Ser Leu Ser Thr
            20                  25                  30

Tyr Glu Met Asn Trp Val Arg Gln Ala Pro Gly Ser Gly Leu Glu Tyr
        35                  40                  45

Ile Gly Ile Ile Asn Ser Ala Gly Thr Thr Tyr Tyr Ala Ser Trp Ala
    50                  55                  60

Lys Ser Arg Ser Thr Ile Thr Arg Asn Thr Asn Glu Asn Thr Val Thr
65                  70                  75                  80

Leu Lys Met Thr Ser Leu Thr Ala Ala Asp Thr Ala Thr Tyr Phe Cys
                85                  90                  95

Ala Arg Asp Leu Gly Tyr Ser Ser Asp Ile Trp Gly Pro Gly Thr Leu
            100                 105                 110

Val Thr Val Ser Ser Ala Ser Thr
            115                 120

<210> SEQ ID NO 160
<211> LENGTH: 114
<212> TYPE: PRT
<213> ORGANISM: Homo sapiens

<400> SEQUENCE: 160

Gln Ala Ala Glu Leu Val Met Thr Gln Thr Pro Ser Ser Thr Ser Thr
1               5                   10                  15

Ala Val Gly Asp Thr Val Thr Ile Lys Cys Gln Ala Ser Gln Ser Ile
            20                  25                  30

Gly Ser Asn Leu Ala Trp Tyr Gln Gln Lys Pro Gly Gln Pro Pro Lys
        35                  40                  45

Ile Leu Ile Tyr Ser Ala Ser Asn Leu Ala Ser Gly Val Pro Ser Arg
    50                  55                  60

Phe Lys Gly Ser Gly Ser Gly Thr Glu Tyr Thr Leu Thr Ile Ser Gly
65              70                  75                  80

Val Gln Arg Glu Asp Ala Ala Thr Tyr Tyr Cys Leu Gly Ser Asp Ser
                85                  90                  95

Ser Trp Asp Thr Val Phe Gly Gly Gly Thr Glu Leu Glu Ile Leu Arg
                100                 105                 110

Thr Val

<210> SEQ ID NO 161
<211> LENGTH: 114
<212> TYPE: PRT
<213> ORGANISM: Homo sapiens

<400> SEQUENCE: 161

Gln Ala Ala Glu Leu Asp Leu Thr Gln Thr Pro Ser Ser Thr Ser Thr
1               5                   10                  15

Ala Val Gly Gly Thr Val Thr Ile Asn Cys Gln Ala Ser Gln Asn Ile
            20                  25                  30

Gly Ile Asn Leu Ala Trp Tyr Gln Gln Lys Pro Gly Gln Pro Pro Lys
        35                  40                  45

Leu Leu Ile Trp Tyr Ala Ser Asp Leu Ala Ser Gly Val Ser Ser Arg
    50                  55                  60

Phe Lys Gly Phe Gly Ser Gly Thr Gln Phe Thr Leu Thr Ile Ser Gly
65              70                  75                  80

Val Gln Arg Glu Asp Ala Ala Thr Tyr Tyr Cys Leu Gly Thr Tyr Gly
                85                  90                  95

Ser Gly Asp Arg Ala Phe Gly Ala Gly Thr Asn Val Glu Ile Lys Arg
                100                 105                 110

Thr Val

<210> SEQ ID NO 162
<211> LENGTH: 111
<212> TYPE: PRT
<213> ORGANISM: Homo sapiens

<400> SEQUENCE: 162

Glu Leu Asp Leu Thr Gln Thr Pro Ser Ser Thr Ser Thr Ala Val Gly
1               5                   10                  15

Gly Thr Val Thr Ile Asn Cys Gln Ala Ser Gln Ser Ile Asn Val Trp
            20                  25                  30

Leu Ser Trp Tyr Gln Gln Lys Pro Gly Gln Pro Pro Lys Leu Leu Ile
        35                  40                  45

Tyr Gln Ala Ser Lys Leu Ala Ser Gly Val Pro Ser Arg Phe Lys Gly
    50                  55                  60

Ser Gly Ser Gly Thr Gln Phe Thr Leu Thr Ile Ser Gly Val Gln Arg
65              70                  75                  80

Glu Asp Val Ala Thr Tyr Tyr Cys Leu Gly Ile Tyr Asn Asp Ile Asp
                85                  90                  95

```
Thr Ala Phe Gly Gly Gly Thr Glu Val Val Lys Arg Thr Val
            100                 105                 110
```

<210> SEQ ID NO 163
<211> LENGTH: 114
<212> TYPE: PRT
<213> ORGANISM: Homo sapiens

<400> SEQUENCE: 163

```
Gln Ala Ala Glu Leu Val Leu Thr Gln Thr Pro Ser Ser Val Ser Ala
1               5                   10                  15

Ala Val Gly Gly Thr Val Thr Ile Asn Cys Gln Ala Thr Gln Ser Ile
            20                  25                  30

Gly Ile Asn Leu Ala Trp Tyr Gln Gln Lys Pro Gly Gln Pro Pro Lys
        35                  40                  45

Leu Leu Ile Trp Tyr Ala Ser Asp Leu Ala Ser Gly Val Pro Ser Arg
    50                  55                  60

Phe Lys Gly Ser Gly Phe Gly Thr Gln Phe Thr Leu Thr Ile Asn Gly
65                  70                  75                  80

Val Gln Arg Glu Asp Ala Ala Thr Tyr Tyr Cys Leu Gly Ser Tyr Gly
                85                  90                  95

Ser Gly Asp Arg Ala Phe Gly Ala Gly Thr Asn Val Glu Ile Lys Arg
            100                 105                 110

Thr Val
```

<210> SEQ ID NO 164
<211> LENGTH: 114
<212> TYPE: PRT
<213> ORGANISM: Homo sapiens

<400> SEQUENCE: 164

```
Gln Ala Ala Glu Leu Val Met Thr Gln Thr Pro Ser Ser Val Ser Ala
1               5                   10                  15

Ala Val Gly Gly Thr Val Thr Ile Asn Cys Gln Ala Ser Lys Asn Ile
            20                  25                  30

Gly Ile Asn Leu Ala Trp Tyr Gln Gln Lys Pro Gly Gln Pro Pro Lys
        35                  40                  45

Gln Leu Ile Trp Tyr Ala Ser Asp Leu Ala Ser Gly Val Pro Ser Arg
    50                  55                  60

Phe Lys Gly Ser Gly Phe Gly Thr Gln Phe Thr Leu Thr Ile Asn Gly
65                  70                  75                  80

Val Gln Arg Glu Asp Ala Ala Thr Tyr Tyr Cys Leu Gly Ser Tyr Gly
                85                  90                  95

Ser Gly Asp Arg Ala Phe Gly Ala Gly Thr Asn Val Glu Ile Lys Arg
            100                 105                 110

Thr Val
```

<210> SEQ ID NO 165
<211> LENGTH: 114
<212> TYPE: PRT
<213> ORGANISM: Homo sapiens

<400> SEQUENCE: 165

```
Gln Ala Ala Glu Leu Val Met Thr Gln Thr Pro Ser Ser Thr Ser Thr
1               5                   10                  15

Ala Val Gly Gly Thr Val Thr Ile Asn Cys Gln Ala Ser Gln Asn Ile
            20                  25                  30
```

-continued

Gly Ile Asn Leu Ala Trp Tyr Gln Gln Lys Pro Gly Gln Pro Pro Lys
                35                  40                  45

Leu Leu Ile Trp Tyr Ala Ser Asp Leu Ala Ser Gly Val Pro Ser Arg
 50                  55                  60

Phe Lys Gly Ser Gly Phe Gly Thr Gln Phe Thr Leu Thr Ile Ser Gly
 65                  70                  75                  80

Val Gln Arg Glu Asp Ala Ala Thr Tyr Tyr Cys Leu Gly Ser Tyr Gly
                85                  90                  95

Ser Gly Asp Arg Ala Phe Gly Ala Gly Thr Asn Val Glu Ile Lys Arg
                100                 105                 110

Thr Val

<210> SEQ ID NO 166
<211> LENGTH: 114
<212> TYPE: PRT
<213> ORGANISM: Homo sapiens

<400> SEQUENCE: 166

Gln Ala Ala Glu Leu Asp Leu Thr Gln Thr Pro Ser Ser Thr Ser Thr
 1               5                  10                  15

Ala Val Gly Gly Thr Val Thr Ile Asn Cys Gln Ala Ser Gln Asn Ile
                20                  25                  30

Gly Ile Asn Leu Ala Trp Phe Gln Gln Lys Pro Gly Gln Pro Pro Lys
                35                  40                  45

Leu Leu Ile Trp Tyr Ala Ser Asp Leu Ala Ser Gly Val Pro Ser Arg
 50                  55                  60

Phe Lys Gly Ser Gly Phe Gly Thr Gln Phe Thr Leu Thr Ile Ser Asn
 65                  70                  75                  80

Val Glu Arg Glu Asp Ala Ala Thr Tyr Tyr Cys Leu Gly Thr Tyr Gly
                85                  90                  95

Ser Gly Asp Arg Ala Phe Gly Ala Gly Thr Asn Val Glu Ile Lys Arg
                100                 105                 110

Thr Val

<210> SEQ ID NO 167
<211> LENGTH: 111
<212> TYPE: PRT
<213> ORGANISM: Homo sapiens

<400> SEQUENCE: 167

Glu Leu Asp Leu Thr Gln Thr Pro Ser Ser Thr Ser Thr Thr Val Gly
 1               5                  10                  15

Gly Thr Val Thr Ile Asn Cys Arg Ala Ser Gln Ile Ile Gly Ile Asn
                20                  25                  30

Leu Ala Trp Tyr Gln Gln Lys Pro Gly Gln Pro Pro Lys Leu Leu Ile
                35                  40                  45

Trp Tyr Ala Ser Asp Leu Ala Ser Gly Val Pro Ser Arg Phe Arg Gly
 50                  55                  60

Asn Val Ser Gly Ser Gln Phe Thr Leu Thr Ile Ser Gly Val Gln Arg
 65                  70                  75                  80

Glu Asp Ala Ala Thr Tyr Tyr Cys Leu Gly Thr Tyr Gly Ser Gly Val
                85                  90                  95

Arg Ala Phe Gly Ala Gly Thr Asn Val Glu Ile Lys Arg Thr Val
                100                 105                 110

<210> SEQ ID NO 168
<211> LENGTH: 114
<212> TYPE: PRT
<213> ORGANISM: Homo sapiens

<400> SEQUENCE: 168

```
Gln Ala Ala Glu Leu Asp Met Thr Gln Thr Pro Ser Ser Thr Ser Thr
1               5                   10                  15

Ala Val Gly Gly Thr Val Thr Met Asn Cys Gln Ala Ser Gln Asn Ile
            20                  25                  30

Gly Ile Asn Leu Ala Trp Tyr Gln Gln Lys Pro Gly Gln Pro Pro Lys
        35                  40                  45

Leu Leu Ile Trp Tyr Ala Ser Asp Leu Ala Ser Gly Val Pro Ser Arg
    50                  55                  60

Phe Lys Gly Ser Gly Phe Gly Thr Gln Phe Thr Leu Thr Ile Ser Gly
65                  70                  75                  80

Met Gln Arg Glu Asp Ala Ala Thr Tyr Tyr Cys Leu Gly Thr Tyr Gly
                85                  90                  95

Ser Gly Val Arg Ala Phe Gly Ala Gly Thr Asn Val Glu Ile Lys Arg
            100                 105                 110

Thr Val
```

<210> SEQ ID NO 169
<211> LENGTH: 55
<212> TYPE: PRT
<213> ORGANISM: Homo sapiens

<400> SEQUENCE: 169

```
Gly Val Pro Ser Arg Phe Lys Gly Ser Gly Phe Gly Thr Gln Phe Thr
1               5                   10                  15

Leu Thr Ile Ser Ala Ile Gln Arg Glu Asp Ala Ala Thr Tyr Tyr Cys
            20                  25                  30

Leu Gly Thr Tyr Gly Ser Gly Val Arg Ala Phe Gly Ala Gly Thr Asn
        35                  40                  45

Val Glu Ile Lys Arg Thr Val
    50                  55
```

<210> SEQ ID NO 170
<211> LENGTH: 114
<212> TYPE: PRT
<213> ORGANISM: Homo sapiens

<400> SEQUENCE: 170

```
Gln Ala Ala Glu Leu Val Leu Thr Gln Thr Pro Ser Ser Thr Ser Thr
1               5                   10                  15

Ala Val Gly Gly Thr Val Thr Ile Asn Cys Gln Ala Ser Gln Asn Ile
            20                  25                  30

Gly Ile Asn Leu Ala Trp Tyr Gln Gln Lys Pro Gly Gln Pro Pro Lys
        35                  40                  45

Leu Leu Ile Trp Tyr Thr Ser Asp Leu Ala Ser Gly Val Pro Ser Arg
    50                  55                  60

Phe Arg Gly Ser Gly Phe Gly Thr Gln Phe Thr Leu Thr Ile Ser Ala
65                  70                  75                  80

Ile Gln Arg Glu Asp Ala Ala Thr Tyr Tyr Cys Leu Gly Thr Tyr Gly
                85                  90                  95

Ser Gly Val Arg Ala Phe Gly Ala Gly Thr Asn Val Glu Ile Lys Arg
            100                 105                 110
```

```
Thr Val

<210> SEQ ID NO 171
<211> LENGTH: 114
<212> TYPE: PRT
<213> ORGANISM: Homo sapiens

<400> SEQUENCE: 171

Gln Ala Ala Glu Leu Val Met Thr Gln Thr Pro Ser Ser Thr Ser Thr
1               5                   10                  15

Ala Val Gly Gly Thr Val Thr Ile Asn Cys Gln Ala Ser Gln Asn Ile
            20                  25                  30

Gly Ile Asn Leu Ala Trp Tyr Gln Gln Lys Pro Gly Gln Pro Pro Lys
        35                  40                  45

Leu Leu Ile Trp Tyr Ala Ser Asp Leu Ala Ser Gly Ala Pro Ser Arg
    50                  55                  60

Phe Lys Gly Ser Gly Phe Gly Thr Gln Phe Thr Leu Thr Ile Ser Gly
65                  70                  75                  80

Val Gln Arg Glu Asp Ala Ala Thr Tyr Tyr Cys Leu Gly Thr Tyr Gly
                85                  90                  95

Ser Gly Asp Arg Ala Phe Gly Ala Gly Thr Asn Val Glu Ile Lys Arg
                100                 105                 110

Thr Val
```